(12) United States Patent
Raum et al.

(10) Patent No.: US 9,067,993 B2
(45) Date of Patent: *Jun. 30, 2015

(54) ANTIBODY NEUTRALIZERS OF HUMAN GRANULOCYTE MACROPHAGE COLONY STIMULATING FACTOR

(75) Inventors: Tobias Raum, Munich (DE); Julia Hepp, Zurich (CH); Eva Vieser, Munich (DE); Silke Petsch, Penzberg (DE); Steven Zeman, Pullach (DE); Andreas Wolf, Gauting (DE); Sandra Bruckmaier, Munich (DE)

(73) Assignee: AMGEN RESEARCH (MUNICH) GMBH, Munich (DE)

( * ) Notice: Subject to any disclaimer, the term of this patent is extended or adjusted under 35 U.S.C. 154(b) by 959 days.

This patent is subject to a terminal disclaimer.

(21) Appl. No.: 13/198,558

(22) Filed: Aug. 4, 2011

(65) Prior Publication Data

US 2012/0009195 A1 Jan. 12, 2012

Related U.S. Application Data

(63) Continuation of application No. 11/918,368, filed as application No. PCT/EP2006/003528 on Apr. 18, 2006, now Pat. No. 8,017,748.

(30) Foreign Application Priority Data

Apr. 18, 2005 (EP) ..................... 05008410

(51) Int. Cl.
*A61K 39/395* (2006.01)
*C07K 16/24* (2006.01)
*A61K 39/00* (2006.01)

(52) U.S. Cl.
CPC ......... *C07K 16/243* (2013.01); *A61K 2039/505* (2013.01); *C07K 2317/21* (2013.01); *C07K 2317/24* (2013.01); *C07K 2317/33* (2013.01); *C07K 2317/34* (2013.01); *C07K 2317/56* (2013.01); *C07K 2317/622* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 6,689,869 | B2 | 2/2004 | Waldmann et al. |
| 6,846,634 | B1 | 1/2005 | Tomlinson et al. |
| 7,741,450 | B2 | 6/2010 | Sass et al. |
| 8,017,748 | B2 * | 9/2011 | Raum et al. .................. 536/23.1 |
| 8,318,168 | B2 | 11/2012 | Sass et al. |
| 8,623,364 | B2 | 1/2014 | Sass et al. |
| 2005/0271663 | A1 * | 12/2005 | Ignatovich et al. ........ 424/145.1 |
| 2014/0086928 | A1 | 3/2014 | Sass et al. |

FOREIGN PATENT DOCUMENTS

| EP | 0265384 | A2 | 4/1988 |
| EP | 0344957 | A1 | 12/1989 |
| EP | 0499161 | A2 | 8/1992 |
| EP | 1256348 | A1 | 11/2002 |
| EP | 1593690 | A | 11/2005 |
| WO | WO 03/068924 | | 8/2001 |
| WO | WO-2006/122797 | A2 | 11/2006 |

OTHER PUBLICATIONS

Oggero, et al. "Defininig the antigenic structure of human GM-CSF and its implications for receptor interactin and therapeutic treatments," Molecular Diversity 8:257-269 (2004).
Beiboer et al., "Guided Selection of a Pan Carcinoma Specific Antibody Reveals Similar Binding Characteristics Yet Structural Divergence Between the Original Murine Antibody and its Human Equivalent," *J. Mol. Biol.* 296: 833-849 (2000).
Dempsey et al., "Monoclonal Antibodies that Recognize Human Granulocyte-Macrophage Colony-Stimulating Factor and Neutralize its Bioactivity in Vitro," *Hybridoma*. 9: 545-558 (1990).
Eberhardt et al., "Identification of Two Potential Receptor Binding Sites for hGM-CSF," *Braz. J. Chem. Eng.* 20: 1-9 (2003).
Kanakura et al., "Identification of Functionally Distinct Domains of Human Granulocyte-Macrophage Colony-Stimulating Factor Using Monoclonal Antibodies," *Blood* 77: 1033-1043 (1991).
Lakhtina et al., "Immunoenzyme Determination of Human Granulocyte-Macrophage Colony-Stimulating Factor Using Monoclonal Antibodies," *Bioorg Khim* 25: 673-678 (1999) (Abstract).
Li et al., "Human Antibodies for Immunotherapy Development Generated via a Human Be Cell Hybridoma Technology," *PNAS* 103: 3557-3562 (2006).
Nice et al., "Human Granulocyte-Macrophage Colony-Stimulating Factor (hGM-CSF): Identification of a Binding Site for a Neutralizing Antibody," *Growth Factors* 3: 159-169 (1990).
Rudikoff et al., "Single Amino Acid Substitution Altering Antigen-Binding Specificity," *PNAS*, 79: 1979-1983 (1982).
Van Dijk et al., "Human Antibodies as Next Generation Therapeutics," *Current Opinion in Chemical Biology* 5: 368-374 (2001).

\* cited by examiner

*Primary Examiner* — Zachary Skelding

(74) *Attorney, Agent, or Firm* — Marshall, Gerstein & Borun LLP

(57) ABSTRACT

The present invention relates to a human monoclonal antibody or fragment thereof which specifically binds to and neutralizes primate GM-CSF.

20 Claims, 35 Drawing Sheets

Figure 8A

Figure 1:
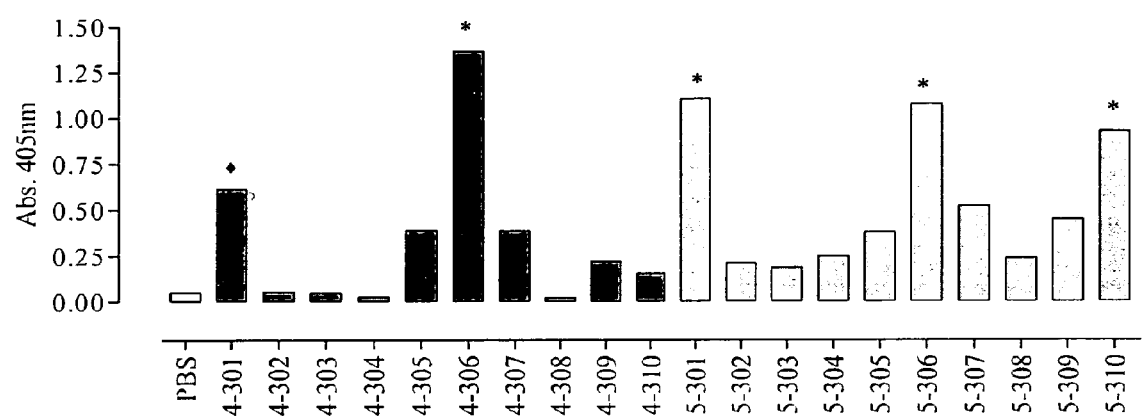

| | | | | |
|---|---|---|---|---|
| Human GM-CSF: | APARSPSPST | QPWEHVNAIQ | EARRLLNLSR | DTAAEMNETV |
| Macaca GM-CSF: | APARSPSPGT | QPWEHVNAIQ | EARRLLNLSR | DTAAEMNKTV |
| Gibbon GM-CSF: | APSRSPSPST | QPWEHVNAIQ | EARRLLNLSR | DTAAEINETV |
| | | | | |
| Human GM-CSF: | EVISEMFDLQ | EPTCLQTRLE | LYKQGLRGSL | TKLKGPLTMM |
| Macaca GM-CSF: | EVVSEMFDLQ | EPSCLQTRLE | LYKQGLQGSL | TKLKGPLTMM |
| Gibbon GM-CSF: | EVVSEMFDLQ | EPTCLQTRLE | LYKQGLRGSL | TKLKGPLTMM |
| | | | | |
| Human GM-CSF: | ASHYKQHCPP | TPETSCATQI | ITFESFKENL | KDFLLVIPFD |
| Macaca GM-CSF: | ASHYKQHCPP | TPETSCATQI | ITFQSFKENL | KDFLLVIPFD |
| Gibbon GM-CSF: | ASHYKQHCPP | TPETSCATQI | IIFESFKENL | KDFLLVIPFD |
| | | | | |
| Human GM-CSF: | CWEPVQE | | | |
| Macaca GM-CSF: | CWEPVQE | | | |
| Gibbon GM-CSF: | CWEPVQG | | | |

- ■ rhGM-CSF (Yeast)
- ○ rhGM-CSF (*E. coli*)
- ● hGM-CSF (human lung)
- ▽ macaque GM-CSF (HEK cells)

A

B

SEQUENCE LISTING

```
<160> NUMBER OF SEQ ID NOS: 56

<210> SEQ ID NO 1
<211> LENGTH: 10
<212> TYPE: PRT
<213> ORGANISM: artificial sequence
<220> FEATURE:
<223> OTHER INFORMATION: Synthetic

<400> SEQUENCE: 1

Ser Gly Leu Ile Ala Asn His Met Thr Pro
1               5                   10

<210> SEQ ID NO 2
<211> LENGTH: 10
<212> TYPE: PRT
<213> ORGANISM: artificial sequence
<220> FEATURE:
<223> OTHER INFORMATION: Synthetic

<400> SEQUENCE: 2

Thr Thr Leu Ile Ser Val Tyr Phe Asp Tyr
1               5                   10

<210> SEQ ID NO 3
<211> LENGTH: 10
<212> TYPE: PRT
<213> ORGANISM: artificial sequence
<220> FEATURE:
<223> OTHER INFORMATION: Synthetic

<400> SEQUENCE: 3

Ser Gly Leu Ile Phe Asp Tyr Trp Leu Asp
1               5                   10

<210> SEQ ID NO 4
<211> LENGTH: 10
<212> TYPE: PRT
<213> ORGANISM: artificial sequence
```

```
<220> FEATURE:
<223> OTHER INFORMATION: Synthetic

<400> SEQUENCE: 4

Ser Gly Leu Ile Ile Asp Ala Leu Ser Pro
1               5                   10

<210> SEQ ID NO 5
<211> LENGTH: 10
<212> TYPE: PRT
<213> ORGANISM: artificial sequence
<220> FEATURE:
<223> OTHER INFORMATION: Synthetic

<400> SEQUENCE: 5

Thr Ser Leu Met Ser Ile Tyr Phe Asp Tyr
1               5                   10

<210> SEQ ID NO 6
<211> LENGTH: 10
<212> TYPE: PRT
<213> ORGANISM: artificial sequence
<220> FEATURE:
<223> OTHER INFORMATION: Synthetic

<400> SEQUENCE: 6

Ser Gly Leu Leu Phe Leu Tyr Phe Asp Tyr
1               5                   10

<210> SEQ ID NO 7
<211> LENGTH: 10
<212> TYPE: PRT
<213> ORGANISM: artificial sequence
<220> FEATURE:
<223> OTHER INFORMATION: Synthetic

<400> SEQUENCE: 7

Ser Gly Leu Ile Asn Leu Gly Met His Pro
1               5                   10

<210> SEQ ID NO 8
<211> LENGTH: 10
<212> TYPE: PRT
<213> ORGANISM: artificial sequence
<220> FEATURE:
<223> OTHER INFORMATION: Synthetic

<400> SEQUENCE: 8

Ser Gly Leu Ile Phe Asp Ala Leu Arg Asp
1               5                   10

<210> SEQ ID NO 9
<211> LENGTH: 10
<212> TYPE: PRT
<213> ORGANISM: artificial sequence
<220> FEATURE:
<223> OTHER INFORMATION: Synthetic

<400> SEQUENCE: 9

Ser Gly Leu Ile Phe Asp Lys Leu Thr Ser
1               5                   10

<210> SEQ ID NO 10
<211> LENGTH: 10
<212> TYPE: PRT
<213> ORGANISM: artificial sequence
```

```
<220> FEATURE:
<223> OTHER INFORMATION: Synthetic

<400> SEQUENCE: 10

Ser Gly Leu Ile Asn Leu His Phe Asp Thr
1               5                   10

<210> SEQ ID NO 11
<211> LENGTH: 10
<212> TYPE: PRT
<213> ORGANISM: artificial sequence
<220> FEATURE:
<223> OTHER INFORMATION: Synthetic

<400> SEQUENCE: 11

Ser Thr His Phe Ser Ala Tyr Phe Asp Tyr
1               5                   10

<210> SEQ ID NO 12
<211> LENGTH: 10
<212> TYPE: PRT
<213> ORGANISM: artificial sequence
<220> FEATURE:
<223> OTHER INFORMATION: Synthetic

<400> SEQUENCE: 12

Ser Gly Leu Ile Met Asp Lys Leu Asp Asn
1               5                   10

<210> SEQ ID NO 13
<211> LENGTH: 10
<212> TYPE: PRT
<213> ORGANISM: artificial sequence
<220> FEATURE:
<223> OTHER INFORMATION: Synthetic

<400> SEQUENCE: 13

Ser Gly Leu Ile Ile Asp Asn Leu Asn Pro
1               5                   10

<210> SEQ ID NO 14
<211> LENGTH: 5
<212> TYPE: PRT
<213> ORGANISM: artificial sequence
<220> FEATURE:
<223> OTHER INFORMATION: Synthetic

<400> SEQUENCE: 14

Asp Tyr Leu Leu His
1               5

<210> SEQ ID NO 15
<211> LENGTH: 17
<212> TYPE: PRT
<213> ORGANISM: artificial sequence
<220> FEATURE:
<223> OTHER INFORMATION: Synthetic

<400> SEQUENCE: 15

Trp Leu Asn Pro Tyr Ser Gly Asp Thr Asn Tyr Ala Gln Lys Phe Gln
1               5                   10                  15

Gly
```

```
<210> SEQ ID NO 16
<211> LENGTH: 11
<212> TYPE: PRT
<213> ORGANISM: artificial sequence
<220> FEATURE:
<223> OTHER INFORMATION: Synthetic

<400> SEQUENCE: 16

Arg Ala Ser Gln Asn Ile Arg Asn Ile Leu Asn
1               5                   10

<210> SEQ ID NO 17
<211> LENGTH: 7
<212> TYPE: PRT
<213> ORGANISM: artificial sequence
<220> FEATURE:
<223> OTHER INFORMATION: Synthetic

<400> SEQUENCE: 17

Ala Ala Ser Asn Leu Gln Ser
1               5

<210> SEQ ID NO 18
<211> LENGTH: 9
<212> TYPE: PRT
<213> ORGANISM: artificial sequence
<220> FEATURE:
<223> OTHER INFORMATION: Synthetic

<400> SEQUENCE: 18

Gln Gln Ser Tyr Ser Met Pro Arg Thr
1               5

<210> SEQ ID NO 19
<211> LENGTH: 107
<212> TYPE: PRT
<213> ORGANISM: artificial sequence
<220> FEATURE:
<223> OTHER INFORMATION: Synthetic

<400> SEQUENCE: 19

Asp Ile Gln Met Thr Gln Ser Pro Ser Ser Val Ser Ala Ser Val Gly
1               5                   10                  15

Asp Arg Val Thr Ile Ala Cys Arg Ala Ser Gln Asn Ile Arg Asn Ile
            20                  25                  30

Leu Asn Trp Tyr Gln Gln Arg Pro Gly Lys Ala Pro Gln Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Met Pro Arg
                85                  90                  95

Thr Phe Gly Gly Gly Thr Lys Leu Glu Ile Lys
            100                 105

<210> SEQ ID NO 20
<211> LENGTH: 119
<212> TYPE: PRT
<213> ORGANISM: artificial sequence
<220> FEATURE:
<223> OTHER INFORMATION: Synthetic
```

<400> SEQUENCE: 20

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Ile Ala Asn His Met Thr Pro Trp Gly Gln Gly
            100                 105                 110

Thr Met Val Thr Val Ser Ser
        115

<210> SEQ ID NO 21
<211> LENGTH: 119
<212> TYPE: PRT
<213> ORGANISM: artificial sequence
<220> FEATURE:
<223> OTHER INFORMATION: Synthetic

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Thr Thr Leu Ile Ser Val Tyr Phe Asp Tyr Trp Gly Gln Gly
            100                 105                 110

Thr Met Val Thr Val Ser Ser
        115

<210> SEQ ID NO 22
<211> LENGTH: 119
<212> TYPE: PRT
<213> ORGANISM: artificial sequence
<220> FEATURE:
<223> OTHER INFORMATION: Synthetic

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

-continued

```
Gly Trp Leu Asn Pro Tyr Ser Gly Asp Thr Asn Tyr Ala Gln Lys Phe
        50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Thr Arg Ser Gly Leu Ile Ala Val Tyr Phe Asp Tyr Trp Gly Gln Gly
            100                 105                 110

Thr Met Val Thr Val Ser Ser
            115
```

<210> SEQ ID NO 23
<211> LENGTH: 119
<212> TYPE: PRT
<213> ORGANISM: artificial sequence
<220> FEATURE:
<223> OTHER INFORMATION: Synthetic

<400> SEQUENCE: 23

```
Glu Val Gln Leu Leu Glu Ser Gly Ala Glu Val Lys Lys Pro Gly Ala
 1               5                  10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
        50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Ala Arg Ser Gly Leu Ile Phe Asp Tyr Trp Leu Asp Trp Gly Gln Gly
            100                 105                 110

Thr Met Val Thr Val Ser Ser
            115
```

<210> SEQ ID NO 24
<211> LENGTH: 119
<212> TYPE: PRT
<213> ORGANISM: artificial sequence
<220> FEATURE:
<223> OTHER INFORMATION: Synthetic

<400> SEQUENCE: 24

```
Glu Val Gln Leu Leu Glu Ser Gly Ala Glu Val Lys Lys Pro Gly Ala
 1               5                  10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
        50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95
```

```
Ala Arg Ser Gly Leu Ile Ile Asp Ala Leu Ser Pro Trp Gly Gln Gly
            100                 105                 110

Thr Met Val Thr Val Ser Ser
        115

<210> SEQ ID NO 25
<211> LENGTH: 119
<212> TYPE: PRT
<213> ORGANISM: artificial sequence
<220> FEATURE:
<223> OTHER INFORMATION: Synthetic

<400> SEQUENCE: 25

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Thr Ser Leu Met Ser Ile Tyr Phe Asp Tyr Trp Gly Gln Gly
            100                 105                 110

Thr Met Val Thr Val Ser Ser
        115

<210> SEQ ID NO 26
<211> LENGTH: 119
<212> TYPE: PRT
<213> ORGANISM: artificial sequence
<220> FEATURE:
<223> OTHER INFORMATION: Synthetic

<400> SEQUENCE: 26

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Leu Phe Leu Tyr Phe Asp Tyr Trp Gly Gln Gly
            100                 105                 110

Thr Met Val Thr Val Ser Ser
        115

<210> SEQ ID NO 27
<211> LENGTH: 119
<212> TYPE: PRT
<213> ORGANISM: artificial sequence
```

-continued

```
<220> FEATURE:
<223> OTHER INFORMATION: Synthetic

<400> SEQUENCE: 27

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Asn Leu Gly Met His Pro Trp Gly Gln Gly
            100                 105                 110

Thr Met Val Thr Val Ser Ser
        115

<210> SEQ ID NO 28
<211> LENGTH: 119
<212> TYPE: PRT
<213> ORGANISM: artificial sequence
<220> FEATURE:
<223> OTHER INFORMATION: Synthetic

<400> SEQUENCE: 28

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Phe Asp Ala Leu Arg Asp Trp Gly Gln Gly
            100                 105                 110

Thr Met Val Thr Val Ser Ser
        115

<210> SEQ ID NO 29
<211> LENGTH: 119
<212> TYPE: PRT
<213> ORGANISM: artificial sequence
<220> FEATURE:
<223> OTHER INFORMATION: Synthetic

<400> SEQUENCE: 29

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30
```

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
 50                      55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Phe Asp Lys Leu Thr Ser Trp Gly Gln Gly
                100                 105                 110

Thr Met Val Thr Val Ser Ser
            115

<210> SEQ ID NO 30
<211> LENGTH: 119
<212> TYPE: PRT
<213> ORGANISM: artificial sequence
<220> FEATURE:
<223> OTHER INFORMATION: Synthetic

<400> SEQUENCE: 30

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
 50                      55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Asn Leu His Phe Asp Thr Trp Gly Gln Gly
                100                 105                 110

Thr Met Val Thr Val Ser Ser
            115

<210> SEQ ID NO 31
<211> LENGTH: 119
<212> TYPE: PRT
<213> ORGANISM: artificial sequence
<220> FEATURE:
<223> OTHER INFORMATION: Synthetic

<400> SEQUENCE: 31

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
 50                      55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Thr His Phe Ser Ala Tyr Phe Asp Tyr Trp Gly Gln Gly
            100                 105                 110

Thr Met Val Thr Val Ser Ser
        115

<210> SEQ ID NO 32
<211> LENGTH: 119
<212> TYPE: PRT
<213> ORGANISM: artificial sequence
<220> FEATURE:
<223> OTHER INFORMATION: Synthetic

<400> SEQUENCE: 32

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Met Asp Lys Leu Asp Asn Trp Gly Gln Gly
            100                 105                 110

Thr Met Val Thr Val Ser Ser
        115

<210> SEQ ID NO 33
<211> LENGTH: 119
<212> TYPE: PRT
<213> ORGANISM: artificial sequence
<220> FEATURE:
<223> OTHER INFORMATION: Synthetic

<400> SEQUENCE: 33

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Ile Asp Asn Leu Asn Pro Trp Gly Gln Gly
            100                 105                 110

Thr Met Val Thr Val Ser Ser
        115

<210> SEQ ID NO 34
<211> LENGTH: 214
<212> TYPE: PRT
<213> ORGANISM: artificial sequence
<220> FEATURE:
<223> OTHER INFORMATION: Synthetic

<400> SEQUENCE: 34

Asp Ile Gln Met Thr Gln Ser Pro Ser Ser Val Ser Ala Ser Val Gly
1               5                   10                  15

Asp Arg Val Thr Ile Ala Cys Arg Ala Ser Gln Asn Ile Arg Asn Ile
            20                  25                  30

Leu Asn Trp Tyr Gln Gln Arg Pro Gly Lys Ala Pro Gln Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Met Pro Arg
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 35
<211> LENGTH: 449
<212> TYPE: PRT
<213> ORGANISM: artificial sequence
<220> FEATURE:
<223> OTHER INFORMATION: Synthetic

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Thr Thr Leu Ile Ser Val Tyr Phe Asp Tyr Trp Gly Gln Gly
            100                 105                 110

```
Thr Met Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Lys Lys Val Glu Pro Lys Ser Cys Asp Lys
        210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
                275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Asp Glu Leu Thr Lys Asn Gln Val Ser Leu Thr
                355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
                435                 440                 445
Lys

<210> SEQ ID NO 36
<211> LENGTH: 449
<212> TYPE: PRT
<213> ORGANISM: artificial sequence
<220> FEATURE:
<223> OTHER INFORMATION: Synthetic
```

<400> SEQUENCE: 36

```
Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Ile Ala Asn His Met Thr Pro Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

```
Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 37
<211> LENGTH: 449
<212> TYPE: PRT
<213> ORGANISM: artificial sequence
<220> FEATURE:
<223> OTHER INFORMATION: Synthetic

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Phe Asp Tyr Trp Leu Asp Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

Tyr Lys Cys Lys Val Ser Asn Lys Ala Leu Pro Ala Pro Ile Glu Lys
              325                 330                 335

Thr Ile Ser Lys Ala Lys Gly Gln Pro Arg Glu Pro Gln Val Tyr Thr
              340                 345                 350

Leu Pro Pro Ser Arg Asp Glu Leu Thr Lys Asn Gln Val Ser Leu Thr
              355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
              405                 410                 415

Ser Arg Trp Gln Gln Gly Asn Val Phe Ser Cys Ser Val Met His Glu
              420                 425                 430

Ala Leu His Asn His Tyr Thr Gln Lys Ser Leu Ser Leu Ser Pro Gly
              435                 440                 445

Lys

<210> SEQ ID NO 38
<211> LENGTH: 449
<212> TYPE: PRT
<213> ORGANISM: artificial sequence
<220> FEATURE:
<223> OTHER INFORMATION: Synthetic

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
              20                  25                  30

Leu Leu His Trp Val Arg Gln Ala Pro Gly Gln Gly Leu Glu Trp Val
              35                  40                  45

Gly Trp Leu Asn Pro Tyr Ser Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
              85                  90                  95

Ala Arg Ser Gly Leu Ile Ile Asp Ala Leu Ser Pro Trp Gly Gln Gly
              100                 105                 110

Thr Met Val Thr Val Ser Ser Ala Ser Thr Lys Gly Pro Ser Val Phe
              115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
              165                 170                 175

Gln Ser Ser Gly Leu Tyr Ser Leu Ser Ser Val Val Thr Val Pro Ser
              180                 185                 190

Ser Ser Leu Gly Thr Gln Thr Tyr Ile Cys Asn Val Asn His Lys Pro
              195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 39
<211> LENGTH: 449
<212> TYPE: PRT
<213> ORGANISM: artificial sequence
<220> FEATURE:
<223> OTHER INFORMATION: Synthetic

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Thr Arg Thr Ser Leu Met Ser Ile Tyr Phe Asp Tyr Trp Gly Gln Gly
            100                 105                 110

Thr Met Val Thr Val Ser Ser Ala Ser Thr Lys Gly Pro Ser Val Phe
        115                 120                 125

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 40
<211> LENGTH: 449
<212> TYPE: PRT
<213> ORGANISM: artificial sequence
<220> FEATURE:
<223> OTHER INFORMATION: Synthetic

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30
```

```
Leu Leu His Trp Val Arg Gln Ala Pro Gly Gln Gly Leu Glu Trp Val
         35                  40                  45

Gly Trp Leu Asn Pro Tyr Ser Gly Asp Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Thr Arg Ser Gly Leu Leu Phe Leu Tyr Phe Asp Tyr Trp Gly Gln Gly
                100                 105                 110

Thr Met Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                    165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys
```

<210> SEQ ID NO 41
<211> LENGTH: 449
<212> TYPE: PRT
<213> ORGANISM: artificial sequence
<220> FEATURE:
<223> OTHER INFORMATION: Synthetic

<400> SEQUENCE: 41

```
Gln Val Gln Leu Val Gln Ser Gly Ala Glu Val Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Asn Leu Gly Met His Pro Trp Gly Gln Gly
                100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 42
<211> LENGTH: 449
<212> TYPE: PRT
<213> ORGANISM: artificial sequence
<220> FEATURE:
<223> OTHER INFORMATION: Synthetic

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Phe Asp Ala Leu Arg Asp Trp Gly Gln Gly
                100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 43
<211> LENGTH: 449
<212> TYPE: PRT
<213> ORGANISM: artificial sequence
<220> FEATURE:
<223> OTHER INFORMATION: Synthetic

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Phe Asp Lys Leu Thr Ser Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 44
<211> LENGTH: 449
<212> TYPE: PRT
<213> ORGANISM: artificial sequence
<220> FEATURE:
<223> OTHER INFORMATION: Synthetic

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80
```

Met Glu Leu Ser Arg Leu Arg Ser Asp Asp Thr Ala Val Tyr Tyr Cys
                    85                  90                  95

Ala Arg Ser Gly Leu Ile Asn Leu His Phe Asp Thr Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 45
<211> LENGTH: 449
<212> TYPE: PRT
<213> ORGANISM: artificial sequence
<220> FEATURE:
<223> OTHER INFORMATION: Synthetic -continued

```
<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Thr His Phe Ser Ala Tyr Phe Asp Tyr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 46
<211> LENGTH: 449
<212> TYPE: PRT
<213> ORGANISM: artificial sequence
<220> FEATURE:
<223> OTHER INFORMATION: Synthetic

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Met Asp Lys Leu Asp Asn Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 47
<211> LENGTH: 449
<212> TYPE: PRT
<213> ORGANISM: artificial sequence
<220> FEATURE:
<223> OTHER INFORMATION: Synthetic

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
            85                  90                  95

Ala Arg Ser Gly Leu Ile Ile Asp Asn Leu Asn Pro Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Asp Glu Leu Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 48
<211> LENGTH: 449
<212> TYPE: PRT
<213> ORGANISM: artificial sequence
<220> FEATURE:
<223> OTHER INFORMATION: Synthetic

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Ile Ala Val Tyr Phe Asp Tyr Trp Gly Gln Gly
            100                 105                 110

Thr Met Val Thr Val Ser Ser Ala Ser Thr Lys Gly Pro Ser Val Phe
        115                 120                 125

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 49
<211> LENGTH: 127
<212> TYPE: PRT
<213> ORGANISM: Homo sapiens

<400> SEQUENCE: 49

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
                20                  25                  30

Ala Ala Glu Met Asn Glu Thr Val Glu Val Ile Ser Glu Met Phe Asp
            35                  40                  45
```

```
Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
 65                  70                  75                  80

Ala Ser His Tyr Lys Gln His Cys Pro Pro Thr Pro Glu Thr Ser Cys
                 85                  90                  95

Ala Thr Gln Ile Ile Thr Phe Glu Ser Phe Lys Glu Asn Leu Lys Asp
                100                 105                 110

Phe Leu Val Ile Pro Phe Asp Cys Trp Glu Pro Val Gln Glu
            115                 120                 125
```

<210> SEQ ID NO 50
<211> LENGTH: 127
<212> TYPE: PRT
<213> ORGANISM: Macaca mulatta

<400> SEQUENCE: 50

```
Ala Pro Ala Arg Ser Pro Ser Pro Gly Thr Gln Pro Trp Glu His Val
 1               5                  10                  15

Asn Ala Ile Gln Glu Ala Arg Arg Leu Leu Asn Leu Ser Arg Asp Thr
                20                  25                  30

Ala Ala Glu Met Asn Lys Thr Val Glu Val Val Ser Glu Met Phe Asp
            35                  40                  45

Leu Gln Glu Pro Ser Cys Leu Gln Thr Arg Leu Glu Leu Tyr Lys Gln
    50                  55                  60

Gly Leu Gln Gly Ser Leu Thr Lys Leu Lys Gly Pro Leu Thr Met Met
 65                  70                  75                  80

Ala Ser His Tyr Lys Gln His Cys Pro Pro Thr Pro Glu Thr Ser Cys
                 85                  90                  95

Ala Thr Gln Ile Ile Thr Phe Gln Ser Phe Lys Glu Asn Leu Lys Asp
                100                 105                 110

Phe Leu Leu Val Ile Pro Phe Asp Cys Trp Glu Pro Val Gln Glu
            115                 120                 125
```

<210> SEQ ID NO 51
<211> LENGTH: 127
<212> TYPE: PRT
<213> ORGANISM: Hylobates lar

<400> SEQUENCE: 51

```
Ala Pro Ser Arg Ser Pro Ser Pro Ser Thr Gln Pro Trp Glu His Val
 1               5                  10                  15

Asn Ala Ile Gln Glu Ala Arg Arg Leu Leu Asn Leu Ser Arg Asp Thr
                20                  25                  30

Ala Ala Glu Ile Asn Glu Thr Val Glu Val Val Ser Glu Met Phe Asp
            35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
 65                  70                  75                  80

Ala Ser His Tyr Lys Gln His Cys Pro Pro Thr Pro Glu Thr Ser Cys
                 85                  90                  95

Ala Thr Gln Ile Ile Ile Phe Glu Ser Phe Lys Glu Asn Leu Lys Asp
                100                 105                 110

Phe Leu Leu Val Ile Pro Phe Asp Cys Trp Glu Pro Val Gln Gly
            115                 120                 125
```

<210> SEQ ID NO 52
<211> LENGTH: 119
<212> TYPE: PRT
<213> ORGANISM: artificial sequence
<220> FEATURE:
<223> OTHER INFORMATION: Synthetic

<400> SEQUENCE: 52

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Thr Thr Leu Ile Ser Val Tyr Phe Asp Tyr Trp Gly Gln Gly
            100                 105                 110

Thr Met Val Thr Val Ser Ser
        115

<210> SEQ ID NO 53
<211> LENGTH: 119
<212> TYPE: PRT
<213> ORGANISM: artificial sequence
<220> FEATURE:
<223> OTHER INFORMATION: Synthetic

<400> SEQUENCE: 53

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Ile Ala Val Tyr Phe Asp Tyr Trp Gly Gln Gly
            100                 105                 110

Thr Met Val Thr Val Ser Ser
        115

<210> SEQ ID NO 54
<211> LENGTH: 107
<212> TYPE: PRT
<213> ORGANISM: artificial sequence
<220> FEATURE:
<223> OTHER INFORMATION: Synthetic -continued

```
<400> SEQUENCE: 54

Glu Leu Val Met Thr Gln Ser Pro Ser Val Ser Ala Ser Val Gly
1               5                   10                  15

Asp Arg Val Thr Ile Ala Cys Arg Ala Ser Gln Asn Ile Arg Asn Ile
            20                  25                  30

Leu Asn Trp Tyr Gln Gln Arg Pro Gly Lys Ala Pro Gln Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Met Pro Arg
                85                  90                  95

Thr Phe Gly Gly Gly Thr Lys Val Glu Ile Lys
            100                 105

<210> SEQ ID NO 55
<211> LENGTH: 107
<212> TYPE: PRT
<213> ORGANISM: artificial sequence
<220> FEATURE:
<223> OTHER INFORMATION: Synthetic

<400> SEQUENCE: 55

Asp Ile Gln Met Thr Gln Ser Pro Ser Val Ser Ala Ser Val Gly
1               5                   10                  15

Asp Arg Val Thr Ile Ala Cys Arg Ala Ser Gln Asn Ile Arg Asn Ile
            20                  25                  30

Leu Asn Trp Tyr Gln Gln Arg Pro Gly Lys Ala Pro Gln Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Met Pro Arg
                85                  90                  95

Thr Phe Gly Gly Gly Thr Lys Val Glu Ile Lys
            100                 105

<210> SEQ ID NO 56
<211> LENGTH: 10
<212> TYPE: PRT
<213> ORGANISM: artificial sequence
<220> FEATURE:
<223> OTHER INFORMATION: Synthetic

<400> SEQUENCE: 56

Ser Gly Leu Ile Ala Val Tyr Phe Asp Tyr
1               5                   10
```

ANTIBODY NEUTRALIZERS OF HUMAN GRANULOCYTE MACROPHAGE COLONY STIMULATING FACTOR

CROSS REFERENCE TO RELATED APPLICATIONS

This application is a continuation of U.S. application Ser. No. 11/918,368, filed Oct. 12, 2007, which is the U.S. National Stage of International Application No. PCT/EP2006/003528, filed Apr. 18, 2006, which claims benefit of European Patent Application No. 05008410.2, filed Apr. 18, 2005, each of which is hereby incorporated by reference.

The present invention relates to antibodies and fragments thereof which neutralize the activity of human granulocyte macrophage colony stimulating factor (GM-CSF). The invention further relates to pharmaceutical compositions comprising such antibodies and fragments thereof as well as to uses of such antibodies and fragments thereof for the preparation of medicaments for the treatment of various conditions.

Originally described as a potent stimulus of the growth and differentiation of granulocyte and macrophage precursor cells in vitro, granulocyte-macrophage colony-stimulating factor (GM-CSF) is an approximately 23 kDa glycoprotein with a four alpha helical bundle structure that binds to a heterodimeric receptor composed of subunits belonging to the type 1 cytokine receptor family. It stimulates the maturation of i.a. macrophages, neutrophils, granulocytes, eosinophils and antigen-presenting dendritic cells, to increase their functional capacity in combating infections. Genetic ablation experiments i.e. experiments silencing or knocking out the gene of interest—here GM-CSF—in mice indicated that GM-CSF is essential for maintaining the functional activity of some macrophage populations such as those involved in clearing surfactant in the lung and in responding to certain kinds of infection or immune responses.

While GM-CSF has potent stimulatory activities in vitro on progenitor cells for neutrophils, eosinophils, macrophages, and to a lesser extent erythroid and megakaryocytic cells, results obtained in vivo with gene knockout mice suggest that the major physiological role of GM-CSF is to maintain or stimulate the functional activity of mature macrophages and granulocytes and to stimulate antigen presentation to the immune system. It does the latter by its direct effects on dendritic cell and macrophage production, but also by increasing expression of the class II major histocompatibility complex and Fc receptors on macrophages and dendritic cells.

GM-CSF stimulates the functional activities of neutrophils, eosinophils, and monocyte-macrophages. These include enhancement of chemotactic activity, increased expression of cellular adhesion molecules and increased adhesion to surfaces, and increased phagocytic activity as well as inhibition and delay of apoptosis of these cells. Neutrophils represent the first line of defence against aggressions. The programmed death of neutrophils is delayed by pro-inflammatory stimuli including GM-CSF to ensure a proper resolution of the inflammation in time and place. GM-CSF also stimulates the capacity of these cells to mediate antibody-dependent cell cytotoxicity and to kill microorganisms intracellularly and has a 'priming' effect on these cells to enhance their response to subsequent stimuli for the oxidative burst (superoxide anion production), degranulation and release of antimicrobial agents, and chemotaxis. Further, GM-CSF stimulates the release of secondary cytokines and mediators from these cells including IL-1, G-CSF, M-CSF, and leukotrienes from neutrophils, as well as IL-1, TNF, IL-6, G-CSF, M-CSF, and prostaglandins from macrophages.

It is clear from the above that GM-CSF plays a key role in activating and maintaining the cell populations necessary to ward off infection. However, in some instances activation of these cell populations may be undesirable. For example, activation of the above cell lineages when no pathogen is present leads in many instances to acute and/or chronic inflammatory conditions which, in extreme cases, may be life-threatening. Similarly, over-expression of GM-CSF may lead to excess immune activation, resulting in inflammation. In such instances, it may be desirable to neutralize the activity of GM-CSF such that the symptoms of these inflammatory conditions are eliminated or at least mitigated.

Examples of such neutralizing activity exist in the prior art. For example, it was found that a neutralizing anti-GM-CSF antibody contributed to an increase in eosinophil apoptosis rate in peripheral blood samples (Kankaanranta et al. (2000) Journal of Allergy and Clinical Immunology 106, 77-83). As enhanced eosinophil survival is correlated with asthma, an increase in eosinophil apoptosis would be expected to mitigate asthmatic symptoms.

In chronic inflammatory diseases such as asthma, rheumatoid arthritis, and multiple sclerosis levels of GM-CSF are increased locally and in some cases systemically and have been correlated with the inflammatory process in these diseases.

It is therefore an aim of the invention to improve on the modes of neutralizing increased and/or undesired GM-CSF activity previously known in the prior art.

Accordingly one aspect of the invention relates to a human monoclonal antibody or fragment thereof which specifically binds to and neutralizes primate GM-CSF.

The term "specifically binds" or related expressions such as "specific binding", "binding specifically", "specific binder" etc. as used herein refer to the ability of the human monoclonal antibody or fragment thereof to discriminate between primate GM-CSF and any number of other potential antigens different from primate GM-CSF to such an extent that, from a pool of a plurality of different antigens as potential binding partners, only primate GM-CSF is bound, or is significantly bound. Within the meaning of the invention, primate GM-CSF is "significantly" bound when, from among a pool of a plurality of equally accessible different antigens as potential binding partners, primate GM-CSF is bound at least 10-fold, preferably 50-fold, most preferably 100-fold or greater more frequently (in a kinetic sense) than any other antigen different than primate GM-CSF. Such kinetic measurements can be performed on a Biacore apparatus.

As used herein, "neutralization," "neutralizer," "neutralizing" and grammatically related variants thereof refer to partial or complete attenuation of the biological effect(s) of GM-CSF. Such partial or complete attenuation of the biological effect(s) of GM-CSF results from modification, interruption and/or abrogation of GM-CSF-mediated signal transduction, as manifested, for example, in intracellular signalling, cellular proliferation or release of soluble substances, up- or down-regulation of intracellular gene activation, for example that resulting in expression of surface receptors for ligands other than GM-CSF. As one of skill in the art understands, there exist multiple modes of determining whether an agent, for example an antibody in question or fragment thereof is to be classified as a neutralizer. As an example, this may be accomplished by a standard in vitro test performed generally as follows: In a first proliferation experiment, a cell line, the degree of proliferation of which is known to depend on the activity of GM-CSF, is incubated in a series of samples with varying concentrations of GM-CSF, following which incubation the degree of proliferation of the cell line is measured. From this measurement, the concentration of GM-CSF allowing half-maximal proliferation of the cells is determined A second proliferation experiment is then performed employing in each of a series of samples the same number of cells as used in the first proliferation experiment, the above-determined concentration of GM-CSF and, this time, varying concentrations of an antibody or fragment thereof suspected of being a neutralizer of GM-CSF. Cell proliferation is again measured to determine the concentration of antibody or fragment thereof sufficient to effect half-maximal growth inhibition. If the resulting graph of growth inhibition vs. concentration of antibody (or fragment thereof) is sigmoidal in shape, resulting in decreased cell proliferation with increasing concentration of antibody (or fragment thereof), then some degree of antibody-dependent growth inhibition has been effected, i.e. the activity of GM-CSF has been neutralized to some extent. In such a case, the antibody or fragment thereof may be considered a "neutralizer" in the sense of the present invention. One example of a cell line, the degree of proliferation of which is known to depend on the activity of GM-CSF, is the TF-1 cell line, as described in Kitamura, T. et al. (1989). J Cell Physiol 140, 323-34.

As one of ordinary skill in the art understands, the degree of cellular proliferation is not the only parameter by which neutralizing capacity may be established. For example, measurement of the level of signalling molecules (e.g. cytokines), the level of secretion of which depends on GM-CSF, may be used to identify a suspected GM-CSF neutralizer.

Other examples of cell lines which can be used to determine whether an antibody in question or fragment thereof is a neutralizer of primate GM-CSF activity include AML-193 (Lange, B. et al. (1987). Blood 70, 192-9); GF-D8 (Rambaldi, A. et al. (1993). Blood 81, 1376-83); GM/SO (Oez, S. et al. (1990). Experimental Hematology 18, 1108-11); MOTE (Avanzi, G. C. et al. (1990). Journal of Cellular Physiology 145, 458-64); TALL-103 (Valtieri, M. et al. (1987). Journal of Immunology 138, 4042-50); UT-7 (Komatsu, N. et al. (1991). Cancer Research 51, 341-8).

The human antibody or fragment thereof according to the invention is monoclonal. As used herein, the term "monoclonal" is to be understood as having the meaning typically ascribed to it in the art, namely an antibody (or its corresponding fragment) arising from a single clone of an antibody-producing cell such as a B cell, and recognizing a single epitope on the antigen bound. It is particularly difficult to prepare human antibodies which are monoclonal. In contrast to fusions of murine B cells with immortalized cell lines, fusions of human B cells with immortalized cell lines are not viable. Thus, the human monoclonal antibody of the invention is the result of overcoming significant technical hurdles generally acknowledged to exist in the field of antibody technology. The monoclonal nature of the antibody makes it particularly well suited for use as a therapeutic agent, since such antibody will exist as a single, homogeneous molecular species which can be well-characterized and reproducibly made and purified. These factors result in a product whose biological activity can be predicted with a high level of precision, very important if such a molecule is going to gain regulatory approval for therapeutic administration in humans.

It is especially important that the monoclonal antibody (or corresponding fragment) according to the invention be a human antibody (or corresponding fragment). In contemplating an antibody agent intended for therapeutic administration to humans, it is highly advantageous that this antibody is of human origin. Following administration to a human patient, a human antibody or fragment thereof will most probably not elicit a strong immunogenic response by the patient's immune system, i.e. will not be recognized as being a "foreign", that is non-human protein. This means that no host, i.e. patient antibodies will be generated against the therapeutic antibody which would otherwise block the therapeutic antibody's activity and/or accelerate the therapeutic antibody's elimination from the body of the patient, thus preventing it from exerting its desired therapeutic effect.

The term "human" antibody as used herein is to be understood as meaning that the antibody of the invention, or its fragment, comprises (an) amino acid sequence(s) contained in the human germline antibody repertoire. For the purposes of definition herein, an antibody, or its fragment, may therefore be considered human if it consists of such (a) human germline amino acid sequence(s), i.e. if the amino acid sequence(s) of the antibody in question or fragment thereof is (are) identical to (an) expressed human germline amino acid sequence(s). An antibody or fragment thereof may also be regarded as human if it consists of (a) sequence(s) that deviate(s) from its (their) closest human germline sequence(s) by no more than would be expected due to the imprint of somatic hypermutation. Additionally, the antibodies of many non-human mammals, for example rodents such as mice and rats, comprise VH CDR3 amino acid sequences which one may expect to exist in the expressed human antibody repertoire as well. Any such sequence(s) of human or non-human origin which may be expected to exist in the expressed human repertoire would also be considered "human" for the purposes of the present invention.

According to one embodiment of the invention, the primate GM-CSF is human (*Homo sapiens*) GM-CSF or non-human primate GM-CSF. Especially preferred variants of non-human primate GM-CSF include gibbon monkey (*nomascus concolor*, also known as the western black crested gibbon) GM-CSF and GM-CSF of monkeys of the macaca family, for example rhesus monkey (*Macaca mulatta*) GM-CSF and cynomolgous monkey (*Macaca fascicularis*) GM-CSF. According to this embodiment of the invention, the human monoclonal antibody or fragment thereof exhibits cross reactivity between both human and at least one of the monkey species mentioned above. This is especially advantageous for an antibody molecule which is intended for therapeutic administration in human subjects, since such an antibody will normally have to proceed through a multitude of tests prior to regulatory approval, of which certain early tests involve non-human animal species. In performing such tests, it is generally desirable to use as a non-human species a species bearing a high degree of genetic similarity to humans, since the results so obtained will generally be highly predictive of corresponding results which may be expected when administering the same molecule to humans. However, such predictive power based on animal tests depends at least partially on the comparability of the molecule, and is very high when, due to a cross-species reactivity, the same therapeutic molecule may be administered to humans and animal models. As in this embodiment of the invention, when an antibody molecule is cross reactive for the same antigen in humans as in another closely related species, tests may be performed using the same antibody molecule in humans as in this closely related species, for example in one of the monkey species mentioned above. This increases both the efficiency of the tests themselves as well as predictive power allowed by such tests regarding the behavior of such antibodies in humans, the ultimate species of interest from a therapeutic standpoint.

According to a further embodiment of the invention, the human monoclonal antibody may be an IgG antibody. As is well known in the art, an IgG comprises not only the variable antibody regions responsible for the highly discriminative antigen recognition and binding, but also the constant regions of the heavy and light antibody polypeptide chains normally present in endogenously produced antibodies and, in some cases, even decoration at one or more sites with carbohydrates. Such glycosylation is generally a hallmark of the IgG format, and portions of these constant regions make up the so called Fc region of a full antibody which is known to elicit various effector functions in vivo. In addition, the Fc region mediates binding of IgG to Fc receptor, hence prolonging half life in vivo as well as facilitating homing of the IgG to locations with increased Fc receptor presence—inflamed tissue, for example. Advantageously, the IgG antibody is an IgG1 antibody or an IgG4 antibody, formats which are preferred since their mechanism of action in vivo is particularly well understood and characterized. This is especially the case for IgG1 antibodies.

According to a further embodiment of the invention, the fragment of the human monoclonal antibody may be an scFv, a single domain antibody, an Fv, a VHH antibody, a diabody, a tandem diabody, a Fab, a Fab' or a F(ab)2. These formats may generally be divided into two subclasses, namely those which consist of a single polypeptide chain, and those which comprise at least two polypeptide chains. Members of the former subclass include an scFv (comprising one VH region and one VL region joined into a single polypeptide chain via a polypeptide linker); a single domain antibody (comprising a single antibody variable region) such as a VHH antibody (comprising a single VH region). Members of the latter subclass include an Fv (comprising one VH region and one VL region as separate polypeptide chains which are non-covalently associated with one another); a diabody (comprising two non-covalently associated polypeptide chains, each of which comprises two antibody variable regions—normally one VH and one VL per polypeptide chain—the two polypeptide chains being arranged in a head-to-tail conformation so that a bivalent antibody molecule results); a tandem diabody (bispecific single-chain Fv antibodies comprising four covalently linked immunoglobulin variable-VH and VL-regions of two different specificities, forming a homodimer that is twice as large as the diabody described above); a Fab (comprising as one polypeptide chain an entire antibody light chain, itself comprising a VL region and the entire light chain constant region and, as another polypeptide chain, a part of an antibody heavy chain comprising a complete VH region and part of the heavy chain constant region, said two polypeptide chains being intermolecularly connected via an interchain disulfide bond); a Fab' (as a Fab, above, except with additional reduced disulfide bonds comprised on the antibody heavy chain); and a F(ab)2 (comprising two Fab' molecules, each Fab' molecule being linked to the respective other Fab' molecule via interchain disulfide bonds). In general, antibody fragments of the type described hereinabove allow great flexibility in tailoring, for example, the pharmacokinetic properties of an antibody desired for therapeutic administration to the particular exigencies at hand. For example, it may be desirable to reduce the size of the antibody administered in order to increase the degree of tissue penetration when treating tissues known to be poorly vascularized (for example, joints). Under some circumstances, it may also be desirable to increase the rate at which the therapeutic antibody is eliminated from the body, said rate generally being acceleratable by decreasing the size of the antibody administered.

According to a further embodiment of the invention, said human monoclonal antibody or fragment thereof may be present in monovalent monospecific; multivalent monospecific, in particular bivalent monospecific; or multivalent multispecific, in particular bivalent bispecific forms. In general, a multivalent monospecific, in particular bivalent monospecific antibody such as a full human IgG as described hereinabove may bring with it the therapeutic advantage that the neutralization effected by such an antibody is potentiated by avidity effects, i.e. binding by the same antibody to multiple molecules of the same antigen, here primate GM-CSF. Several monovalent monospecific forms of fragments of the antibody of the invention have been described above (for example, an scFv, an Fv, a VHH or a single domain antibody). Multivalent multispecific, in particular bivalent bispecific forms of the human monoclonal anti-primate GM-CSF antibody of the invention may include a full IgG in which one binding arm binds to primate GM-CSF while the other binding arm of which binds to another antigen different from primate GM-CSF. A further multivalent multispecific, in particular bivalent bispecific form may advantageously be a human single chain bispecific antibody, i.e. a recombinant human antibody construct comprising two scFv entities as described above, connected into one contiguous polypeptide chain by a short interposed polypeptide spacer as generally known in the art (see for example WO 99/54440 for an anti-CD19 x anti-CD3 bispecific single chain antibody). Here, one scFv portion of the bispecific single chain antibody comprised within the bispecific single chain antibody will specifically bind primate GM-CSF as set out above, while the respective other scFv portion of this bispecific single chain antibody will bind another antigen determined to be of therapeutic benefit.

According to a further embodiment the human monoclonal antibody or fragment thereof may be derivatized, for example with an organic polymer, for example with one or more molecules of polyethylene glycol ("PEG") and/or polyvinyl pyrrolidone ("PVP"). As is known in the art, such derivatization can be advantageous in modulating the pharmacodynamic properties of antibodies or fragments thereof. Especially preferred are PEG molecules derivatized as PEG-maleimide, enabling conjugation with the antibody or fragment thereof in a site-specific manner via the sulfhydryl group of a cysteine amino acid. Of these, especially preferred are 20 kD and/or 40 kD PEG-maleimide, in either branched or straight-chain form. It may be especially advantageous to increase the effective molecular weight of smaller human anti-primate GM-CSF antibody fragments such as scFv fragments by coupling the latter to one or more molecules of PEG, especially PEG-maleimide.

According to a further embodiment of the invention, the human monoclonal antibody or fragment thereof specifically binds to an epitope, in particular to a discontinuous epitope, of human or non-human primate GM-CSF comprising amino acids 23-27 (RRLLN) and/or amino acids 65-77 (GLR/QGSLTKLKGPL).

The variability at position 67 within the amino acid sequence stretch 65-77 depicted above reflects the heterogeneity in this portion of primate GM-CSF between, on the one hand, human and gibbon GM-CSF (in which position 67 is R) and, on the other hand, monkeys of the macaca family, for example cynomolgous and rhesus monkeys (in which position 67 is Q).

As used herein, the numbering of human and non-human primate GM-CSF refers to that of mature GM-CSF, i.e. GM-CSF without its 17 amino acid signal sequence (the total length of mature GM-CSF in both human and non-human primate species described above is 127 amino acids). The sequence of human GM-CSF and gibbon GM-CSF is as follows:

```
APARSPSPST QPWEHVNAIQ EARRLLNLSR DTAAEMNETV

EVISEMFDLQ EPTCLQTRLE LYKQGLRGSL TKLKGPLTMM

ASHYKQHCPP TPETSCATQI ITFESFKENL KDFLLVIPFD

CWEPVQE
```

The sequence of GM-CSF in certain members of the macaca monkey family such as for example rhesus monkey and cynomolgous monkey is as follows:

```
APARSPSPGT QPWEHVNAIQ EARRLLNLSR DTAAEMNKTV

EVVSEMFDLQ EPSCLQTRLE LYKQGLQGSL TKLKGPLTMM

ASHYKQHCPP TPETSCATQI ITFQSFKENL KDFLLVIPFD

CWEPVQE
```

The minimum epitope, advantageously a discontinuous epitope, bound by the human monoclonal antibody of the invention (or fragment thereof) as described above is indicated in the above GM-CSF sequence in boldface. As used herein, the term "discontinuous epitope" is to be understood as at least two non-adjacent amino acid sequence stretches within a given polypeptide chain, here mature human and non-human primate GM-CSF, which are simultaneously and specifically (as defined above) bound by an antibody. According to this definition, such simultaneous specific binding may be of the GM-CSF polypeptide in linear form. Here, one may imagine the mature GM-CSF polypeptide forming an extended loop, in one region of which the two sequences indicated in boldface above line up, for example more or less in parallel and in proximity of one another. In this state they are specifically and simultaneously bound by the antibody fragment of the invention. According to this definition, simultaneous specific binding of the two sequence stretches of mature GM-CSF indicated above may also take the form of antibody binding to a conformational epitope. Here, mature GM-CSF has already formed its tertiary conformation as it normally exists in vivo (Sun, H. W., J. Bernhagen, et al. (1996). Proc Natl Acad Sci USA 93, 5191-6). In this tertiary conformation, the polypeptide chain of mature GM-CSF is folded in such a manner as to bring the two sequence stretches indicated above into spatial proximity, for example on the outer surface of a particular region of mature, folded GM-CSF, where they are then recognized by virtue of their three-dimensional conformation in the context of the surrounding polypeptide sequences.

In a preferred embodiment, the above (discontinuous) epitope further comprises amino acids 28-31 (LSRD), italicized in the above sequences of human and non-human primate GM-CSF. In an especially preferred embodiment, either of the above (discontinuous) epitopes further comprises amino acids 32-33 (TA) and/or amino acids 21-22 (EA), each of which stretch is underlined in the above sequences of human and non-human primate GM-CSF.

According to a further embodiment of the invention, the human monoclonal antibody or fragment thereof comprises in its heavy chain variable region a CDR3 comprising an amino acid sequence chosen from the group consisting of those set out in any of the SEQ ID NOs: 1-13 or 56. Preferred is a human monoclonal antibody or fragment thereof comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 1; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 2; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 3; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 4; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 5; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 6; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 7; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 8; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 9; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 10; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 11; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 12; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 13; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 56.

Still more preferred, any of the above 14 combinations of CDR1, CDR2 and CDR3 sequences exists in a human monoclonal antibody or fragment thereof further comprising in its light chain variable region a CDR1 comprising the amino acid sequence set out in SEQ ID NO: 16, a CDR2 comprising the amino acid sequence set out in SEQ ID NO: 17, and a CDR3 comprising the amino acid sequence set out in SEQ ID NO: 18.

According to a further embodiment, the human monoclonal antibody of the invention or fragment thereof comprises in its light chain variable region an amino acid sequence as set out in SEQ ID NO. 19. Preferred is a human monoclonal antibody or fragment thereof, the light chain variable region comprising an amino acid sequence as set out in SEQ ID NO. 19 and a heavy chain variable region comprising an amino acid sequence as set out in SEQ ID NO: 20; or a human monoclonal antibody or fragment thereof, the light chain variable region comprising an amino acid sequence as set out in SEQ ID NO. 19 and a heavy chain variable region comprising an amino acid sequence as set out in SEQ ID NO: 21; or a human monoclonal antibody or fragment thereof, the light chain variable region comprising an amino acid sequence as set out in SEQ ID NO. 19 and a heavy chain variable region comprising an amino acid sequence as set out in SEQ ID NO: 22; or a human monoclonal antibody or fragment thereof, the light chain variable region comprising an amino acid sequence as set out in SEQ ID NO. 19 and a heavy chain variable region comprising an amino acid sequence as set out in SEQ ID NO: 23; or a human monoclonal antibody or fragment thereof, the light chain variable region comprising an amino acid sequence as set out in SEQ ID NO. 19 and a heavy chain variable region comprising an amino acid sequence as set out in SEQ ID NO: 24; or a human monoclonal antibody or fragment thereof, the light chain variable region comprising an amino acid sequence as set out in SEQ ID NO. 19 and a heavy chain variable region comprising an amino acid sequence as set out in SEQ ID NO: 25; or a human monoclonal antibody or fragment thereof, the light chain variable region comprising an amino acid sequence as set out in SEQ ID NO. 19 and a heavy chain variable region comprising an amino acid sequence as set out in SEQ ID NO: 26; or a human monoclonal antibody or fragment thereof, the light chain variable region comprising an amino acid sequence as set out in SEQ ID NO. 19 and a heavy chain variable region comprising an amino acid sequence as set out in SEQ ID NO: 27; or a human monoclonal antibody or fragment thereof, the light chain variable region comprising an amino acid sequence as set out in SEQ ID NO. 19 and a heavy chain variable region comprising an amino acid sequence as set out in SEQ ID NO: 28; or a human monoclonal antibody or fragment thereof, the light chain variable region comprising an amino acid sequence as set out in SEQ ID NO. 19 and a heavy chain variable region comprising an amino acid sequence as set out in SEQ ID NO: 29; or a human monoclonal antibody or fragment thereof, the light chain variable region comprising an amino acid sequence as set out in SEQ ID NO. 19 and a heavy chain variable region comprising an amino acid sequence as set out in SEQ ID NO: 30; or a human monoclonal antibody or fragment thereof, the light chain variable region comprising an amino acid sequence as set out in SEQ ID NO. 19 and a heavy chain variable region comprising an amino acid sequence as set out in SEQ ID NO: 31; or a human monoclonal antibody or fragment thereof, the light chain variable region comprising an amino acid sequence as set out in SEQ ID NO. 19 and a heavy chain variable region comprising an amino acid sequence as set out in SEQ ID NO: 32; or a human monoclonal antibody or fragment thereof, the light chain variable region comprising an amino acid sequence as set out in SEQ ID NO. 19 and a heavy chain variable region comprising an amino acid sequence as set out in SEQ ID NO: 33; or a human monoclonal antibody or fragment thereof, the light chain variable region comprising an amino acid sequence as set out in SEQ ID NO. 19 and a heavy chain variable region comprising an amino acid sequence as set out in SEQ ID NO: 52; or a human monoclonal antibody or fragment thereof, the light chain variable region comprising an amino acid sequence as set out in SEQ ID NO. 19 and a heavy chain variable region comprising an amino acid sequence as set out in SEQ ID NO: 53.

According to a further embodiment, the human monoclonal antibody of the invention or fragment thereof comprises in its light chain variable region an amino acid sequence as set out in SEQ ID NO. 54. Preferred is a human monoclonal antibody or fragment thereof, the light chain variable region comprising an amino acid sequence as set out in SEQ ID NO. 54 and a heavy chain variable region comprising an amino acid sequence as set out in SEQ ID NO: 20; or a human monoclonal antibody or fragment thereof, the light chain variable region comprising an amino acid sequence as set out in SEQ ID NO. 54 and a heavy chain variable region comprising an amino acid sequence as set out in SEQ ID NO: 21; or a human monoclonal antibody or fragment thereof, the light chain variable region comprising an amino acid sequence as set out in SEQ ID NO. 54 and a heavy chain variable region comprising an amino acid sequence as set out in SEQ ID NO: 22; or a human monoclonal antibody or fragment thereof, the light chain variable region comprising an amino acid sequence as set out in SEQ ID NO. 54 and a heavy chain variable region comprising an amino acid sequence as set out in SEQ ID NO: 23; or a human monoclonal antibody or fragment thereof, the light chain variable region comprising an amino acid sequence as set out in SEQ ID NO. 54 and a heavy chain variable region comprising an amino acid sequence as set out in SEQ ID NO: 24; or a human monoclonal antibody or fragment thereof, the light chain variable region comprising an amino acid sequence as set out in SEQ ID NO. 54 and a heavy chain variable region comprising an amino acid sequence as set out in SEQ ID NO: 25; or a human monoclonal antibody or fragment thereof, the light chain variable region comprising an amino acid sequence as set out in SEQ ID NO. 54 and a heavy chain variable region comprising an amino acid sequence as set out in SEQ ID NO: 26; or a human monoclonal antibody or fragment thereof, the light chain variable region comprising an amino acid sequence as set out in SEQ ID NO. 54 and a heavy chain variable region comprising an amino acid sequence as set out in SEQ ID NO: 27; or a human monoclonal antibody or fragment thereof, the light chain variable region comprising an amino acid sequence as set out in SEQ ID NO. 54 and a heavy chain variable region comprising an amino acid sequence as set out in SEQ ID NO: 28; or a human monoclonal antibody or fragment thereof, the light chain variable region comprising an amino acid sequence as set out in SEQ ID NO. 54 and a heavy chain variable region comprising an amino acid sequence as set out in SEQ ID NO: 29; or a human monoclonal antibody or fragment thereof, the light chain variable region comprising an amino acid sequence as set out in SEQ ID NO. 54 and a heavy chain variable region comprising an amino acid sequence as set out in SEQ ID NO: 30; or a human monoclonal antibody or fragment thereof, the light chain variable region comprising an amino acid sequence as set out in SEQ ID NO. 54 and a heavy chain variable region comprising an amino acid sequence as set out in SEQ ID NO: 31; or a human monoclonal antibody or fragment thereof, the light chain variable region comprising an amino acid sequence as set out in SEQ ID NO. 54 and a heavy chain variable region comprising an amino acid sequence as set out in SEQ ID NO: 32; or a human monoclonal antibody or fragment thereof, the light chain variable region comprising an amino acid sequence as set out in SEQ ID NO. 54 and a heavy chain variable region comprising an amino acid sequence as set out in SEQ ID NO: 33; or a human monoclonal antibody or fragment thereof, the light chain variable region comprising an amino acid sequence as set out in SEQ ID NO. 54 and a heavy chain variable region comprising an amino acid sequence as set out in SEQ ID NO: 52; or a human monoclonal antibody or fragment thereof, the light chain variable region comprising an amino acid sequence as set out in SEQ ID NO. 54 and a heavy chain variable region comprising an amino acid sequence as set out in SEQ ID NO: 53.

According to a further embodiment, the human monoclonal antibody of the invention or fragment thereof comprises in its light chain variable region an amino acid sequence as set out in SEQ ID NO. 55. Preferred is a human monoclonal antibody or fragment thereof, the light chain variable region comprising an amino acid sequence as set out in SEQ ID NO. 55 and a heavy chain variable region comprising an amino acid sequence as set out in SEQ ID NO: 20; or a human monoclonal antibody or fragment thereof, the light chain variable region comprising an amino acid sequence as set out in SEQ ID NO. 55 and a heavy chain variable region comprising an amino acid sequence as set out in SEQ ID NO: 21; or a human monoclonal antibody or fragment thereof, the light chain variable region comprising an amino acid sequence as set out in SEQ ID NO. 55 and a heavy chain variable region comprising an amino acid sequence as set out in SEQ ID NO: 22; or a human monoclonal antibody or fragment thereof, the light chain variable region comprising an amino acid sequence as set out in SEQ ID NO. 55 and a heavy chain variable region comprising an amino acid sequence as set out in SEQ ID NO: 23; or a human monoclonal antibody or fragment thereof, the light chain variable region comprising an amino acid sequence as set out in SEQ ID NO. 55 and a heavy chain variable region comprising an amino acid sequence as set out in SEQ ID NO: 24; or a human monoclonal antibody or fragment thereof, the light chain variable region comprising an amino acid sequence as set out in SEQ ID NO. 55 and a heavy chain variable region comprising an amino acid sequence as set out in SEQ ID NO: 25; or a human monoclonal antibody or fragment thereof, the light chain variable region comprising an amino acid sequence as set out in SEQ ID NO. 55 and a heavy chain variable region comprising an amino acid sequence as set out in SEQ ID NO: 26; or a human monoclonal antibody or fragment thereof, the light chain variable region comprising an amino acid sequence as set out in SEQ ID NO. 55 and a heavy chain variable region comprising an amino acid sequence as set out in SEQ ID NO: 27; or a human monoclonal antibody or fragment thereof, the light chain variable region comprising an amino acid sequence as set out in SEQ ID NO. 55 and a heavy chain variable region comprising an amino acid sequence as set out in SEQ ID NO: 28; or a human monoclonal antibody or fragment thereof, the light chain variable region comprising an amino acid sequence as set out in SEQ ID NO. 55 and a heavy chain variable region comprising an amino acid sequence as set out in SEQ ID NO: 29; or a human monoclonal antibody or fragment thereof, the light chain variable region comprising an amino acid sequence as set out in SEQ ID NO. 55 and a heavy chain variable region comprising an amino acid sequence as set out in SEQ ID NO: 30; or a human monoclonal antibody or fragment thereof, the light chain variable region comprising an amino acid sequence as set out in SEQ ID NO. 55 and a heavy chain variable region comprising an amino acid sequence as set out in SEQ ID NO: 31; or a human monoclonal antibody or fragment thereof, the light chain variable region comprising an amino acid sequence as set out in SEQ ID NO. 55 and a heavy chain variable region comprising an amino acid sequence as set out in SEQ ID NO: 32; or a human monoclonal antibody or fragment thereof, the light chain variable region comprising an amino acid sequence as set out in SEQ ID NO. 55 and a heavy chain variable region comprising an amino acid sequence as set out in SEQ ID NO: 33; or a human monoclonal antibody or fragment thereof, the light chain variable region comprising an amino acid sequence as set out in SEQ ID NO. 55 and a heavy chain variable region comprising an amino acid sequence as set out in SEQ ID NO: 52; or a human monoclonal antibody or fragment thereof, the light chain variable region comprising an amino acid sequence as set out in SEQ ID NO. 55 and a heavy chain variable region comprising an amino acid sequence as set out in SEQ ID NO: 53.

A preferred embodiment provides a human monoclonal antibody or fragment thereof comprising in its light chain a variable region a CDR1 region comprising an amino acid sequence as set out in SEQ ID NO. 16, a CDR2 region having an amino acid sequence as set out in SEQ ID NO. 17 and a CDR3 having an amino acid sequence as set out in SEQ ID NO. 18 and comprising in its heavy chain variable region a CDR1 region comprising an amino acid sequence as set out in SEQ ID NO. 14, a CDR2 region having an amino acid sequence as set out in SEQ ID NO. 15 and a CDR3 having an amino acid sequence as set out in any of SEQ ID NOs. 1, 2, 3, 4, 5, 6, 7, 8, 9, 10, 11, 12, 13 or 56.

In a further preferred embodiment the human monoclonal antibody comprises in its light chain an amino acid sequence as set out in SEQ ID NO: 34 and in its heavy chain an amino acid sequence as set out in SEQ ID NO: 35; or in its light chain an amino acid sequence as set out in SEQ ID NO: 34 and in its heavy chain an amino acid sequence as set out in SEQ ID NO: 36; or in its light chain an amino acid sequence as set out in SEQ ID NO: 34 and in its heavy chain an amino acid sequence as set out in SEQ ID NO: 37; or in its light chain an amino acid sequence as set out in SEQ ID NO: 34 and in its heavy chain an amino acid sequence as set out in SEQ ID NO: 38; or in its light chain an amino acid sequence as set out in SEQ ID NO: 34 and in its heavy chain an amino acid sequence as set out in SEQ ID NO: 39; or in its light chain an amino acid sequence as set out in SEQ ID NO: 34 and in its heavy chain an amino acid sequence as set out in SEQ ID NO: 40; or in its light chain an amino acid sequence as set out in SEQ ID NO: 34 and in its heavy chain an amino acid sequence as set out in SEQ ID NO: 41; or in its light chain an amino acid sequence as set out in SEQ ID NO: 34 and in its heavy chain an amino acid sequence as set out in SEQ ID NO: 42; or in its light chain an amino acid sequence as set out in SEQ ID NO: 34 and in its heavy chain an amino acid sequence as set out in SEQ ID NO: 43; or in its light chain an amino acid sequence as set out in SEQ ID NO: 34 and in its heavy chain an amino acid sequence as set out in SEQ ID NO: 44; or in its light chain an amino acid sequence as set out in SEQ ID NO: 34 and in its heavy chain an amino acid sequence as set out in SEQ ID NO: 45; or in its light chain an amino acid sequence as set out in SEQ ID NO: 34 and in its heavy chain an amino acid sequence as set out in SEQ ID NO: 46; or in its light chain an amino acid sequence as set out in SEQ ID NO: 34 and in its heavy chain an amino acid sequence as set out in SEQ ID NO: 47; or in its light chain an amino acid sequence as set out in SEQ ID NO: 34 and in its heavy chain an amino acid sequence as set out in SEQ ID NO: 48.

The preferred embodiments above provide human monoclonal antibody molecules and/or fragments thereof which are especially advantageous as neutralizers of the activity of primate, especially of human GM-CSF. Human monoclonal antibodies or fragments thereof according to these especially preferred embodiments are highly advantageous for several reasons.

First, they recognize primate GM-CSF highly specifically, that is to say that from a mixture of primate GM-CSF with other primate colony stimulating factors (for example primate G-CSF and M-CSF), the binding molecules according to these especially preferred embodiments are highly discriminating for primate GM-CSF, whereas the other colony stimulating factors in the same milieu are not recognized. This means that a human monoclonal antibody or fragment thereof according to these embodiments, when administered to a human, will be expected to specifically bind to and neutralize only the desired target, whereas other undesired targets are neither bound nor neutralized. Ultimately, this leads to a high degree of predictability concerning the therapeutic mode of action in vivo.

Second, binders according to these especially preferred embodiments bind to primate GM-CSF with extremely high affinity. $K_D$ values of from about $4\times10^{-9}$ M down to as low as about $0.04\times10^{-9}$ M, the latter corresponding to about 40 pM, have been observed for molecules of this class. Since the kinetic on-rate of such molecules in aqueous media is largely diffusion controlled and therefore cannot be improved beyond what the local diffusion conditions will allow under physiological conditions, the low $K_D$ arises primarily as a result of the kinetic off-rate, $k_{off}$, which for the highest affinity antibody binder is approximately $10^{-5}$ $s^{-1}$. This means that once the complex between a human monoclonal antibody or fragment thereof according to any of these embodiments of the invention on the one hand and primate GM-CSF on the other hand is formed, it does not readily, or at least does not quickly separate. For binding molecules intended as neutralizers of biological activity, these characteristics are highly advantageous since the desirable neutralizing effect will normally last only as long as the molecule, the biological activity of which is to be neutralized (here primate GM-CSF) remains bound by the neutralizing binding molecule. So a neutralizing molecule which remains bound to its intended target for a long time will continue to neutralize for a correspondingly long time.

The high binding affinity of human monoclonal antibodies or fragments thereof to primate GM-CSF has an additional advantage. Normally, antibodies or fragments thereof will be eliminated from the bloodstream of a patient in a size-dependent fashion, with smaller molecules being excreted and eliminated before larger ones. Since the complex of the two polypeptides—antibody or antibody fragment and bound GM-CSF—is obviously larger than the antibody alone, the low $k_{off}$ mentioned above has the effect that therapeutic neutralizer is excreted and eliminated from the patient's body more slowly than would be the case, were it not bound to GM-CSF. Thus, not only the magnitude of the neutralizing activity but also its duration in vivo is increased.

Finally, the neutralizing activity determined for binders according to these especially preferred embodiments is surprisingly high. As will be described in more detail herein below, neutralizing activity was measured in vitro using a TF-1 growth inhibition assay (Kitamura, T. et al. (1989). J Cell Physiol 140, 323-34). As an indication of neutralizing potential, $IC_{50}$ values were measured, $IC_{50}$ representing the concentration of human monoclonal antibody or fragment thereof according to any of these embodiments of the invention required to elicit a half-maximal inhibition of TF-1 cell proliferation. For human monoclonal antibodies or fragments thereof according to any of these embodiments of the invention an $IC_{50}$ value of approximately $3\times10^{-10}$ M, or about 0.3 nM was determined The binding molecules according to any of these embodiments of the invention are therefore highly potent neutralizers of the activity of primate GM-CSF.

In summary, then, a human monoclonal antibody or fragment thereof according to any of the above embodiments of the invention exhibits high degree of discrimination for the desired antigen, binds this antigen extremely tightly and for a long time and exhibits highly potent neutralizing activity for the long time it remains bound. At the same time, the long persistence of the binder-antigen complex slows elimination of this binder from the body, thereby lengthening the duration of the desired therapeutic effect in vivo.

A further aspect of the invention provides a human monoclonal antibody or fragment thereof comprising an amino acid sequence having at least 70% homology with an amino acid as set out in any of SEQ ID NOs: 1-48 and/or 52-56. Homology may be determined by standard sequence alignment programs such as Vector NTI (InforMax™, Maryland, USA). Such programs compare aligned sequences on an amino acid-by-amino acid basis, and can be set to various levels of stringency for the comparison (e.g. identical amino acid, conservative amino acid substitution, etc.). As the term is used herein, two amino acids in question are considered as being "conservative substitutions" of one another if they each belong to the same chemical class, i.e. acidic, nonpolar, uncharged polar and basic. By way of non-limiting example, two different amino acids belonging to the class of nonpolar amino acids would be considered "conservative substitutions" of one another, even if these two amino acids were not identical, whereas a nonpolar amino acid on the one hand and a basic amino acid on the other hand would not be considered "conservative substitutions" of one another. Panel 3.1 of "Molecular Biology of the Cell", $4^{th}$ Edition (2002), by Alberts, Johnson, Lewis, Raff, Roberts and Walter groups amino acids into four main groups: acidic, nonpolar, uncharged polar and basic. Such a grouping may be used for the purposes of determining, for the purposes of the present invention, whether or not a particular amino acid is a conservative substitution of another amino acid in question.

A further aspect of the invention provides a polynucleotide molecule having a nucleotide sequence encoding an amino acid sequence as set out in any of SEQ ID NOs: 1-48 and/or 52 to 56 or a nucleotide sequence exhibiting at least 70% homology therewith, wherein homology may be determined by comparing a nucleotide sequence encoding an amino acid sequence of any of SEQ ID NOs: 1-48 and/or 52-56 with a nucleotide sequence in question by sequence alignment (as described above for amino acid sequences), wherein a nucleotide in the sequence in question is considered homologous if it is either identical to the corresponding nucleotide in the nucleotide sequence encoding a corresponding amino acid sequence of any of SEQ ID NOs: 1-48 and/or 52-56 or if one or more nucleotide deviation(s) in the sequence in question from the corresponding one or more nucleotide(s) in the nucleotide sequence encoding an amino acid sequence of any of SEQ ID NOs: 1-48 and/or 52-56 results in a nucleotide triplet which, when translated, results in an amino acid which is either identical to (due to a degenerate triplet) or a conservative substitution of the corresponding amino acid in the corresponding amino acid sequence of any of SEQ ID NOs: 1-48 and/or 52-56. Here, the term "conservative substitution" is to be understood as described above.

A further aspect of the invention provides a pharmaceutical composition comprising a human monoclonal antibody or fragment thereof or a polynucleotide molecule having a nucleotide sequence encoding an amino acid sequence as set out in any of SEQ ID NOs: 1-48 and/or 52-56 or encoding an amino acid sequence comprising an amino acid sequence bearing at least 70% homology to any of SEQ ID NOs: 1-48 and/or 52-56, wherein "homology" is to be understood as explained hereinabove. In accordance with this invention, the term "pharmaceutical composition" relates to a composition for administration to a patient, preferably a human patient. In a preferred embodiment, the pharmaceutical composition comprises a composition for parenteral, transdermal, intraluminal, intraarterial, intrathecal and/or intranasal administration or by direct injection into tissue. It is in particular envisaged that said pharmaceutical composition is administered to a patient via infusion or injection. Administration of the suitable compositions may be effected by different ways, e.g., by intravenous, intraperitoneal, subcutaneous, intramuscular, topical or intradermal administration. The pharmaceutical composition of the present invention may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, liposomes, etc. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, inert gases and the like. In addition, the pharmaceutical composition of the present invention might comprise proteinaceous carriers, like, e.g., serum albumin or immunoglobulin, preferably of human origin. It is envisaged that the pharmaceutical composition of the invention might comprise, in addition to the human monoclonal antibody or fragment thereof (as described in this invention), further biologically active agents, depending on the intended use of the pharmaceutical composition. Such agents might be drugs acting on the gastro-intestinal system, drugs acting as cytostatica, drugs preventing hyperurikemia, drugs inhibiting immunoreactions (e.g. corticosteroids), drugs modulating the inflammatory response, drugs acting on the circulatory system and/or agents such as cytokines known in the art.

A further aspect of the invention provides a use of a human monoclonal antibody or fragment thereof as described hereinabove or a polynucleotide molecule comprising a nucleotide sequence encoding an amino acid sequence as set out in any of SEQ ID NOs: 1-48 and/or 52-56 or encoding an amino acid sequence comprising an amino acid sequence bearing at least 70% homology to any of SEQ ID NOs: 1-48 and/or 52-56, wherein "homology" is to be understood as explained hereinabove, in the manufacture of a medicament, optionally comprising one or more anti-inflammatory agents, for the treatment of inflammatory diseases. The inflammatory diseases are advantageously chosen from the group consisting of rheumatoid arthritis (RA) (including RA which is resistant to treatment with TNF-alpha neutralizers), asthma, multiple sclerosis (MS), chronic obstructive pulmonary disease (COPD), Acute Respiratory Distress Syndrome (ARDS), Crohn's Disease, Idiopathic Pulmonary Fibrosis (IPF), Inflammatory Bowel Disease (IBD), uveitis, macular degeneration, colitis, psoriasis, Wallerian Degeneration, antiphospholipid syndrome (APS), acute coronary syndrome, restinosis, atherosclerosis, relapsing polychondritis (RP), acute or chronic hepatitis, failed orthopedic implants, glomerulonephritis, lupus or autoimmune disorders.

Of special interest is the use of the human monoclonal antibody or fragment thereof according to the invention for the preparation of a medicament for the treatment of RA (including RA which is resistant to treatment with TNF-alpha neutralizers), asthma, MS and/or Crohn's disease.

With regard to RA, asthma and/or MS, there are two popular theories regarding the pathogenesis of rheumatoid arthritis (RA). The first holds that the T cell, through interaction with an—as yet unidentified—antigen, is the primary cell responsible for initiating the disease as well as for driving the chronic inflammatory process. This theory is based upon the known association of RA with class II major histocompatability antigens, the large number of CD4+ T cells and skewed T cell receptor gene usage in the RA synovium. GM-CSF is known to enhance antigen presenting function though increasing surface class II MHC expression and GM-CSF is produced by T-cells, indicating a putative role for GM-CSF in disease progression according to the T-cell based hypothesis.

The second theory holds that, while T cells may be important in initiating the disease, chronic inflammation is self-perpetuated by macrophages and fibroblasts in a T-cell independent manner. This theory is based upon the relative absence of activated T cells phenotypes in chronic RA and the preponderance of activated macrophage and fibroblast phenotypes. GM-CSF is a potent stimulator of macrophages and promotes proliferation of monocytes and macrophages.

GM-CSF known to be produced primarily by "effector" cells (macrophages) and connective tissue cells (fibroblasts) is expressed in abundance in RA synovium and synovial fluid, as measured by ELISA or mRNA studies. According to the "macrophage-fibroblast theory" of RA, these two cell types appear to be largely responsible for creating a self-perpetuating state of chronic inflammation in which T cell participation may no longer be critical. In this scenario, the activated macrophage continuously secretes IL-1 and TNF which maintain the synovial fibroblast in an activated state. The fibroblast, in turn, secretes large amounts of: a) cytokines—IL6, IL8 and GM-CSF; b) prostaglandins; and c) protease enzymes. GM-CSF feeds back to promote the maturation of newly recruited monocytes to macrophages. IL-8 and IL-6 contribute to the recruitment and/or activation of yet other cell populations, while the prostaglandins and proteases act directly to erode and destroy nearby connective tissues such as bone and cartilage.

With regard to Crohn's disease, recombinant human granulocyte/macrophage colony stimulating factor (rGM-CSF) from yeast has shown efficacy in the treatment of moderate to severe Crohn's disease (Dieckgraefe B K, Korzenik J R (2002). Lancet 360, 1478-80). Several review articles have since then speculated about the therapeutic effect of this potent pro-inflammatory cytokine in this disease, believed to be of an inflammatory nature. Possible explanations for the mode of action of rGM-CSF included an immunodeficiency component in Crohn's Disease, Th 2 skewing, and expansion of dendritic cells promoting differentiation of regulatory T cells (Wilk N.J., Viney J L (2002). Curr Opin Invest Drugs 3, 1291-6; Folwaczny C et al. (2003). Eur J Gastroenterol Hepatol 15, 621-6). The inventors believe that a simpler mode of action, which at the same time is more consistent with the known role of GM-CSF in other pro-inflammatory diseases may be proposed.

GM-CSF is one of the most potent adjuvants known, which is why the cytokine is co-administered in numerous ongoing vaccination trials. At the same time, GM-CSF is highly immunogenic (Ragnhammar P et al. (1994). Blood 84, 4078-87). A very recent study (Rini B et al. (2005) Cytokine 29, 56-66) has shown that daily subcutaneous treatment with rGM-CSF from yeast, as performed in the Crohn's disease trial (Dieckgraefe B K, Korzenik J R (2002). Lancet 360, 1478-80), led within three months in 87% (13/15) of prostate cancer patients, to the development of antibodies against the cytokine. Sixty percent of patients (9/15) developed (polyclonal) GM-CSF neutralizing antibodies. The possibility of a neutralizing response to GM-CSF was not investigated in the Crohn's disease trial, nor were serum levels of GM-CSF determined under therapy. Within the scope of this embodiment of the invention, it is contemplated that Crohn's disease patients treated with rGM-CSF did not directly respond only to the immune-stimulatory activity of the cytokine but also, at least in part, responded clinically to an antibody response neutralizing both the administered as well as the endogenous GM-CSF, which is known to be overproduced in Crohn's disease (Agnholt J et al. (2004) Eur J Gastroenterol Hepatol 16, 649-55). Neutralizing anti-GM-CSF antibodies, then, may have a similar therapeutic activity in Crohn's disease as does rGM-CSF, and should be considered as an alternative therapeutic approach, as is contemplated hereinabove.

A further aspect of the invention provides a use of a human monoclonal antibody or fragment thereof as described hereinabove or a polynucleotide molecule comprising a nucleotide sequence encoding an amino acid sequence as set out in any of SEQ ID NOs: 1-48 and/or 52-56 or encoding an amino acid sequence comprising an amino acid sequence bearing at least 70% homology to any of SEQ ID NOs: 1-48 and/or 52-56, wherein "homology" is to be understood as explained hereinabove in the manufacture of a medicament, optionally comprising one or more additional anti-cancer agents, for the treatment of a tumorous disease or another condition with delayed cell apoptosis, increased cell survival or proliferation. A preferred tumorous disease is a cancer, of which leukaemia, multiple myeloma, gastric carcinoma or skin carcinoma are especially preferred.

Olver et al. ((2002) Cancer Chemother Pharmacol. 50, 171-8) subcutaneously applied the GM-CSF antagonist E21R in patients with solid tumors known to express GM-CSF receptors, leading to only a temporary reduction of the PSA serum levels. Further, the application of this GM-CSF antagonist in acute myeloid leukemia ("AML") did not reveal clinical activity (Jakupovic et al. (2004) Blood 103, 3230-2.). Still further, the application of anti-GM-CSF monoclonal antibodies to AML patients did not reveal an anti-leukemic effect despite sufficient serum levels and biological activity of the antibody in vivo (Bouabdallah et al. (1998) Leuk Lymphoma 30, 539-49). The authors thus concluded that treatment with anti GM-CSF antibodies is not effective in AML patients.

Figure 2:
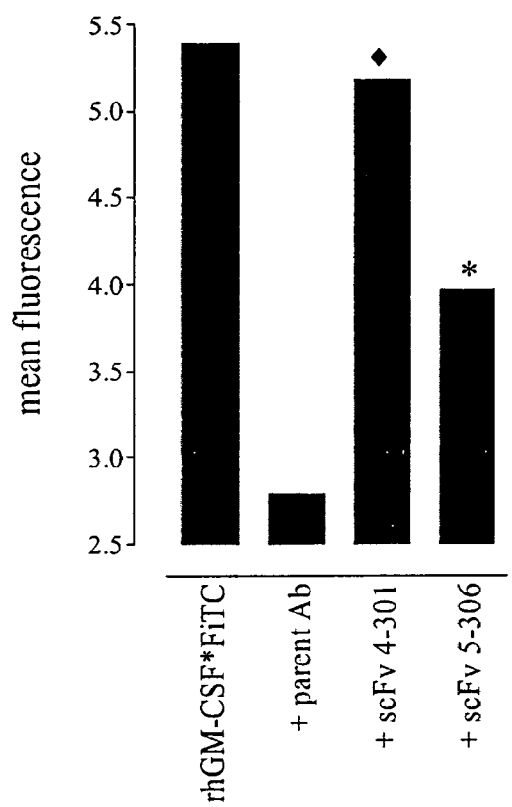
Figure 3:
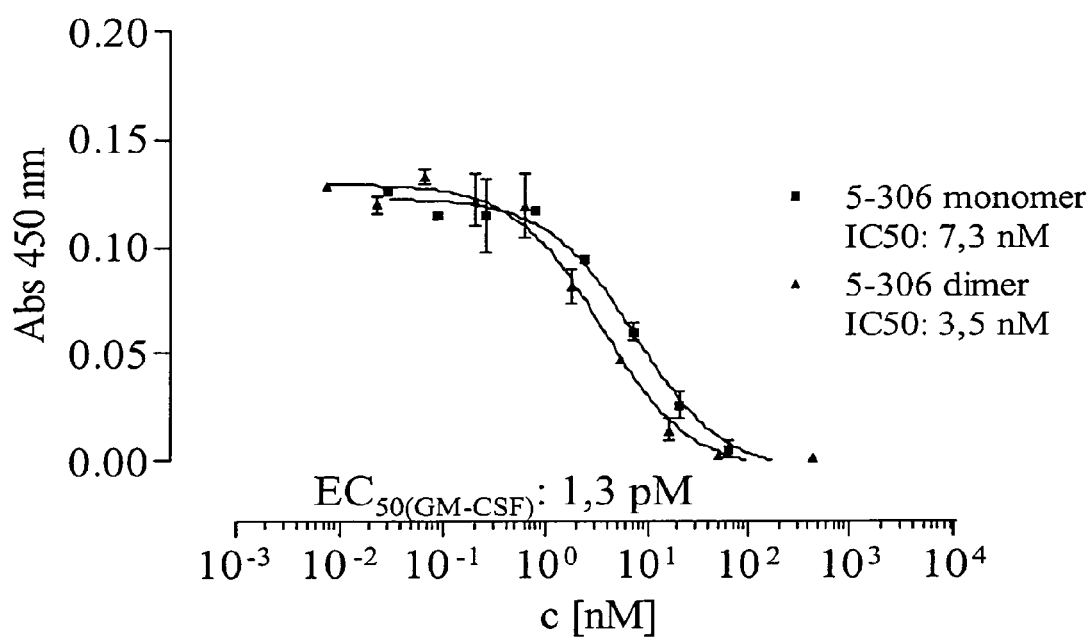

The invention will now be described in more detail in the following non-limiting examples and figures, an overview of which follows:

FIG. 1 Absorption intensity (directly proportional to binding strength) for a variety of anti-rhGM-CSF scFv molecules obtained after four or five rounds of panning in phage display as determined by ELISA FIG. 2 Mean fluorescence intensity (inversely proportional to neutralization strength) for a variety of anti-rhGM-CSF scFv and other test molecules as determined by a flow cytometry-based assay FIG. 3 Results of a TF-1 proliferation inhibition assay performed using the anti-rhGM-CSF scFv molecule 5-306

Figure 4:
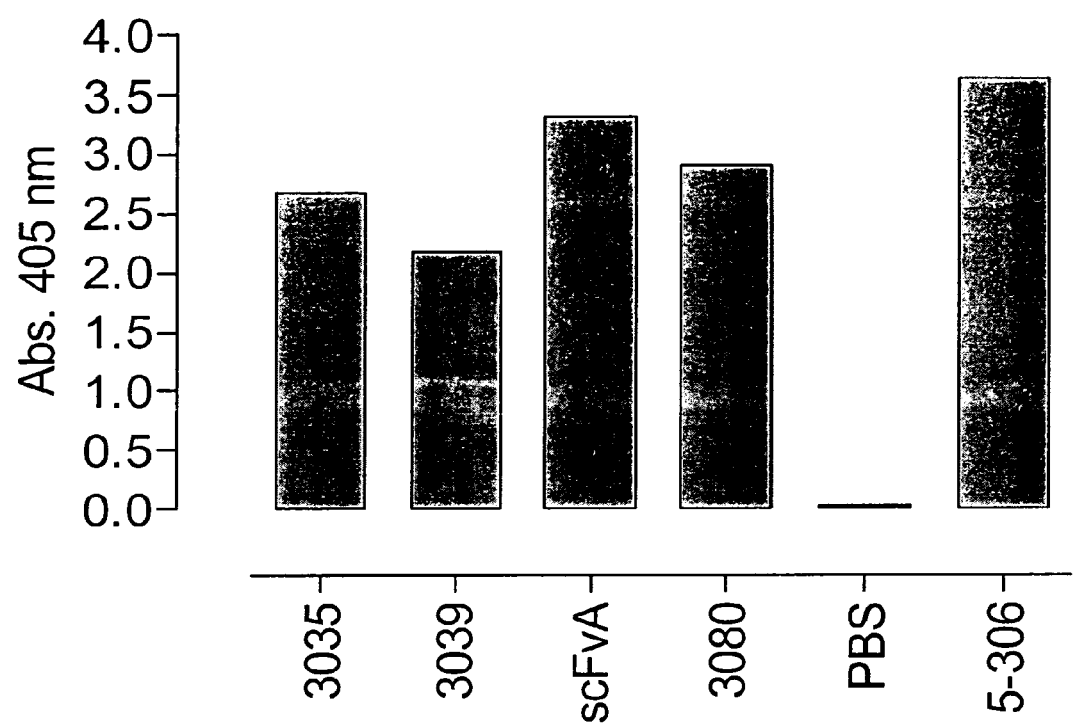
Figure 5:
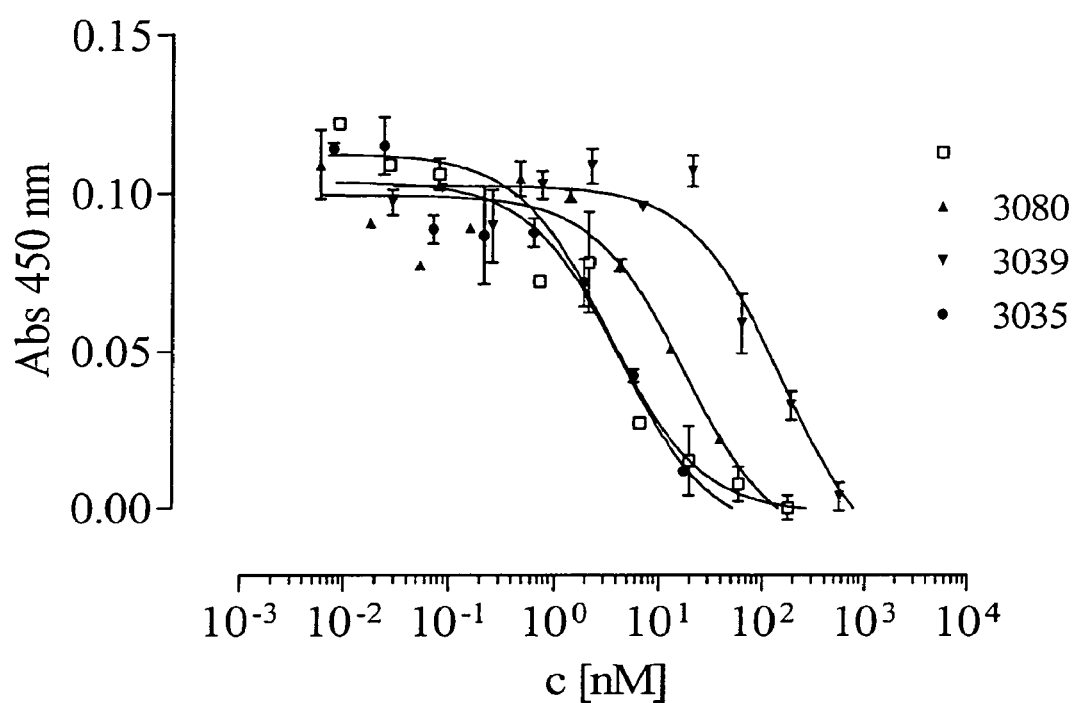
Figure 6:
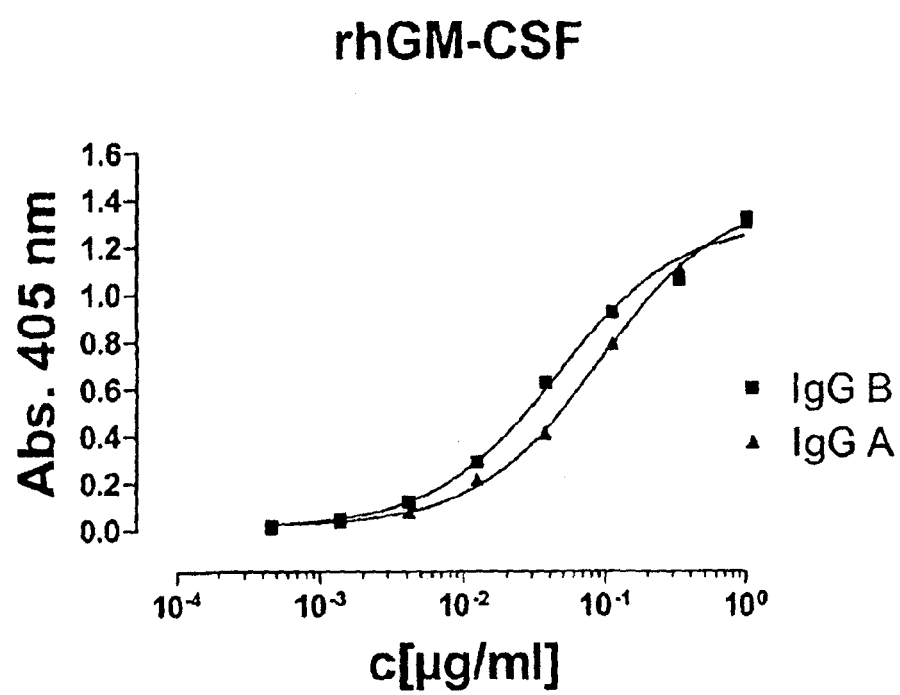
Figure 6:
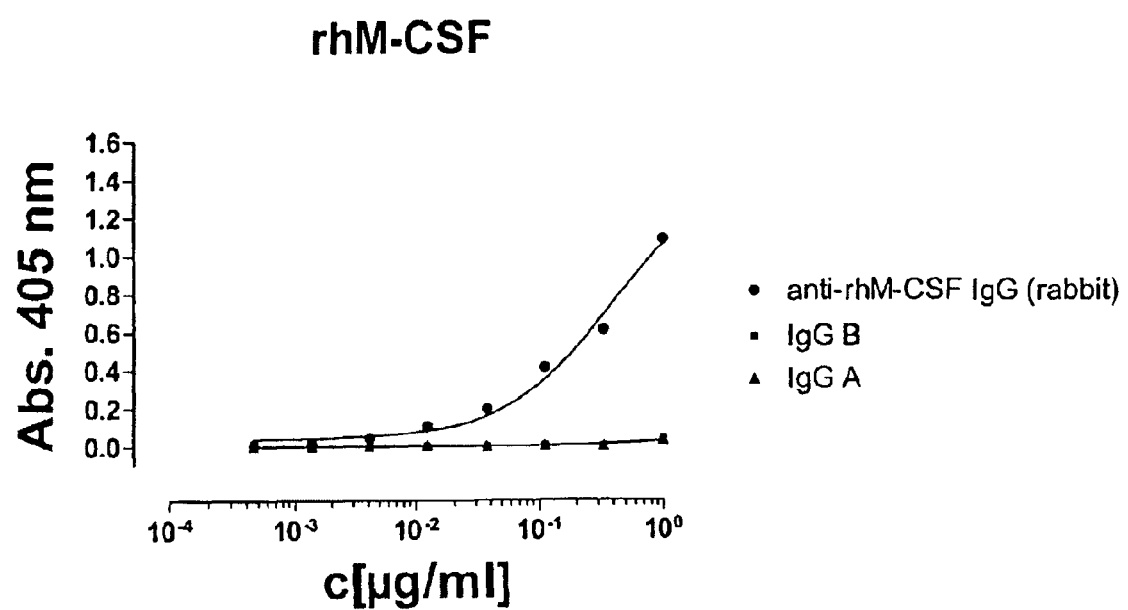
Figure 6:
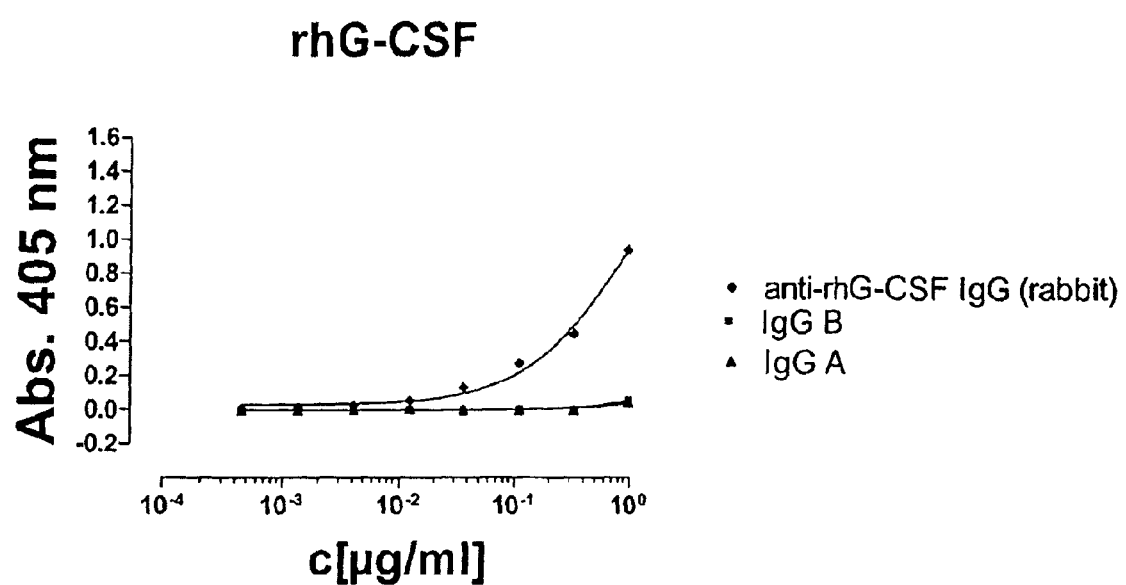

FIG. 4 Absorption intensity (directly proportional to binding strength) for a variety of human anti-rhGM-CSF scFv molecules obtained after four or five rounds of panning in phage display as determined by ELISA FIG. 5 Results of a TF-1 proliferation inhibition assay performed using various representative human anti-rhGM-CSF scFv hits FIG. 6 Binding specificity of human monoclonal antibodies for human GM-CSF and other human colony stimulating factors FIG. 7 Surface plasmon resonance measurements characterizing kinetic binding of human monoclonal anti-GM-CSF antibodies and fragments thereof.

FIG. 8A Sequence alignment of non-human primate GM-CSF and human GM-CSF

Figure 8B:
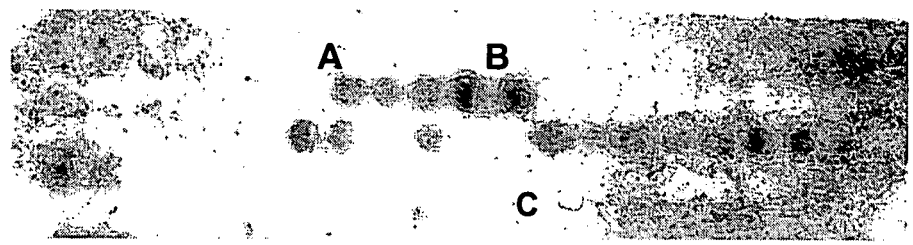
Figure 9:
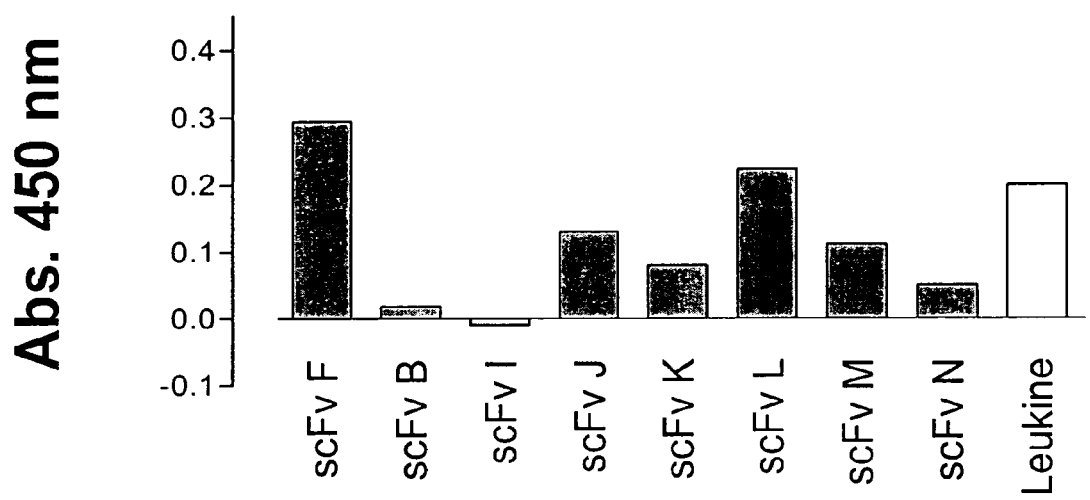
Figure 9:
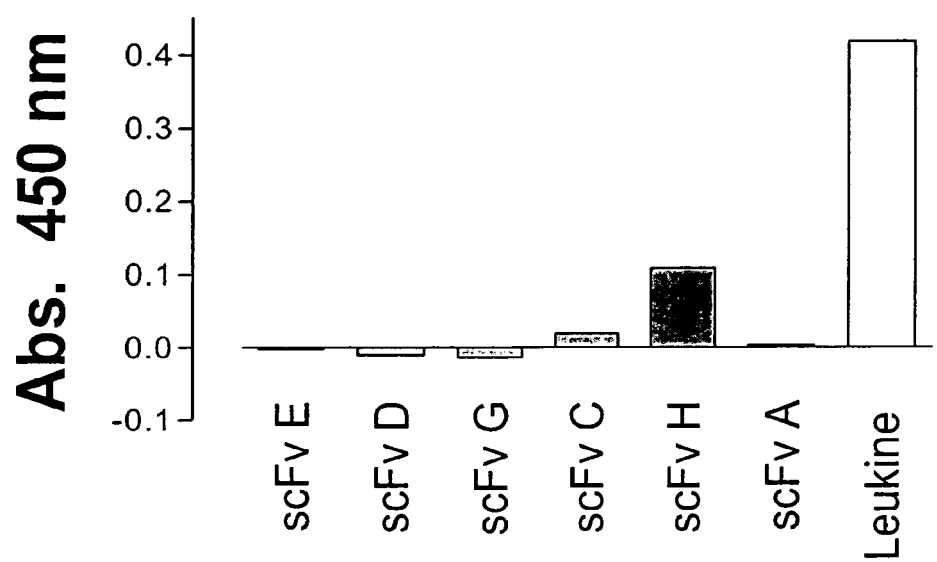
Figure 10:
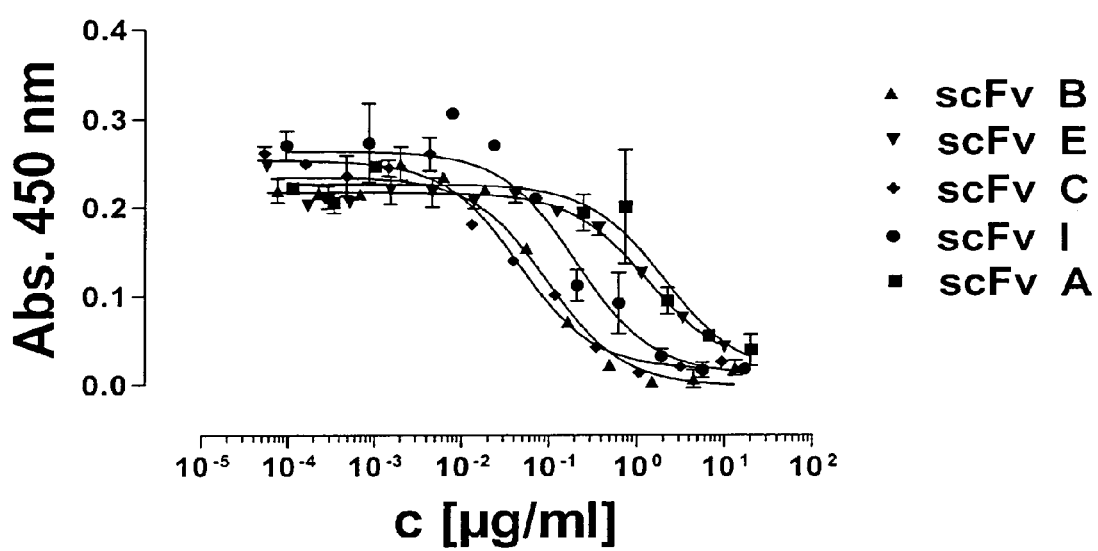
Figure 10:
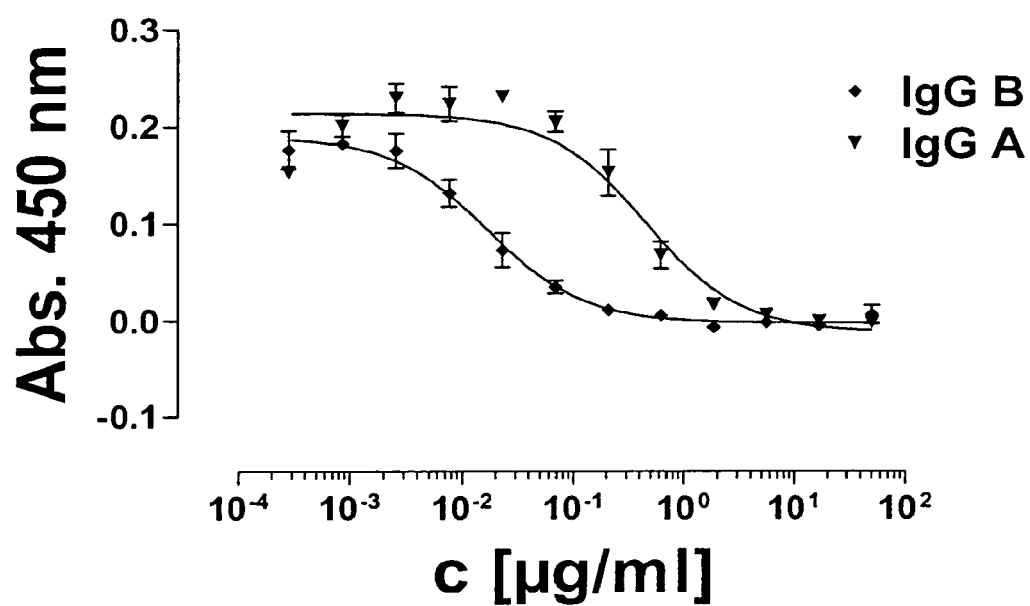
Figure 10:
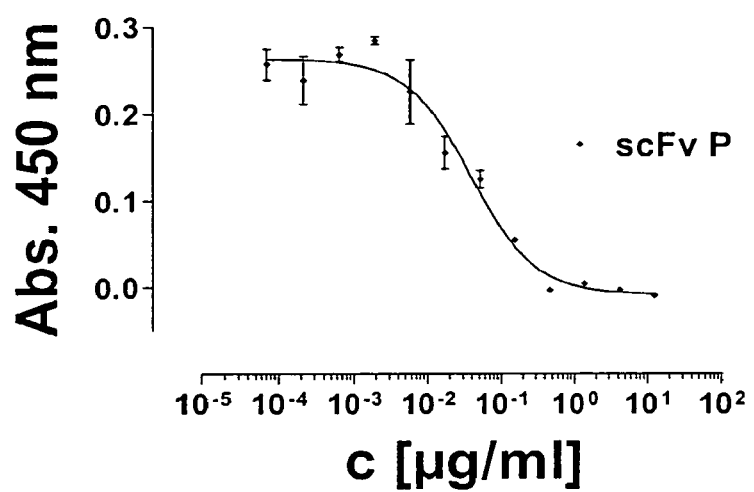
Figure 10:
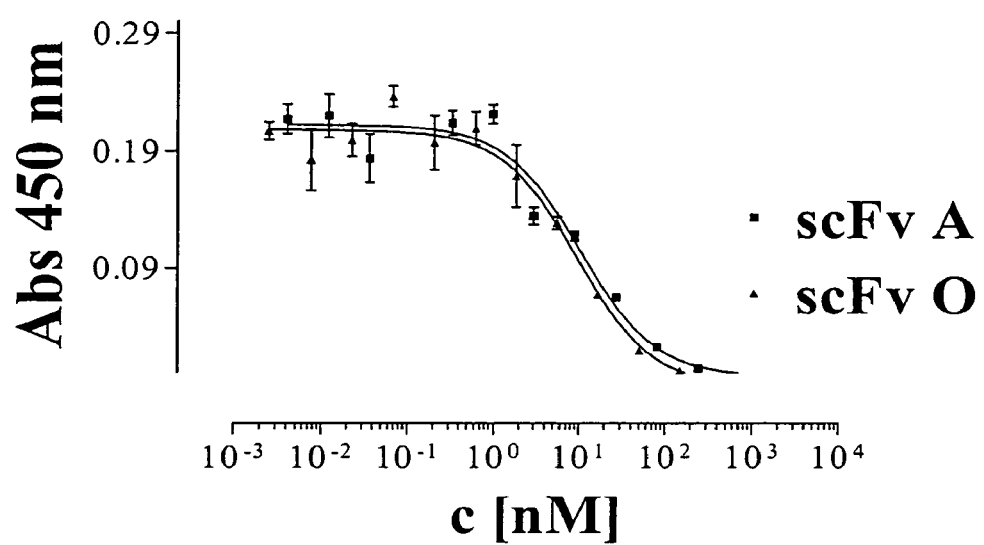
Figure 11:
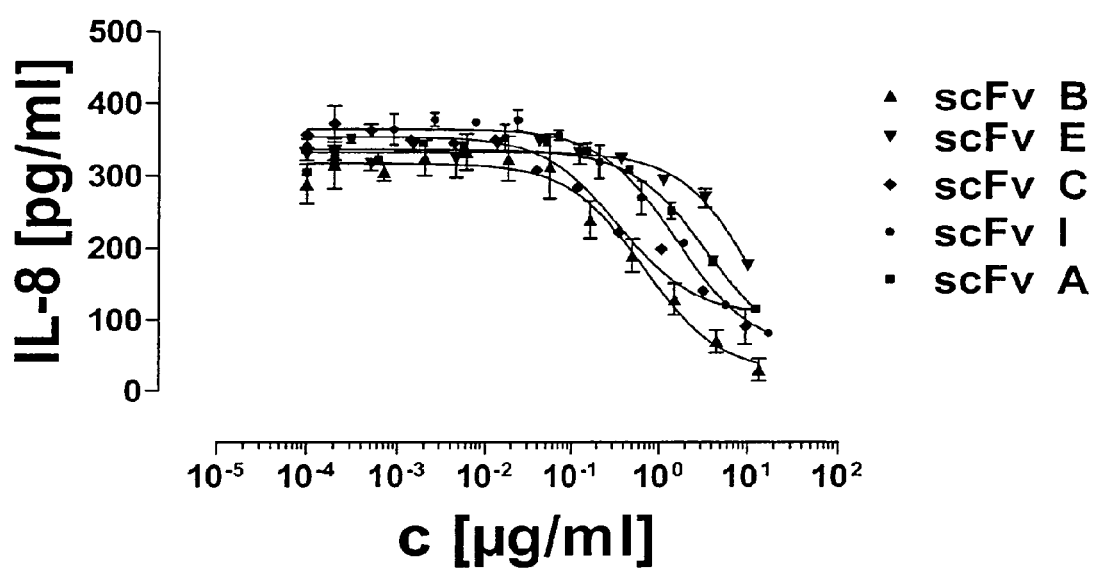
Figure 12:
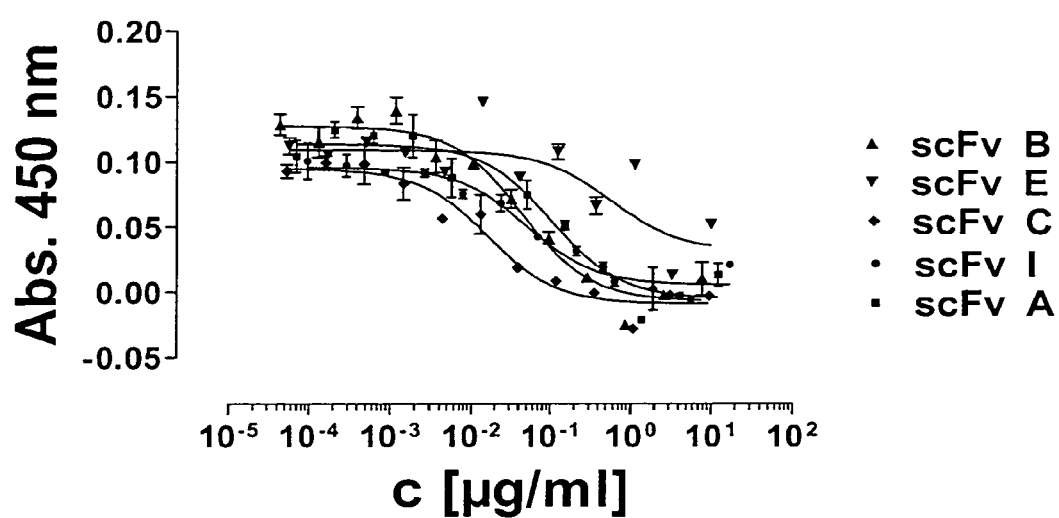
Figure 12:
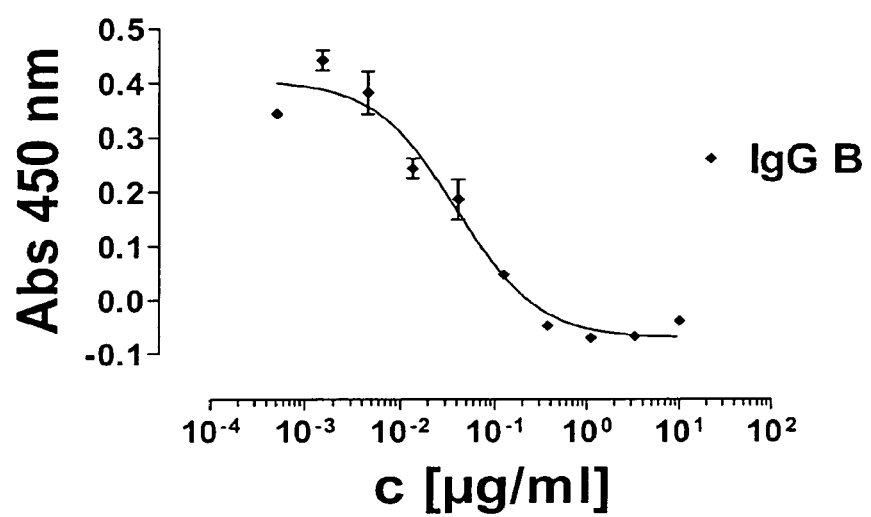
Figure 13:
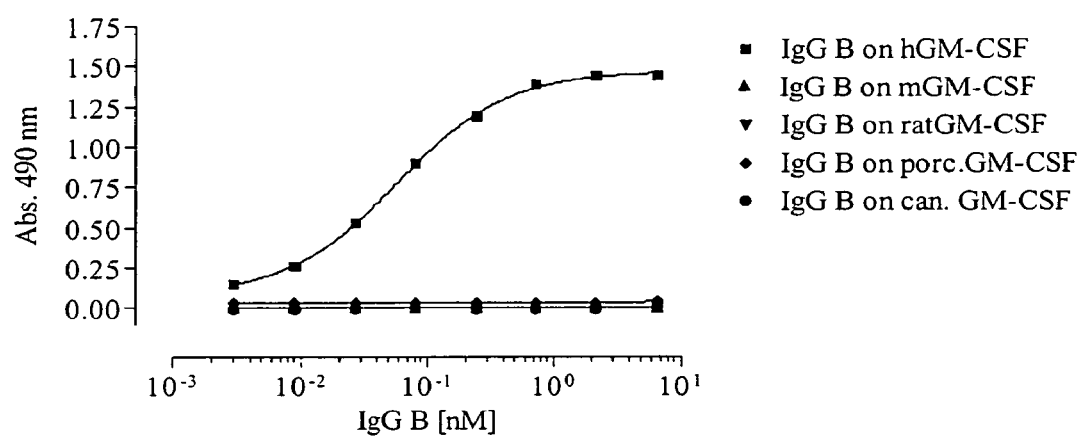
Figure 14:
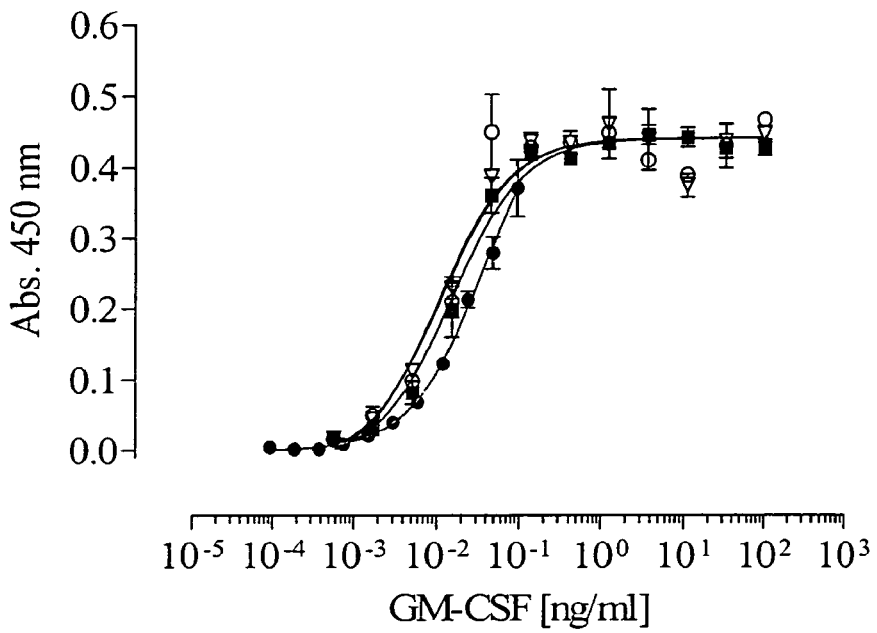
Figure 14:
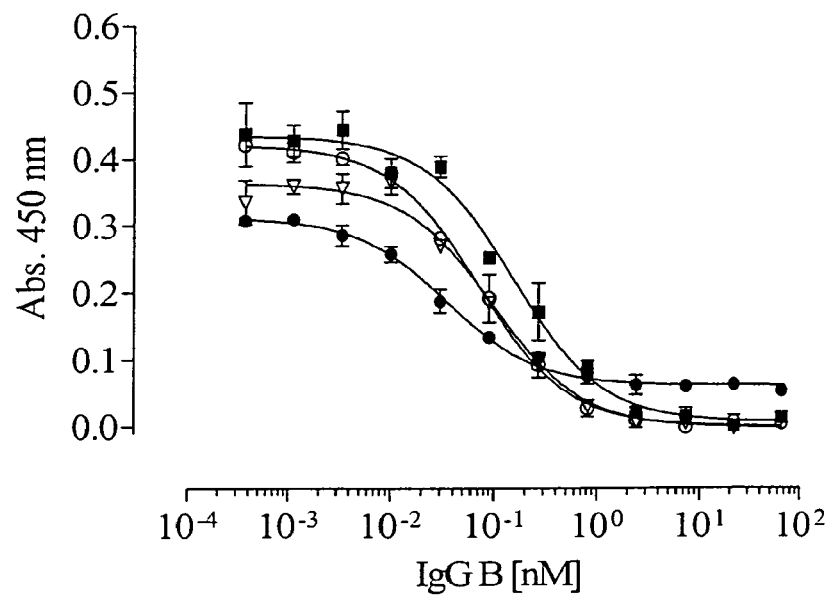
Figure 15:
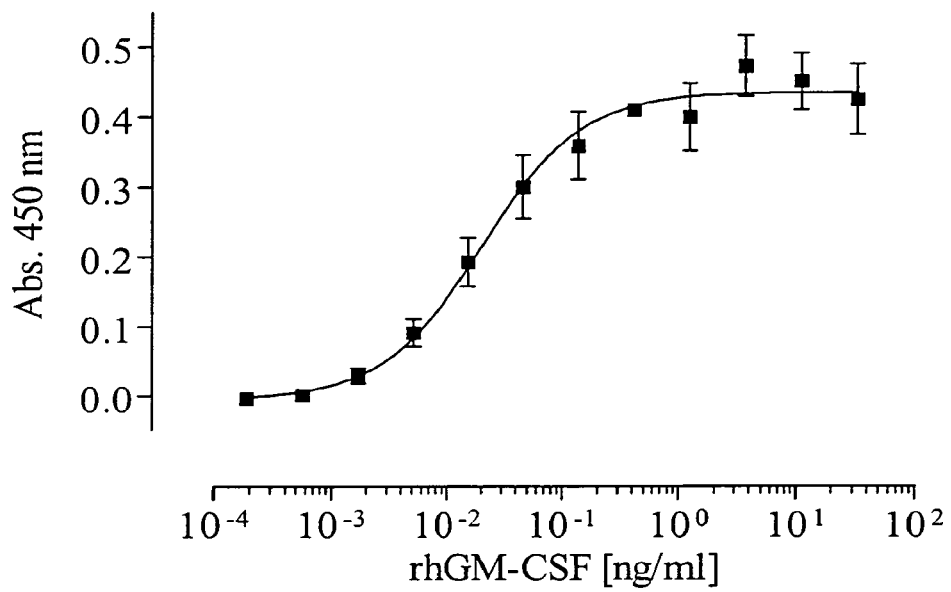
Figure 15:
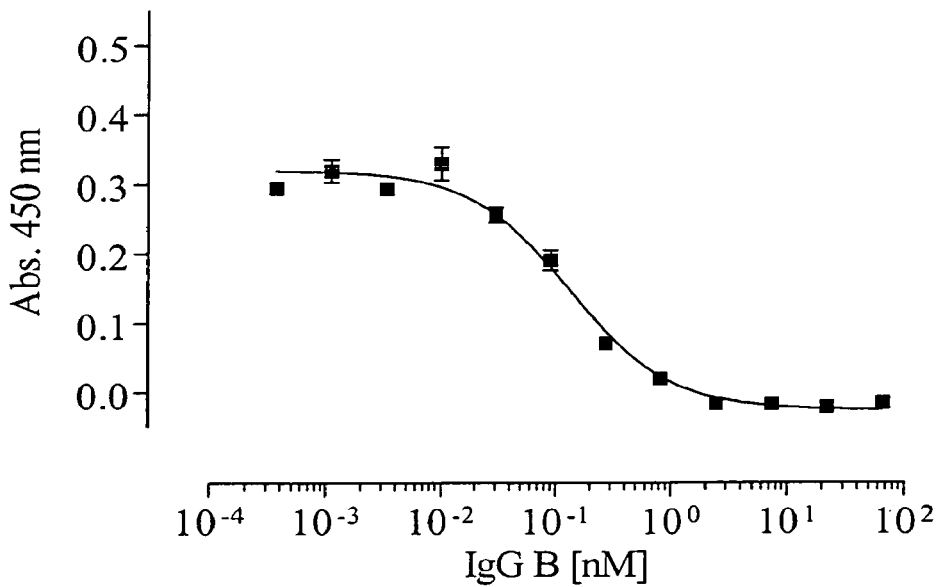
Figure 16:
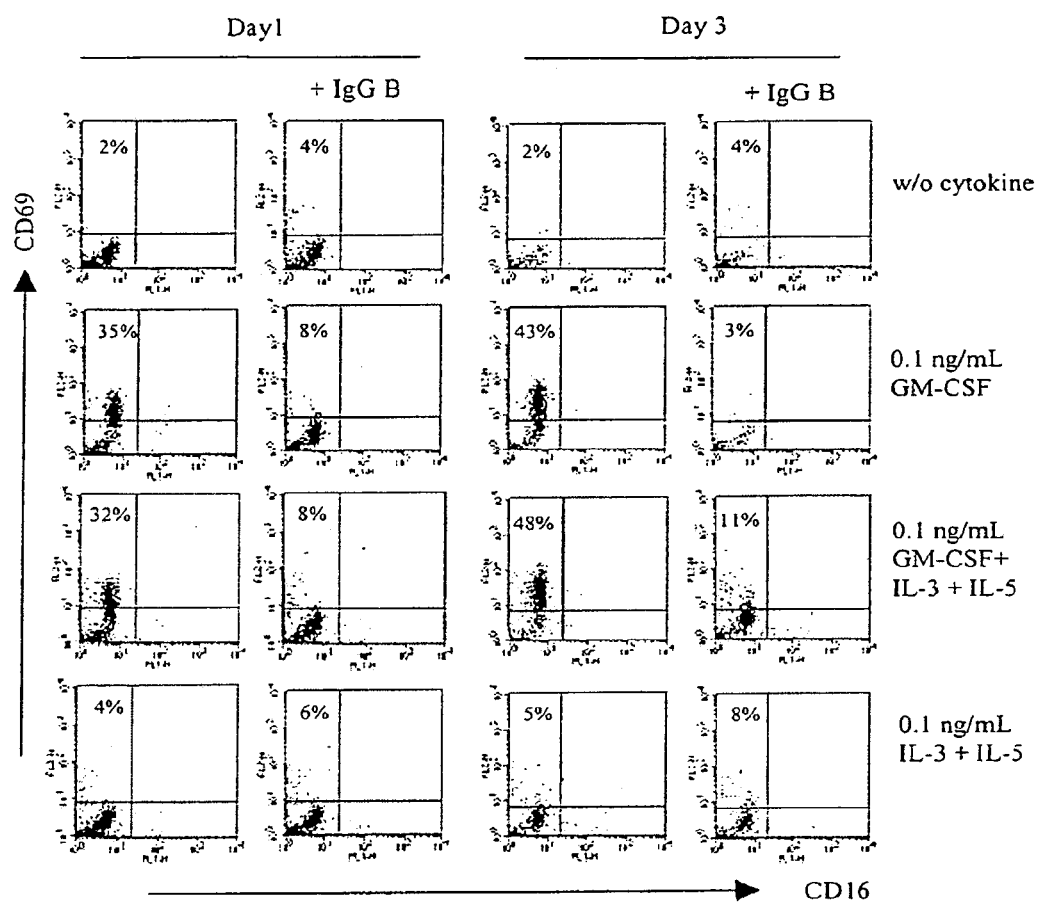
Figure 16:
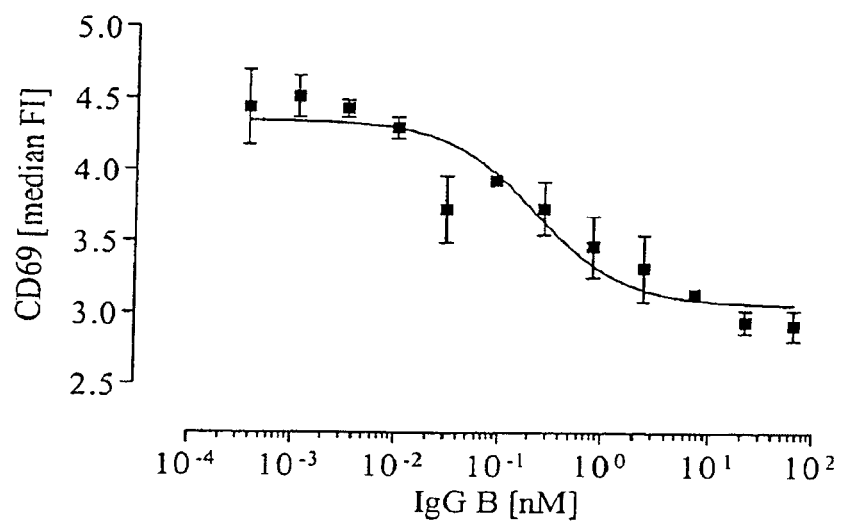
Figure 17:
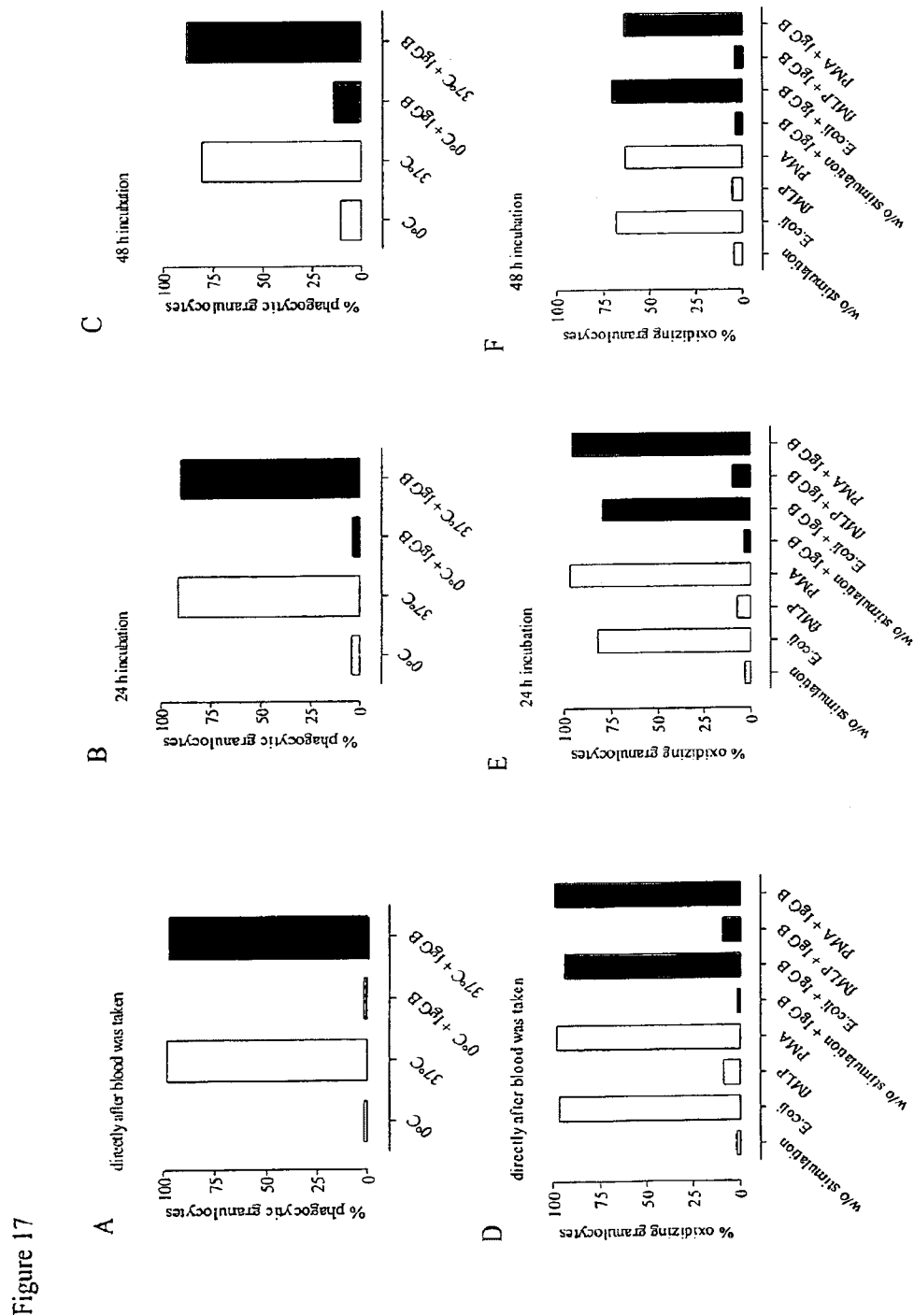
Figure 18:
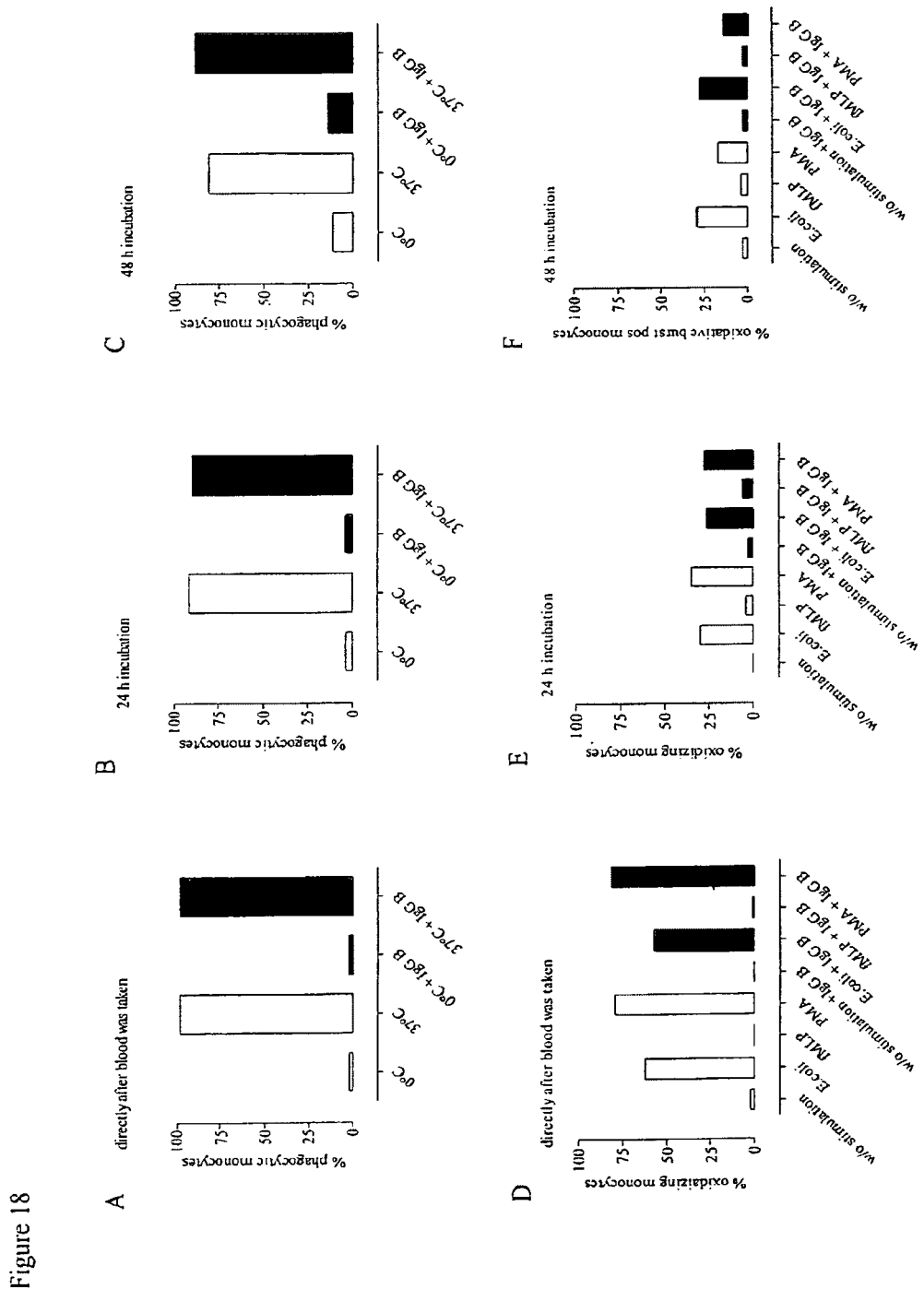

FIG. 8B Peptide spot radiogram showing binding of a fragment of a human monoclonal anti-GM-CSF to human GM-CSF FIG. 9 Qualitative results of a TF-1 proliferation inhibition assay performed using various representative human anti-rhGM-CSF scFv antibody fragments FIG. 10 Quantitative results of the TF-1 proliferation inhibition assay performed using various representative human anti-rhGM-CSF IgGs and corresponding scFv fragments FIG. 11 Quantitative results of the IL8 production assay performed using various representative human anti-rhGM-CSF scFv antibody fragments FIG. 12 Quantitative results of the TF-1 proliferation inhibition assay performed using various representative human anti-macGM-CSF IgGs and corresponding scFv fragments FIG. 13 Results of comparative binding study showing selectivity of binding of anti-GM-CSF antibody IgG B for recombinant human GM-CSF and GM-CSF from various non-primate species FIG. 14 Results of assay investigating the dependence of neutralizing potential of anti-GM-CSF antibody IgG B on the glycosylation of GM-CSF FIG. 15 Results of study of the effect of anti-GM-CSF antibody IgG B on GM-CSF-mediated eosinophil survival FIG. 16 Results of study of the effect of anti-GM-CSF antibody IgG B on GM-CSF-mediated eosinophil activation FIG. 17 Results of ex vivo toxicology study using anti-GM-CSF antibody IgG B, measured based on phagocytosis (A-C) and oxidative burst (D-F) by granulocytes FIG. 18 Results of ex vivo toxicology study using anti-GM-CSF antibody IgG B, measured based on phagocytosis (A-C) and oxidative burst (D-F) by monocytes

EXAMPLES

Example 1

Procurement of the Recombinant Human ("rh") GM-CSF Antigen used for the Generation of Neutralizing Human Antibodies and Fragments Thereof Example 1.1

Cloning, Expression and Purification of the rhGM-CSF Antigen

The gene encoding human GM-CSF antigen was subcloned into the pET22b(+) vector (Novagene, USA) from the expression vector pORF-hGM-CSF (Novagen, USA) via the PCR-introduced restriction enzyme recognition sites NdeI and XhoI. The hGM-CSF-encoding gene in pET22b(+) was fused to the pelB leader sequence and is suitable for expression in *E. coli* periplasm.

Protein production and purification was performed as described by the manufacturer. In brief, *E. coli* BL21DE3 were transformed with the expression plasmid and grown at 37° C. in selective medium to an optical density of 0.5-0.8 at 600 nm. Protein production was induced by addition of IPTG to 1 mM and reduction of temperature to 25° C. A periplasmic preparation was performed by osmotic shock using 20% sucrose solution to selectively destroy the cell wall maintaining an intact cell membrane. Native hGM-CSF contains two disulfide bridges and expression in the oxidative periplasm of *E. coli* allows for formation of these functionally important disulfide bridges.

Recombinant human GM-CSF ("rhGM-CSF") was purified in a two step purification process via immobilized metal affinity chromatography (IMAC) and gel filtration. An Äkta® FPLC System (Pharmacia) and Unicorn® Software were used for chromatography. All chemicals were of research grade and purchased from Sigma (Deisenhofen) or Merck (Darmstadt).

IMAC was performed using a Qiagen Ni-NTA Superflow column according to the protocol provided by the manufacturer. The column was equilibrated with buffer A2 (20 mM sodium phosphate pH 7.2, 0.4 M NaCl) and the periplasmic preparation ("PPP") (100 mL) was applied to the column (2 mL) at a flow rate of 2 mL/min The column was washed with 5 column volumes 5% buffer B2 (20 mM sodium phosphate pH 7.2, 0.4 M NaCl, 0.5 M imidazole) to remove unbound sample. Bound protein was eluted using 100% buffer B2 in 5 column volumes. Eluted protein fractions were pooled for further purification.

Gel filtration chromatography was performed on a Superdex 200 Prep Grade column (Pharmacia) equilibrated with PBS (Gibco). Eluted protein samples (flow rate 1 mL/min) were subjected to standard SDS-PAGE and Western Blot for detection. Prior to purification, the column was calibrated for molecular weight determination (molecular weight marker kit, Sigma MW GF-200). Protein concentrations were determined measuring OD 280 nm and calculated using the sequence-specific molecular extinction coefficient.

Example 1.2

Biotinylation of the rhGM-CSF Antigen

For phage library selection rhGM-CSF antigen produced in *E. coli* (see above) was biotinylated. Biotinylation was accomplished in PBS containing 5% DMSO (Sigma) with a five-fold molar excess of EZ-Link Sulfo NHS-LC-LC-Biotin (Pierce) for 1 hour at room temperature in a sample mixer (Dynal). For the separation of free Biotin and biotinylated rhGM-CSF antigen, anion exchange chromatography (Resource Q, Amersham Biosciences) was carried out according to standard protocols. The chromatography resulted in both approaches (designated A and B, described below) in two elution peaks. In case A the primary eluted peak was fractionated again via a second anion exchange chromatography step (same conditions as above) into two elution peaks. Afterwards the obtained fractions were serially diluted (dilutions 1:2; start concentration 6 µg/mL determined from the peak height) coated to 96 wells ELISA plates and detected. The detection was carried out using A) an anti-human GM-CSF antibody M500-A (Sigma, 2.5 µg/mL in PBS/1% BSA) detected with horseradish peroxidase-conjugated goat anti-mouse Fab2 specific polyclonal antibody (Dianova, 1 µg/mL PBS/1% BSA) and B) the maternal antibody (1 µg/mL PBS/1% BSA) detected with horseradish peroxidase-conjugated goat anti-rat polyclonal antibody (Dianova, 1 µg/mL PBS/1% BSA). The successful biotinylation was demonstrated by a similar ELISA experiment that was carried out using horseradish peroxide-conjugated streptavidin (Dako, 1 µg/mL PBS/1% BSA). The signal was developed by adding OPD substrate solution (Sigma) and detected at a wavelength of 492 nm (reference wavelength 620 nm). To estimate the degree of biotinylation the above mentioned ELISA was carried out using the anion exchange fractions directly or after an incubation step with $6.7 \times 10 \exp 7$ streptavidin magnetic beads (Dynabeads M-280-Streptavidin, Dynal) with gentle agitation for 30 minutes. The resulting supernatant was coated onto the wells of 96-well ELISA plates and detected as described above. The ELISA results showed that the second eluted peak contained the biotinylated rhGM-CSF and that about 95% of the eluted rhGM-CSF was conjugated. Concentrations were estimated using the original material as a standard and turned out to be about 20 µg/mL.

The retained bioactivity of the biotin-labeled rhGM-CSF was confirmed in TF-1 proliferation assays according to protocols described below in the characterization of the single chain antibodies (scFvs).

Example 1.3

Fluorescein Labeling of the rhGM-CSF Antigen

For binding studies on TF-1 cells recombinant human GM-CSF antigen produced in *E. coli* (see Example 1.2 above) was conjugated with fluorescein-5(6)-carboxamidocaproic acid N-succinimidyl ester (Fluka, fluorescein-NHS). The conjugation step was performed in borate buffer (0.05 M boric acid, 0.1 M NaCl, pH 8.5) containing 17.5% DMSO with a five-fold molar excess of fluorescein-NHS for 1 hour at room temperature in a sample mixer. Afterwards, gel filtration (Sephadex G25, Amersham Biosciences) was carried out to dissociate fluorescein-labeled rhGM-CSF antigen from free fluorescein-NHS. The gel filtration resulted in two peaks measured at a wavelength of 485 nm (reference wavelength 535 nm), whereas the primary peak represents the FITC-labeled rhGM-CSF. The degree of labeling was determined by defining the F/P ratio of the conjugate ([mg/mL]=($A_{280}$−0.35×$A_{493}$)×1.08; F/P=($A_{493}$/73.000)×(15.000/([mg/mL])). The determined concentration was 0.041 mg/mL with an F/P ratio of 1.2.

Example 2

Generation and Selection of Neutralizing Human Anti-GM-CSF Antibodies and Fragments Thereof Example 2.1

Cloning of the Maternal VH from Hybridoma HB-9569

As used throughout the foregoing examples, a "maternal" V-region denotes that the V-region in question originates from a full immunoglobulin molecule.

As used throughout the foregoing examples, a "hit" denotes a molecule which is known to bind an antigen of interest, but which binding has not been quantitatively evaluated. A "hit" is a molecule in an early stage of characterization for which small-scale production might have already been performed. Such a molecule is in the validation stage of characterization.

As used throughout the foregoing examples, a "lead" molecule denotes a molecule the binding and neutralization potentials of which have been quantified. Production of a "lead" molecule has already taken place on a large scale.

In the following examples one possible way of generating a fully human monoclonal antibody neutralizer of human GM-CSF and generation of fragments thereof is described.

The aim of this experiment is the isolation and sub-cloning of the gene encoding the VH in the maternal mAb produced by the hybridoma cell line HB-9569. The hybridoma HB-9569 was obtained from ATCC (USA). Hybridoma cells were cultivated in ATCC complete growth medium: RPMI 1640 medium with 2 mM L-glutamine adjusted to contain 1.5 g/L sodium bicarbonate, 4.5 g/L glucose, 10 mM HEPES, and 1.0 mM sodium pyruvate and supplemented with 0.05 mM 2-mercaptoethanol, fetal bovine serum 10% at 37° C. with 5% $CO_2$. For total RNA preparation, 1×10exp7 cells were used and RNA was prepared as described in the product manual of the Qiagen Omni-Skript Kit (Qiagen, Germany). cDNA was synthesized according to standard methods (Sambrook, Cold Spring Harbor Laboratory Press 1989, Second Edition).

For the isolation of heavy chain V-region DNA, RT-PCR was carried out using MHALT1R.V: GCC GAA TTC CAC CAT GGR ATG SAG CTG KGT MAT SCT CTT and Race GSP rIgG2a/b: CAC ACC GCT GGA CAG GGC TCC AGA GTT CC primer set. The following PCR program was used for amplification: Denaturation at 94° C. for 15 seconds, primer annealing at 52° C. for 50 seconds and primer extension at 72° C. for 90 seconds were performed over 40 cycles, followed by final extension at 72° C. for 10 minutes. Heavy chain DNA V-fragments were then isolated according to standard protocols.

The heavy chain DNA V-fragment was cloned into PCR script-CAM (Stratagene) as described by the manufacturer. The sequences were identified by sequencing.

Example 2.2

Selection of a Human VL

The aim of this experiment is the selection of a human VL which can pair with the maternal VH cloned as described above.

Example 2.2.1

Isolation of RNA from Selected IgD-Positive B-Cells 100 mL blood were taken from five healthy human donors. Peripheral blood mononuclear cells (PBMCs) were isolated by a ficoll-gradient according to standard methods. To select IgD-positive cells, 1 mL anti-mouse IgG-beads (CELLection™ Pan Mouse IgG Kit; DYNAL) were coated with 20 μg mouse anti-human IgD-antibody (PharMingen). Approximately 2.5×10exp7 PBMCs were added to the beads and incubated at 4° C. for 15 minutes. After washing four times with 1 mL RPMI-medium (BioChrom) IgD-positive cells were released from the beads by adding 8 μL release buffer (DNase) and transferred to a fresh tube. By this method 0.9×10exp5 to 3.7×10exp6 IgD-positive cells could be obtained. Total RNA was isolated from IgD-positive cells using the RNeasy® Midi Kit (QIAGEN) following the manufacturer's instructions. cDNA was synthesized according to standard methods (Sambrook, Cold Spring Harbor Laboratory Press 1989, Second Edition).

Example 2.2.2

PCR-Amplification of Variable Light Chain Regions (VL-Regions)

For the isolation of light chain V-region DNA, RT-PCR was carried out using V-kappa-(5'-huVK1-SacI-2001 (5'-GAGCCGCACG AGCCCGAGCT CCAGATGACC CAGTCTCC-3'), 5'-huVK2/4-SacI-2001 (5'-GAGCCGCACG AGCCCGAGCT CGTGATGACY CAGTCTCC-3'), 5'-huVK3-SacI-2001 (5'-GAGCCGCACG AGCCCGAGCT CGTGWTGACR CAGTCTCC-3'), 5'-huVK5-SacI-2001 (5'-GAGCCGCACG AGCCCGAGCT CACACTCACG CAGTCTCC-3'), 5'-huVK6-SacI-2001 (5'-GAGCCGCACG AGCCCGAGCT CGTGCTGACT CAGTCTCC-3'), 3'-hu-Vk-J1-SpeI-BsiWI (5'-GACGACACTA GTTGCAGCCA CCGTACGTTT GATTTCCACC TTGGTCC-3'), 3'-hu-Vk-J2/4-SpeI-BsiWI (5'-GACGACACTA GTTGCAGCCA CCGTACGTTT GATCTCCASC TTGGTCC-3'), 3'-hu-Vk-J3-SpeI-BsiWI (5'-GACGACACTA GTTGCAGCCA CCGTACGTTT GATATCCACT TTGGTCC-3'), 3'-hu-Vk-J5-SpeI-BsiWI (5'-GACGACACTA GTTGCAGCCA CCGTACGTTT AATCTCCAGT CGTGTCC-3') primer sets. RNA from IgD-positive B-cells was transcribed into cDNA (as described above) and used as template DNA in PCR reactions. Per PCR reaction, one 5'-primer was combined with one 3'-primer. The number of different PCR reactions was determined by the number of possible combinations of 5'- and 3'-primers. The following PCR-program was used for amplification: Denaturation at 94° C. for 15 seconds, primer annealing at 52° C. for 50 seconds and primer extension at 72° C. for 90 seconds were performed over 40 cycles, followed by final extension at 72° C. for 10 minutes. Light chain DNA V-fragments were then isolated according to standard protocols.

Example 2.2.3

Library Construction—Cloning of the Human VL Pool

A phage display library was generally constructed based on standard procedures, as for example disclosed in "Phage Display: A Laboratory Manual"; Ed. Barbas, Burton, Scott & Silverman; Cold Spring Harbor Laboratory Press, 2001.

The primers chosen for PCR amplification gave rise to 5'-SacI and 3'-SpeI recognition sites for the light chain V-fragments. Two ligation reactions were set up, each consisting of 400 ng of the kappa light chain fragments (SacI-SpeI digested) and 1400 ng of the plasmid pBluescript KS+ (SacI-SpeI digested; large fragment). The two resulting antibody V-light chain pools were then each transformed into 300 μL of electrocompetent *Escherichia coli* XL1 Blue by electroporation (2.5 kV, 0.2 cm gap cuvette, 25 mF, 200 Ohm, Biorad gene-pulser) resulting in a library size of 5.8×10exp8 independent clones.

Kappa (light chain) DNA-fragments from the different PCR amplifications were weighted for each ligation as follows: Each 5'-primer defines a specific group. Within these groups the 3'-primers define the subgroups. The subgroups were weighted 1:2:1:1 corresponding to the primers 3'-hu-Vk-J1-SpeI-BsiWI: 3'-hu-Vk-J2/4-SpeI-BsiWI: 3'-hu-Vk-J3-SpeI-BsiWI: 3'-hu-Vk-J5-SpeI-BsiWI. The groups were weighted according to their germline distribution 1:1:1:0.2: 0.2 corresponding to the primers 5'-huVK1-Sac-2001 :5'-huVK3-Sac-2001:5'-huVK2/4-Sac-2001:5'-huVK5-Sac-2001:5'-huVK6-Sac-2001.

After electroporation the assay was incubated in SOC broth (Fluka) for phenotype expression. The cultures were then each incubated in 500 mL of SB selection medium containing 50 µg/mL carbenicillin and 2% w/v glucose overnight. The next day, cells were harvested by centrifugation and plasmid preparation carried out using a commercially available plasmid preparation kit (Qiagen).

Example 2.2.4

Construction of the Antibody Library—Human VL—Maternal VH

PCR was performed to amplify the maternal VH from the vector containing the maternal VH described above in Example 2.1. For amplification a PCR protocol according to standard procedures was followed using the 5'-primer MVH8 (5'-GAG GTT CAG CTC GAG CAG TCT GGA GCT-3') and the 3'-primer 3'-MuVHBstEII (5'-TGA GGA GAC GGT GAC CGT GGT CCC TTG GCC CCA G-3').

After purification of the approximately 350 bp amplification product from an analytical agarose gel, the DNA fragment was cut with the restriction enzymes BstEII and XhoI. The phagemid pComb3H5BHis (this vector is described in the thesis dissertation of Dr. Ralf Lutterbüse) was digested accordingly and the large fragment was ligated with the above mentioned fragment. After transformation into E. coli XL1 blue, a single clone was cultivated in 100 mL SB medium (containing 50 µg/mL carbenicilline) and the plasmid was prepared according to standard protocols. The successful cloning was confirmed by sequencing the insert (Sequiserve, Munich).

This vector pComb3H5BHis/maternalVH was restricted with the restriction enzymes SacI and SpeI. The large vector fragment was isolated. Plasmid-DNA containing the VK-library from Example 2.2.3 was restricted with the restriction enzymes SacI and SpeI. The small VK fragment band (approx 350 bp) was isolated.

1200 ng of the vector fragment were ligated with 400 ng of the VK fragments and transformed into 300 µL of electrocompetent E. coli XL1 Blue by electroporation (2.5 kV, 0.2 cm gap cuvette, 25 mF, 200 Ohm) resulting in a total scFv library size of 2.8×10exp8 independent clones.

After phenotype expression and slow adaptation to carbenicillin, the antibody library was transferred into SB-Carbenicillin (50 µg/mL) selection medium. The antibody library was then infected with an infectious dose of 1×10exp12 particles of helper phage VCSM13 resulting in the production and secretion of filamentous M13 phage, wherein each phage particle contained single stranded pComb3H5BHis-DNA encoding a half-human scFv-fragment and displayed the corresponding scFv-protein as a translational fusion to phage coat protein III.

Example 2.2.5

Phage Display Selection of a Human VL

The phage particles carrying the scFv-repertoire were harvested from the culture supernatant by PEG8000/NaCl precipitation and centrifugation. Then approximately 1×10exp11 to 1×10exp12 scFv phage particles were resuspended in 0.4 mL of PBS/0.1% BSA and incubated with recombinant biotinylated soluble rhGM-CSF (produced in E. coli as described above in example 1) for 2 h with gentle agitation in a total volume of 0.5 mL (Antigen concentrations Rounds 1-3: 100 nM; round 4: 10 nM; round 5: 1 nM). Then 6.7× 10exp7 streptavidin magnetic beads (Dynabeads M-280-Streptavidin, Dynal) were added and further incubated under gentle agitation for 30 minutes.

scFv phage that did not specifically bind to the target antigen were eliminated by washing steps with PBS/0.1% BSA. For that purpose the biotinylated antigen—streptavidin bead complexes (with the potential scFv binders) were collected with a magnet and resuspended in 1 mL of the washing solution (one washing step). This washing procedure was repeated up to four times in further rounds.

After washing, binding entities were eluted by using HCl-glycine, pH 2.2. Following neutralization with 2 M Tris, pH 12, the eluate was used for infection of a fresh uninfected E. coli XL1 Blue culture. To elute remaining high binding entities this step was repeated using HCl-glycine, pH 1.0. This second eluate was again neutralized and used for infection of a fresh uninfected E. coli XL1 Blue culture. Both infected E. coli cultures were then mixed and cells that were successfully transduced with a phagemid copy, encoding a human scFv-fragment, were again selected for carbenicillin resistance and subsequently infected with VCSM13 helper phage to start the second round of antibody display and in vitro selection.

Plasmid DNA corresponding to 4 and 5 rounds of panning was isolated from E. coli cultures. For the production of soluble scFv-protein, VL-DNA fragments were excised from the plasmids (SacI-SpeI), and cloned via the same restriction sites in the plasmid pComb3H5BFlag/H is with the maternal VH differing from the initial pComb3H5BHis/maternal VH in that the expression construct (e.g. scFv) includes a Flag-tag (TGDYKDDDDK) between the scFv and the His6-tag and the additional phage proteins are deleted.

After ligation each pool (different rounds of panning) of plasmid DNA was transformed into 100 µL heat shock competent E. coli XL1 blue and plated onto carbenicillin LB-agar. Single colonies were picked into 100 µL of LB carb (50 µg/mL).

10 µl of this cell suspension was typically incubated in 5 ml SB medium supplemented with carbenicillin to a concentration of 50 µg/ml and MgCl$_2$ to a final concentration of 20 mM for approximately 6 h at 37° C. under agitation. Then IPTG was added to a final concentration of 1 mM and the incubation continued overnight on a shaker at 30° C.

Cells were centrifuged to a pellet and this pellet was typically resuspended in 0.5 ml PBS. By four rounds of freezing at −70° C. and thawing at 37° C., the outer membrane of the bacteria was destroyed by osmotic shock and the soluble periplasmic proteins including the scFvs were released into the supernatant. After elimination of intact cells and cell-debris by further centrifugation (5 min at 10,000×g), the supernatant (i.e. PPP) containing the scFvs was collected and examined further.

RhGM-CSF antigen (Leukine Liquid, Immunex) was immobilized on ELISA plates overnight at 4° C. (50 µl of 1 µg antigen/ml PBS per well). After washing the wells one time with PBS and blocking with PBS 3% BSA for 1 h at room temperature 100 µl PPPs containing scFvs were added to the wells and typically incubated for 1 h at room temperature. After three washes with PBS/0.05% Tween20, detection of scFv-fragments bound to immobilized antigen was carried out using an anti-flag M2 (1 µg/mL PBS/1% BSA) and detected with horseradish peroxidase-conjugated goat anti mouse Fab2 specific polyclonal antibody (Dianova, 1 µg/mL PBS/1% BSA). The signal was developed by adding 2,2'- azino-di [3-ethyl-benzthiazoline-6-sulphonic acid] ("ABTS") substrate solution and detected at a wavelength of 405 nm according to standard protocols.

From 20 clones tested (10 obtained after 4 rounds and 10 obtained after 5 rounds of panning), five lysates showed strong ELISA signals in contrast to PBS as a negative control on the recombinant antigen. ELISA results are shown in FIG. 1, in which the various scFv molecules tested are arrayed along the x-axis and the y-axis shows the absorption intensity measured, with higher absorption indicating stronger binding. The PBS negative control is indicated on the x-axis at the far left. ScFv molecules exhibiting appreciable binding are denoted with above the respective absorption intensity column either a diamond or an asterisk. The diamond and asterisk in FIG. 1 represent two different sequences, i.e. the scFv whose absorption intensity column is indicated with a diamond was of one sequence, whereas all scFvs whose absorption intensity columns are indicated by asterisks share the same common sequence.

The five ELISA-positive clones were subjected to DNA sequencing. Sequencing was carried out at Sequiserve (Munich). A total of four clones shared the DNA sequence corresponding to scFv 5-306 while the other sequence (4-301) was identified only once. The dominant sequence corresponding to scFv 5-306 as well as the sequence 4-301 were of human origin and displayed very close homology to human germ line sequence Vk1-O12.

Example 2.2.6

Characterization of scFv Hit Constructs Derived from the huVL Selection

The aim of the following experiments was the characterization of the scFv hits generated by the methods described above.

Example 2.2.6.1

Small-Scale Expression and Purification of ScFv Hits (Derived as Described Above) in *E. coli*

To obtain PPPs the cells were grown in SB-medium supplemented with 20 mM $MgCl_2$ and carbenicillin 50 µg/mL and were redissolved in 1 mL PBS after harvesting. The outer membrane of the bacteria was destroyed by temperature shock (four rounds of freezing at −70° C. and thawing at 37° C.) and the soluble periplasmic proteins including the scFvs were released into the supernatant. After elimination of intact cells and cell-debris by centrifugation, the supernatants containing the scFvs were collected and examined further. For further purification, 25 µL 20 mM $NaH_2PO_4$, 400 mM NaCl, 250 mM imidazole, pH 7.0 was added to a respective PPP. The PPP was purified via Ni-NTA Spin Columns (Qiagen) as recommended in the manual. In brief, a respective PPP solution was added to the pre-equilibrated column to bind to the resin. The Spin Columns were washed twice with 20 mM $NaH_2PO_4$, 400 mM NaCl, 20 mM imidazole, pH 7.0. The bound protein was eluted twice in 200 µL 20 mM $NaH_2PO_4$, 400 mM NaCl, 250 mM imidazole, pH 7.0. The purified scFv proteins were further analyzed with respect to binding strength (kinetic off rate) and neutralization capabilities (inhibition of GM-CSF dependent TF-1 proliferation) as described in the subsequent examples. Though not separating and distinguishing between the different possible conformations of the scFv, this crude purification of PPP yields 80% pure scFv protein as judged by Western-blot analysis (data not shown).

Example 2.2.6.2

Inhibition of FITC-Labelled rhGM-CSF

The aim of this experiment is to show that the identified scFv clones are capable of inhibiting binding of rhGM-CSF to the GM-CSF receptor complex displayed on the surface of TF-1 cells. Neutralizing scFv constructs would be expected to compete for the receptor-binding epitope on the rhGM-CSF molecule, rendering it impossible for rhGM-CSF to bind to the GM-CSF receptor complex. To the extent that binding by rhGM-CSF to its receptor is inhibited in the above manner, one would expect to observe a decrease in the intensity of fluorescence staining of TF-1 cells by fluorescein-labelled rhGM-CSF (rhGM-CSF-FITC) in a flow cytometry-based assay.

The following describes the performance of such a flow cytometry-based assay. A final concentration of 0.4 μg/mL rhGM-CSF-FITC conjugate in PBS was incubated with 10 μg/ml of the maternal antibody or undiluted periplasmic extract of the scFv that had been purified with NiNTA Spin Column. The protein samples were left to equilibrate at 25° C. for 1 h prior to addition of a suspension of TF-1 cells. The TF-1 cells were cultivated in RPMI 1640 medium (Gibco; L-glutamine, phenol-red free), 10% heat-inactivated FCS in the absence of rhGM-CSF overnight. A final concentration of 2×10exp6 cells/mL and 150 μL of cell suspension were used per sample. The cells were harvested by centrifugation at 500×g at 4° C. for 3 min and washed twice with FACS buffer. The washed cells were resuspended in 100 μL of pre-equilibrated protein sample containing the rhGM-CSF-FITC and respective maternal antibody or scFv. The samples were incubated at 4° C. for 60 min. After two further washes the cells were resuspended in 150 μL ice cold FACS buffer and subsequently analysed by flow cytometry. The results are shown in FIG. 2. Specifically, FIG. 2 shows a graph in which various test molecules are arrayed along the x-axis, and in which the mean fluorescence intensity ("MFI") is indicated on the y-axis. As can be seen in FIG. 2, a clear loss of fluorescence intensity of the TF-1 cells was observed with the maternal antibody (second from left along the x-axis). The competition binding to rhGM-CSF of the scFv molecule designated 5-306 could be monitored by loss in fluorescence staining of TF-1 cells while the scFv molecule 4-301 hardly showed any effect. Since these results suggest that the scFv molecule designated 5-306 may be a promising neutralizer of GM-CSF, further analysis of the neutralizing activity was restricted to scFv 5-306.

Example 2.2.6.3

Large Scale Expression and Purification of scFv Lead

Protein production and purification on a large scale was performed as follows. In brief, *E. coli* BL21DE3 were transformed with the expression plasmid and grown at 37° C. in 1 L selective medium to an optical density at 600 nm of 0.5-0.8. Protein production was induced by addition of IPTG to 1 mM and the cultures were incubated for another 16 h with agitation at a temperature of 25° C. The cells were harvested by centrifugation at 5,000×g for 10 mM and resuspended in 100 mL 1×PBS. Periplasmic proteins were extracted by optimal, sequential freezing in ethanol/dry ice and thawing in a 37° C. water bath over four cycles. Finally, the extract was centrifuged at 10,000×g for 20 min.

The scFv 5-306 was isolated in a two-step purification process of immobilized metal affinity chromatography (IMAC) and gel filtration. All leads were purified according to this method. Äkta® FPLC System (Pharmacia) and Unicorn® Software were used for chromatography. All chemicals were of research grade and purchased from Sigma (Deisenhofen) or Merck (Darmstadt).

IMAC was performed using a Qiagen Ni-NTA Superflow column according to the protocol provided by the manufacturer. The column was equilibrated with buffer A2 (20 mM sodium phosphate pH 7.2, 0.4 M NaCl) and the PPP (100 mL) was applied to the column (2 mL) at a flow rate of 2 mL/min The column was washed with 5 column volumes 5% buffer B2 (20 mM sodium phosphate pH 7.2, 0.4 M NaCl, 0.5 M imidazole) to remove unbound sample. Bound protein was eluted using 100% buffer B2 in 5 column volumes. Eluted protein fractions were pooled for further purification.

Gel filtration chromatography was performed on a HiLoad™ 16/60 Superdex 75 Prep Grade column (Pharmacia) equilibrated with PBS (Gibco). Eluted protein samples (flow rate 1 mL/min) were subjected to standard SDS-PAGE and Western Blot for detection. Prior to purification, the column was calibrated for molecular weight determination (molecular weight marker kit, Sigma MW GF-200). The size dependent separation on the Superdex 75 Prep Grade column resulted in clearly distinguishable monomer and associative dimer peak fractions of the scFv leads. Protein concentrations were determined measuring optical density at 280 nm and were calculated using the sequence-specific molecular extinction coefficient of the respective scFv lead.

Example 2.2.6.4

Inhibition of rhGM-CSF-Dependent Proliferation of TF-1 Cells by an Scfv Lead

The aim of this experiment is to achieve qualitative information on the neutralizing activity of the half-human scFv 5-306 using the hGM-CSF dependant cell line TF-1 (DSMZ ACC 334). TF-1 cells were cultivated in RPMI 1640 medium (Gibco; L-glutamine, phenol-red free), 10% heat inactivated FCS in the presence of 2.5 ng/mL rhGM-CSF as described by the distributor (Deutsche Sammlung von Mikroorganismen and Zellkulturen GmbH, Braunschweig, Germany). Cells were grown to a cell density of 0.5×10exp6 cells/mL. For the proliferation assay TF-1 cells were harvested by centrifugation at 300×g for 4 min and washed with 1×PBS (Dulbecco's, Gibco). Cells were resuspended at a final concentration of 1×10exp5 cells/mL in RPMI 1640, 10% FCS and 90 μL cell suspension per Microtest flat bottom cell culture plate well were used (0.9×10exp4 cells/well). A final concentration of 0.3 ng/mL rhGM-CSF was used to stimulate the proliferation of the TF-1 cells. For neutralization of hGM-CSF dependent proliferation 10 μL of purified scFv were added to 100 μL TF-1 and rhGM-CSF solution in a dilution series ranging from approximately 100 μg/ml to 100 pg/ml. The samples were incubated at 37° C. at 5% $CO_2$ for 72 h. After 72 h the proliferative status of the TF-1 cells was determined adding WST-1 and monitoring the colorimetric change with an ELISA reader at 450 nm The data were fitted for half maximal inhibition of proliferation ($IC_{50}$) using the non-linear regression curve fit of the Prism software.

A clearly dose-dependant proliferation inhibiting effect of scFv 5-306 could be seen and was comparable for the monomeric and the dimeric conformational forms. By fitting for the half-maximal inhibition of proliferation an $IC_{50}$ value of 7.3 nM was determined for the monomeric form and 3.5 nM for the dimeric form. The results are shown in FIG. 3.

Example 2.3

Construction of the Antibody Libraries and Phage Display Selection of Human VHs

The aim of the following experiments is the selection of a set of human VH regions that would pair with the human VL region of scFv 5-306 selected as described above.

Example 2.3.1

Isolation of RNA from Peripheric Blood Mononuclear Cells (PBMCs)

100 mL blood were taken from five healthy human donors. Peripheral blood mononuclear cells (PBMCs) were isolated by a ficoll-gradient according to standard methods. Total RNA was isolated from PBMCs using the RNeasy® Midi Kit (QIAGEN) following the manufacturer's instructions. cDNA was synthesized according to standard methods (Sambrook, Cold Spring Harbor Laboratory Press 1989, Second Edition).

Example 2.3.2

PCR-Amplification of Variable Heavy Chain Regions (VH-Regions)

The VH library was constructed and named Lib 134-VH. This VH-library consists of the human repertoire of FR1—CDR2—FR2—CDR2—FR3 from the PCR amplified VH-regions of the above described PBMC pool, linked operatively to the VH CDR3 of the maternal antibody followed by a human FR4 germline sequence.

For the isolation of human template VH-regions, RT-PCR was carried out using a 5'-VH-specific primer set (5'-huVH1, 3,5-XhoI-2001 (5'-AGG TGC AGC TGC TCG AGT CTG G-3'), 5'-huVH4-XhoI-2001 (5'-CAG GTG CAG CTG CTC GAG TCG GG-3'), 5'-huVH4B-XhoI-2001 (5'-CAG GTG CAG CTA CTC GAG TGG GG-3')) and a set of two 3'-VH-specific primers (3'-hu-VH-BstEII-2001 (5'-CTG AGG AGA CGG TGA CC-3'), 3'-hu-VH-J3-BstEII-2001 (5'-CTG AAG AGA CGG TGA CC-3')). Per PCR reaction, one 5'-primer was combined with one 3'-primer; the number of different PCR reactions was determined by the number of possible combinations of 5'- and 3'-primers. The PBMC cDNA (as described above of four donors only was used as a source of VH-genes). The following PCR-program was used for amplification: Denaturation at 94° C. for 15 seconds, primer annealing at 52° C. for 50 seconds and primer extension at 72° C. for 60 seconds was performed over 40 cycles, followed by final extension at 72° C. for 10 minutes. The amplification products with a size of approximately 350 bp were isolated according to standard methods.

For the isolation of Lib 134-VH-regions, RT-PCR was carried out in two steps. First, the human heavy chain VH-segments (FR1-CDR1-FR2-CDR2-FR3) were PCR-amplified from the isolated template VH fragments using the same 5'-VH-specific primer set as described above (5'-huVH1,3,5-XhoI-2001, 5'-huVH4-XhoI-2001, 5'-huVH4B-XhoI-2001) and a 3'-specific primer set (3'-Lib 134-VH-1A-MH3 (5'-GTA ATC AAA GTA GAC TGC TAT CAG ACC CGA TCT YGC ACA GTA ATA CAC GGC-3'), 3'-Lib 134-VH-1B-

MH3 (5'-GTA ATC AAA GTA GAC TGC TAT CAG ACC CGA TCT YGC ACA GTA ATA CAY RGC-3'), 3'-Lib 134-VH-3A-MH3 (5'-GTA ATC AAA GTA GAC TGC TAT CAG ACC CGA TCT NGY ACA GTA ATA CAC RGC-3'), 3'-Lib 134-VH-3B-MH3 (5'-GTA ATC AAA GTA GAC TGC TAT CAG ACC CGA TCT NGC ACA GTA ATA CAA RGC-3'), 3'-Lib 134-VH-4-MH3 (5'-GTA ATC AAA GTA GAC TGC TAT CAG ACC CGA TCT SGC ACA GTA ATA CAC RGC-3')) for the human VH subfamilies 1, 3 and 4 matching in the very terminal region of FR3.

The following primer combinations were used:
a) 5'-huVH1,3,5-XhoI-2001×3'-Lib 134-VH-1A-MH3
b) 5'-huVH1,3,5-XhoI-2001×3'-Lib 134-VH-1B-MH3
c) 5'-huVH1,3,5-XhoI-2001×3'-Lib 134-VH-3A-MH3
d) 5'-huVH1,3,5-XhoI-2001×3'-Lib 134-VH-3B-MH3
e) 5'-huVH4-XhoI-2001×3'-Lib 134-VH-4-MH3
f) 5'-huVH4B-XhoI-2001×3'-Lib 134-VH-4-MH3

Per PCR reaction, one 5'-primer was combined with the 3'-primer; the number of different PCR reactions was determined by the number of possible combinations of 5'- and the 3'-primer. The following PCR-program was used for amplification: Denaturation at 94° C. for 15 seconds, primer annealing at 52° C. for 50 seconds and primer extension at 72° C. for 90 seconds was performed over 40 cycles, followed by final extension at 72° C. for 10 minutes. Through this PCR step and the respective 3'-primer sequence, the human VH segments are prolonged for a part of the maternal VH CDR3, which then in turn is the priming site for the second step PCR 3'-primer.

These VH-(FR1-CDR1-FR2-CDR2-FR3) DNA-fragments were then used as templates in a second PCR reaction using again the respective 5'VH-specific primer and a universal 3' primer matching to the universal 3'-terminus of the amplified DNA-fragments (3'-Lib 134-JH3-BstE2, 5'-AGA GAC GGT GAC CAT TGT CCC TTG GCC CCA GTA ATC AAA GTA GAC TGC-3').

The following PCR-program was used for amplification:
Denaturation at 94° C. for 15 seconds, primer annealing at 52° C. for 50 seconds and primer extension at 72° C. for 60 seconds were performed over 40 cycles, followed by final extension at 72° C. for 10 minutes. The DNA V-fragments were isolated according to standard protocols.

Example 2.3.3

Library Construction—Cloning of the Human VH Pool

In a second round of the foregoing method, the human VL of scFv 5-306 identified in the first, previous selection was chosen, and subsequently combined with the library of human VH fragments described in Example 2.3.2 with the aim of generating a human scFv. A phage display library was generally constructed based on standard procedures, as for example disclosed in "Phage Display: A Laboratory Manual"; Ed. Barbas, Burton, Scott & Silverman; Cold Spring Harbor laboratory Press, 2001.

Heavy chain DNA-fragments from the different PCR amplifications were weighted for each ligation as follows:
a:b:c:d:e:f=3:1:3:1:1:1, wherein a-f have the following meanings:
a) 5'-huVH1,3,5-XhoI-2001×3'-Lib 134-VH-1A-MH3×3'-Lib 134-JH3-BstE2
b) 5'-huVH1,3,5-XhoI-2001×3'-Lib 134-VH-1B-MH3×3'-Lib 134-JH3-BstE2
c) 5'-huVH1,3,5-XhoI-2001×3'-Lib 134-VH-3A-MH3×3'-Lib 134-JH3-BstE2
d) 5'-huVH1,3,5-XhoI-2001×3'-Lib 134-VH-3B-MH3×3'-Lib 134-JH3-BstE2
e) 5'-huVH4-XhoI-2001×3'-Lib 134-VH-4-MH3×3'-Lib 134-JH3-BstE2
f) 5'-huVH4B-XhoI-2001×3'-Lib 134-VH-4-MH3×3'-Lib 134-JH3-BstE2

One ligation reaction was set up consisting of 400 ng of human Lib 134-VH fragment pool (XhoI-BstEII digested) and 1200 ng of the plasmid pComb3H5BHis/5-306 VL (the DNA encoding the VL region of scFv 5-306 was cloned via the restriction sites SacI and SpeI into pComb3H5BHis according to standard procedures). The resulting antibody human VH pool was then transformed into 300 µL of electrocompetent Escherichia coli XL1 Blue by electroporation (2.5 kV, 0.2 cm gap cuvette, 25 mF, 200 Ohm, Biorad gene-pulser) resulting in a library size of 1.6×10exp8 independent clones in total.

After electroporation the assay was incubated in SOC broth (Fluka) for phenotype expression. The cultures were then each incubated in 500 mL of SB selection medium containing 50 µg/mL carbenicillin and 2% v/v glucose overnight. The next day, cells of the cultures were harvested by centrifugation and plasmid preparation carried out using a commercially available plasmid preparation kit (Qiagen) to preserve the DNA library.

1.5 µg of this plasmid pool encoding the respective scFv pool were then electroporated into E. coli XL1blue (2.5 kV, 0.2 cm gap cuvette, 25 mF, 200 Ohm, Biorad gene-pulser) resulting in a library size of 2.4×10exp9 independent clones in total. After phenotype expression and slow adaption to carbenicillin the antibody library was transferred into SB-Carbenicillin (50 µg/mL) selection medium. The antibody library was then infected with an infectious dose of 1×10exp12 particles of helper phage VCSM13 resulting in the production and secretion of filamentous M13 phage, wherein each phage particle contained single stranded pComb3H5BHis-DNA encoding a human scFv-fragment and displayed the corresponding scFv-protein as a translational fusion to phage coat protein III.

Example 2.3.4

Phage Display Selection of a Human VH

The resulting phage library carrying the cloned scFv-repertoire was harvested from the culture supernatant by PEG8000/NaCl precipitation and centrifugation. Approximately 1×10exp11 to 1×10exp12 scFv phage particles were resuspended in 0.4 mL of PBS/0.1% BSA and incubated with recombinant biotinylated soluble rhGM-CSF (E. coli material, as described in example 1) for 1 h under gentle agitation in a total volume of 0.5 mL. Then 6.7×10exp7 streptavidin magnetic beads (Dynabeads M-280-Streptavidin, Dynal) were added and further incubated under gentle agitation for 30 minutes.

scFv phage that did not specifically bind to the target antigen were eliminated by washing steps with PBS/0.1% BSA. For that purpose the biotinylated antigen—streptavidin bead complexes (with the potential scFv binders) were collected via a magnet and resuspended in 1 mL of the washing solution (one washing step). This washing procedure was repeated up to four times. After washing, binding entities were eluted by using HCl-glycine pH 2.2 and after neutralization with 2 M Tris pH 12, the eluate was used for infection of a fresh uninfected E. coli XL1 Blue culture.

To elute remaining high binding entities the beads were resuspended directly in 200 μL of a fresh E. coli XL1 blue culture (OD600≥0.5) and incubated for 10 minutes under gentle agitation. Both cultures were then mixed and cells successfully transduced with a phagemid copy, encoding a human scFv-fragment, were again selected for carbenicillin resistance and subsequently infected with VCMS13 helper phage to start the second round of antibody display and in vitro selection.

A total of 4 rounds of selections were carried out for the two antibodies. Antigen concentrations were decreased during selection to the final concentrations as follows:

| | |
|---|---|
| 1. round | 100 nM |
| 2. round | 10 nM |
| 3. round | 10 nM |
| 4. round | 10 nM |

Plasmid DNA from E. coli cultures was isolated corresponding to 3 and 4 rounds of panning.

For the production of soluble scFv-protein the VH-VL-DNA fragments were excised from the plasmids (XhoI-SpeI), and cloned via the same restriction sites in the plasmid pComb3H5BFlag/H is (w/o additional phage proteins required for phage infection). After ligation each pool (different rounds of panning) of plasmid DNA was transformed into 100 μL heat shock competent E. coli TG1 and plated on carbenicillin LB-agar. Single colonies were picked and inoculated into 120 μL of LB carb (50 μg/mL) 1% glucose in 96-well plates (Greiner). The wells were sealed with a semi-permeable membrane (Greiner) and the plates were incubated overnight at 37° C. in a shaking incubator (master plate). Then 10 μL of the master plate cultures were transferred into a second 96 well plate (working plate) containing 90 μL LB carb (50 μg/mL) 0.1% glucose per well. After incubation for 4 h in a 37° C. shaking incubator, scFv production was induced by adding 20 μL LB carb 6 mM IPTG to each well. After another incubation step overnight at 30° C. with shaking, cells were lysed in a 1 h incubation at room temperature with 40 μL lysis buffer (400 mM boric acid, 320 mM NaCl, 4 mM EDTA pH 8, 2.5 mg/mL lysozyme). Residual cells and cell debris were separated by centrifugation for 12 minutes at 1,900×g (Hettich).

The supernatants containing scFv molecules were then tested for binding in ELISA assays. Detection of scFv-fragments bound to immobilized rhGM-CSF antigen (Leukine) was carried out using an anti-flag M2 (1 μg/mL PBS/1% BSA) detected with horseradish peroxidase-conjugated goat anti mouse Fab2 specific polyclonal antibody (Dianova, 1 μg/mL PBS/1% BSA). The signal was developed by adding ABTS substrate solution and detected at a wavelength of 405 nm Of approximately 100 clones tested after the third selection round, 12 clones showed strong binding to rhGM-CSF. Of approximately 160 clones tested after the fourth round over 80% of the lysates showed strong ELISA signals as compared to PBS as a negative control on the recombinant antigen. Results from representative clones are depicted in FIG. 4, in which these representative clones are arrayed along the x-axis, and absorbance intensity is indicated on the y-axis. As can be seen from FIG. 4, the PBS negative control (second from right on the x-axis) showed no appreciable binding, whereas representative scFv clones scFv A, scFv 3035, scFv 3039, scFv 3080 and scFv 5-306 showed different degrees of binding strength by ELISA.

All lysates were tested without rhGM-CSF in parallel experiments for unspecific binding to the blocking agent. No significant detectable signal could be observed, indicating the specificity of the binding to the rhGM-CSF.

The DNA sequences of more than 13 ELISA-positive scFv clones were determined In total, six different sequences were identified. All sequences were of human origin and were closely related to the human germline sequence VH-1 1-O2.

Example 2.3.5

Characterization of Human scFv Constructs Containing Human VL and VH Regions

Example 2.3.5.1

Large Scale Production and Purification of scFv Leads Constructs Produced by the Method Described in Example 3

The scFv leads were isolated and purified as described in Example 2.2.6.3.

Example 2.3.5.2

Kinetic Binding Analysis of scFv Leads by Surface Plasmon Resonance (SPR)

The aim of the experiment is the in-depth characterization of the scFv leads. Binding kinetics (kd and ka) of the scFv leads were measured by injecting 10 μL of purified protein in dilution series ranging from 10 μg/mL to 1 pg/mL purified scFv and monitoring the dissociation at 25° C. for 100 sec. Protein was buffered in HBS-EP (0.01 M HEPES, pH 7.4, 0.15 M NaCl, 3 mM EDTA, 0.005% surfactant P20). The data were fitted using BIAevalution™ software determining the rate constant for dissociation and association kinetics with a 1:1 Langmuir binding equation (Formulae 1 and 2), where A is the concentration of injected analyte and B is the concentration of ligand.

$$dB|dt=-(ka*[A]*[B]-kd*[AB]) \quad (1)$$

$$dAB|dt=-(ka*[A]*[B]-kd*[AB]) \quad (2)$$

Kinetic binding curves were determined using up to 8 concentrations of each scFv lead analyzed. The independent fitting of the raw data resulted in dissociation and association rate constants that were used to calculate the equilibrium dissociation constant (KD, the results are shown in Table 1).

TABLE 1

| | ka [1/Ms] | kd [1/s] | KD [M] | IC50 [nM] |
|---|---|---|---|---|
| 3035 | $1.6 \times 10^5 \pm 1.1 \times 10^5$ | $1.5 \times 10^{-3} \pm 0.4 \times 10^{-3}$ | $0.9 \times 10^{-8}$ | 3.2 |
| 3039 | $0.6 \times 10^4 \pm 0.4 \times 10^4$ | $0.9 \times 10^{-4} \pm 0.1 \times 10^{-4}$ | $1.7 \times 10^{-6}$ | 130.5 |
| scFvA | $1.7 \times 10^6 \pm 1.1 \times 10^6$ | $1.6 \times 10^{-3} \pm 0.2 \times 10^{-3}$ | $1.2 \times 10^{-9}$ | 2.6 |
| 3080 | $1.0 \times 10^5 \pm 0.5 \times 10^5$ | $3.5 \times 10^{-3} \pm 0.2 \times 10^{-3}$ | $3.5 \times 10^{-8}$ | 19.1 |

2.3.5.3: Inhibition of rhGM-CSF Dependent Proliferation of TF-1 Cells by scFv Leads After confirming that the strength of specific binding was preserved in the scFv leads, the aim of this experiment was to assess the specificity of the interaction of the scFv lead with the antigen rhGM-CSF. The inhibition of the biological function of the antigen rhGM-CSF by binding of the scFv was characterized in a TF-1 proliferation-inhibition experiment.

TF-1 proliferation-inhibition experiments were performed as described above. Cells were resuspended at a final concentration of 1×10exp5 cells/mL in RPMI 1640, 10% FCS and 90 µL cell suspension per well were used (0.9×10exp4 cells/well). A final concentration of 0.3 ng/mL rhGM-CSF was used to stimulate the proliferation of the TF-1 cells. For neutralization of rhGM-CSF dependent proliferation purified scFv in 1×PBS was added in a dilution series with final protein concentrations ranging from 100 µg/mL to 10 pg/mL. 10 µL of dialyzed and sterile filtered protein solution (0.22 µm filter) was added to 100 µL TF-1 and rhGM-CSF solution. The samples were incubated at 37° C. at 5% $CO_2$ for 72 h. After 72 h the proliferative status of the TF-1 cells was determined adding WST-1 and monitoring the colorimetric change with an ELISA reader at 450 nm (FIG. 5). As can be seen in FIG. 5, the human GM-CSF neutralizing activity is clearly demonstrated. ScFv A displayed the strongest neutralizing activity.

Example 2.4

Optimizing the Binding Characteristics of the Selected scFvs

It was contemplated that the biological activity of a neutralizing agent for a monomeric ligand may be improved or even optimized by increasing the binding strength between neutralizer and ligand, in particular by increasing the off-rate of the neutralizer.

This can preferably be achieved by mutating the sequence of the respective VH and VL region in a random fashion by (i) inserting one or more mutations randomly throughout the whole sequence or by (ii) inserting single mutations or multiple contiguous mutations (e.g. stretches of five, six, seven, eight, nine or ten amino acids) into regions of the scFv that have a high probability of interacting with the antigen. The respective mutants must then be characterized for any increase in activity or, prior to characterization, must be enriched for preferential qualities (e.g. stronger binding) via suitable selection methods (i.e. phage display).

Example 2.4.1

Increasing the Affinity by Mutating the VH CDR3 in One or More Positions

To improve the binding characteristics of an antibody fragment, for example an scFv molecule, by single point mutations or short amino acid stretches, amino acid residues must be targeted which have a very high probability of interacting with the respective antigen. With this approach, it is not necessary to screen more than only a limited number of mutants without reducing the probability of success. The heavy chain CDR3 of an antibody or fragment thereof usually contributes strongly to the overall binding of an antigen by this antibody or antibody fragment. It was therefore contemplated that a promising way of increasing the binding affinity of an antibody or antibody fragment may be to mutate the nucleotide sequence coding for VH CDR3.

A variety of different methodologies exists for performing such targeted random mutagenesis, some of which are described in the following in terms of how the binding affinity of scFv molecules described above may be increased:

A) To target the VH CDR3 a suitable restriction site must be introduced into the nucleotide sequence within the VH CDR3, preferentially by gene synthesis of the whole VH region with a modified CDR3 nucleotide sequence by keeping the original amino acid sequence (Entelechon, Germany). Via cleavage by the respective restriction enzyme and adding S1 nuclease/Klenow DNA polymerase I and dGTP followed by a mutant oligomer duplex, targeted random mutagenesis in one or more amino acid positions may be performed according to Matteucci and Heyneker, Nucleic Acids Research 11: 3113 ff (1983). The mutagenized VHs are subsequently combined with the respective VL (via a suitable linker) in a suitable scFv expression vector and transformed into *E. coli* cells. Single colonies expressing the variant scFvs can then be picked and screened for improved scFvs as described for screening and characterization of scFv hits and leads in the previous examples.

B) An alternative method is the oligonucleotide-mediated mutagenesis by the double primer method as described in detail in Sambrook, Fritsch, Maniatis (1989) "A laboratory manual". In essence the VH region is cloned into an M13-based vector and single stranded plasmid is isolated. A primer able to hybridize to the single stranded plasmid template containing a randomized sequence is annealed and extended. After propagation of the respective plasmid pool in *E. coli*, the mutated VHs can be harvested from the pool of plasmids and combined with the original VL (via a suitable linker) in a suitable scFv expression vector and transformed into *E. coli* cells. Single colonies expressing the variant scFvs are picked and screened for improved scFvs as described for screening and characterization of scFv hits and leads in the previous examples.

C) Yet another alternative is to mutate up to six or even more contiguous amino acids. To this end, a deletion variant of the VH nucleotide sequence may be constructed having a deleted CDR3 and FR4. This construct is used as a template for a one- or two-step PCR amplification, in which a suitable 5'-primer (hybridizing to the 5' end of the VH sequence and adding a suitable cloning site) is combined with a set of 3'-primers that anneal at the 3' end of the FR3 region as template and add a CDR3 and FR4 region (with a suitable restriction site) to the amplification fragment. This set of 3'-primers contains a sequence of one or more triplets to insert random codons within the CDR3 sequence. This pool of VH regions containing randomized CDR3 regions may then be subsequently combined with the respective VL (via a suitable linker) in a suitable scFv expression vector and transformed into *E. coli* cells. Single colonies expressing the variant scFvs are then picked and screened for improved scFvs as described for screening and characterization of scFv hits and leads in the previous examples.

Respective pools of mutated scFvs that have a higher diversity (as can be easily screened) can be cloned into a suitable phage display vector and improved scFvs may then be selected by phage display on the antigen of interest preferentially under conditions of decreasing antigen concentrations to select for higher affinities. Phage display selections are carried out according to standard protocols as described elsewhere herein. Any of the above methods A to C may be combined or performed in repeated cycles to further improve and optimize already modified scFvs.

Example 2.4.2

Increasing the Affinity by Mutating the V-Regions Randomly Throughout the Whole Sequence Instead of mutating specific sites of the scFv that have a high probability of interacting with the respective antigen, a more pragmatic approach may be carried out by introducing point mutations throughout the entire VH and/or VL sequence and then screening for optimized scFvs or selecting and screening for optimized scFvs. By way of example, the VH and/or VL sequence may be mutagenized by using E. coli mutator strains (as described in Low et al. 260: 359 ff J Mol Biol (1996)) or misincorporation of nucleotides by DNA polymerases as described in detail in Sambrook, Fritsch, Maniatis (1989) "A laboratory manual". Cloning, expression and selection of optimized variants of scFv molecules can be carried out by phage display or by the frequently used ribosome display technology (as described in EP 0 975 748 A1). Optimized versions are expressed in suitable vector/E. coli systems to screen for improved scFv candidates.

Suitable methodology as described above under Example 2.4 was applied to optimize a representative scFv lead (scFv A), resulting in a class of monoclonal human anti-GM-CSF neutralizing antibody fragments represented by scFv molecules B-N. The characteristics of these scFv molecules will be elucidated and described further in the following examples. The generation of monoclonal IgG molecules from the selected scFv molecules is described in the following example.

Example 3

Cloning and Eukaryotic Expression of Monoclonal Antibodies from the Selected scFvs Although bacteria are known to express functional Fab fragments, they are usually not capable of producing complete functional immunoglobulins. For the production of complete functional antibodies, mammalian cells must be used and therefore the VL region of scFv 5-306 and different VH regions of scFv molecules selected in the previous examples were subcloned into mammalian expression vectors (especially VH regions of scFv A and scFv B).

Example 3.1

Cloning of the Human Light Chain Based on scFv 5-306

To generate suitable terminal restriction sites, the DNA fragment encoding the VL region of scFv 5-306 was reamplified by PCR, resulting in Vkappa fragments with a Bsu36I-site at the 5'-end and a Xho I-site at the 3'-end. This fragment was then subcloned into the plasmid BSPOLL by Bsu36I and XhoI using the 5'-primer (5'-ACGTCACCTTAGGTGTC-CACT CCGATATCCAGATGACCCAGTCTC-CATCTTCCGTGTCTGC-3') and the 3'-primer (5'-CATG-CACTCGAGCTTGGTCCCTCCGCCGAAAG-3'), thus adding a mammalian leader sequence and a human Ckappa constant region and verified by sequencing. Utilizing EcoRI and SalI, 5-306 VL-Ckappa DNA was excised from BSPOLL and subcloned into the eukaryotic expression vector pEF-ADA derived from the eukaryotic expression vector pEF-DHFR (Mack et al. (1995) Proc. Natl. Acad. Sci. USA. 92, 7021-5) by replacing the cDNA encoding murine dihydrofolate reductase (DHFR) with that encoding murine adenosine deaminase (ADA).

Example 3.2

Cloning of Human Heavy Chain Variable Domains

From different human VH regions selected in the previous examples (especially VH regions of scFv A and scFv B), the variable region was reamplified by PCR, generating Bsu36I restriction sites at both ends. For all constructs the combination of two primers was used: 5'-primer VH-Bsu36I (5'-ACGTCACCTTAGGTGTCCACTCCCAGGT-GCAGCTGGT CCAGTCTGGGGCT GAGGTGAAGAAGC-3') and 3'-primer (5'-ACGTCACCT-GAGGAGACGGTGACCATTGTC CCTTG-3'). The resulting DNA-fragments were then subcloned using these restriction sites into the eukaryotic expression vector pEF-DHFR already containing a eukaryotic leader sequence and a DNA-fragment encoding the human IgG1 heavy chain constant region. The heavy chain variable regions were thus inserted between the leader and the heavy chain constant region. The correct sequences of the variable regions were confirmed by sequencing.

Example 3.3

Conversion of scFv Fragments into Full Human IgGs

Plasmid encoding for the light chain (VL 5-306/Ckappa) and plasmid encoding for one heavy chain (VH/human IgG1 constant region) were cotransfected into HEK cells according to standard protocols for transient protein expression and the cells were cultured to allow the expression and production of the immunoglobulins into the culture medium. In this manner, IgG A, deriving from scFv A and IgG B, deriving from scFv B were produced. After the respective production period, the supernatants were harvested and the human immunoglobulins were isolated via Protein A chromatography according to standard protocols for the purification of immunoglobulins. Purified immunoglobulins were then used for further characterization experiments.

Example 3.4

Reconversion of IgGs Specifities into scFv Fragments

VH regions from the IgG constructs (IgG A and IgG B, as described above) were recloned into a suitable scFv expression vector according to standard protocols and were operatively coupled via a flexible linker to the VL region stemming from the human light chain of Example 3.1. These constructs were produced solubly in the periplasm of E. coli as described above. The characterization of these scFvs (scFv O, derived from IgG A, and scFv P, derived from IgG B) is described in the following examples.

Example 4

Evaluation of Binding Specificity of a Human Monoclonal Anti-GM-CSF Antibody for Primate and Human GM-CSF The aim of this experiment was to show that an antibody obtained as set out above binds specifically to GM-CSF.

Therefore the binding of such an antibody to different recombinant human ("rh") colony-stimulating factors (rhG-CSF and rhM-CSF, Strathmann) was compared to the same antibody's binding to rhGM-CSF by ELISA.

50 µL of the particular antigen (1 µg/mL in PBS) were coated onto an ELISA plate (Nunc, Maxisorp) for 1 h at room temperature. After washing 3 times with PBS/0.05% Tween 20 the wells were blocked with 200 µL PBS/3% non-fat dry milk powder per well for 1.5 h at room temperature followed by washing 3 times with PBS/0.05% Tween 20. 50 µL/well of a series of human antibodies (for example IgG A and IgG B), each with identical light chains of sequence according to SEQ ID NO. 34 but with different heavy chains according to SEQ ID NOs. 35-48 were added in a dilution series ranging from 1 µg/mL to 0.5 ng/mL (in PBS/0.05% Tween 20/3% non-fat dry milk powder) and incubated for 1 h. After 3 washes with PBS/0.05% Tween 20, bound antibody was detected using 50 µL of a horseradish-peroxidase-conjugated goat anti-human IgG antibody (Dianova; 1:1000 diluted in PBS/0.05% Tween 20/3% non-fat dry milk powder). The signal was developed by addition of 50 µL/well ABTS solution (Roche) and absorption was measured at 405 nm using a wavelength of 450 nm as a reference.

Commercially available rabbit antibodies (Strathmann Biotech AG) specific for rhM-CSF and rhG-CSF, respectively, were used as positive controls for binding of these antigens, said binding being detected with an alkaline phosphatase-conjugated goat anti-rabbit antibody. The signal was developed with 50 µL/well pNpp-solution (Sigma) and absorption was measured at 405 nm using a wavelength of 450 nm as a reference.

The results are shown in FIGS. 6A, 6B and 6C for two representative human antibodies, IgG A and IgG B.

As can be seen in FIG. 6A, increasing concentration of titrated antibody led to an increase in absorption, indicating good binding to rhGM-CSF for both representative antibodies IgG A and B. FIG. 6B shows the results of the same two representative antibodies binding to rhM-CSF. As can be seen in this figure, increasing concentrations of a rabbit anti-rhM-CSF antibody led to increasing absorption, i.e. increasing binding of this control antibody (solid dots), whereas the two representative antibodies described above (solid squares and solid triangles) are superimposed as a continuing baseline absorbance which does not increase with increasing test antibody concentration. A completely analogous result is seen for both control antibody as well as representative test IgGs A and B in FIG. 6C, showing the results of binding to rhG-CSF.

Taken together, the data shown in FIGS. 6A, 6B and 6C indicate that the two representative test antibodies IgGs A and B specifically bind to rhGM-CSF, but not to other colony stimulating factors such as M-CSF and G-CSF. Such antigen binding specificity is important for a promising antibody therapeutic agent.

Example 5

Characterization of Binding Data for Human Monoclonal Anti-GM-CSF Antibodies and Fragments Thereof It was desired to generate a qualitative ranking of various members identified as positive binders of rhGM-CSF by ELISA as described above in Example 2. The ranking was intended to reflect kinetic (off-rate) and equilibrium (affinity) parameters of various representative antibody binders so identified. To this end, surface plasmon resonance (SPR) was performed on the BIAcore™ 2000 apparatus, Biacore AB (Uppsala, Sweden) with a flow rate of 5 µL/min and HBS-EP (0.01 M HEPES, pH 7.4, 0.15 M NaCl, 3 mM EDTA, 0.005% surfactant P20) as running buffer at 25° C. Recombinant human GM-CSF (Leukine, Berlex, hereinafter alternately referred to as "the antigen" or "rhGM-CSF") produced in yeast was immobilized onto flow cells 2-4 on a CM5 sensor chip. The chip surface was activated by injecting 80 µL of 0.1 M sodium-hydroxysuccinimide, 0.4 M N-ethyl-N'(3-dimethyl aminepropyl)-carbodiimide (NHS/EDC). The antigen was coupled by manual injection of 10 µg/mL rhGM-CSF in 0.01 M sodium-acetate, pH 4.7. Different densities of antigen were immobilized on flow cells 2-4 adjusting the amount of manual injection times. Flow cell 1 was left unmodified while flow cell 2 was coated with the highest possible density of rhGM-CSF (800 RU). Flow cell 3 was coated with 50% of the amount of antigen immobilized on flow cell 2 and flow cell 4 was coated with lowest density of rhGM-CSF (typically 10%). The activated surface of the sensor chip was blocked by injecting 85 µL of 1 M ethanolamine and the chip was left to equilibrate overnight at a constant flow rate of 5 µL/min of HBS-EP.

Example 5.1

Qualitative Determination of Kinetic Binding Parameters (Off-Rate) for scFv Fragments of Human Monoclonal Anti-GM-CSF Antibodies Biacore experiments were performed as set out in the preceding paragraph. Prior to the experiment eluted protein solutions of the periplasmic preparation ("PPP") were dialyzed against PBS at 25° C. for 2 h and diluted 1:1 in HBS-EP. Binding kinetics of the members of claimed class were measured by injecting 10 µL of purified periplasmic protein solution at 25° C. over the sensor chip. The non-specific background adsorption of protein to the unmodified sensor chip surface (FC1) was subtracted from the response signal in the rhGM-CSF immobilized flow cells (FC2, FC3, FC4). The relative response signal (FC2-1, FC3-1, FC4-1) was determined and the specific dissociation rate was monitored for 100 sec.

Figure 7A:
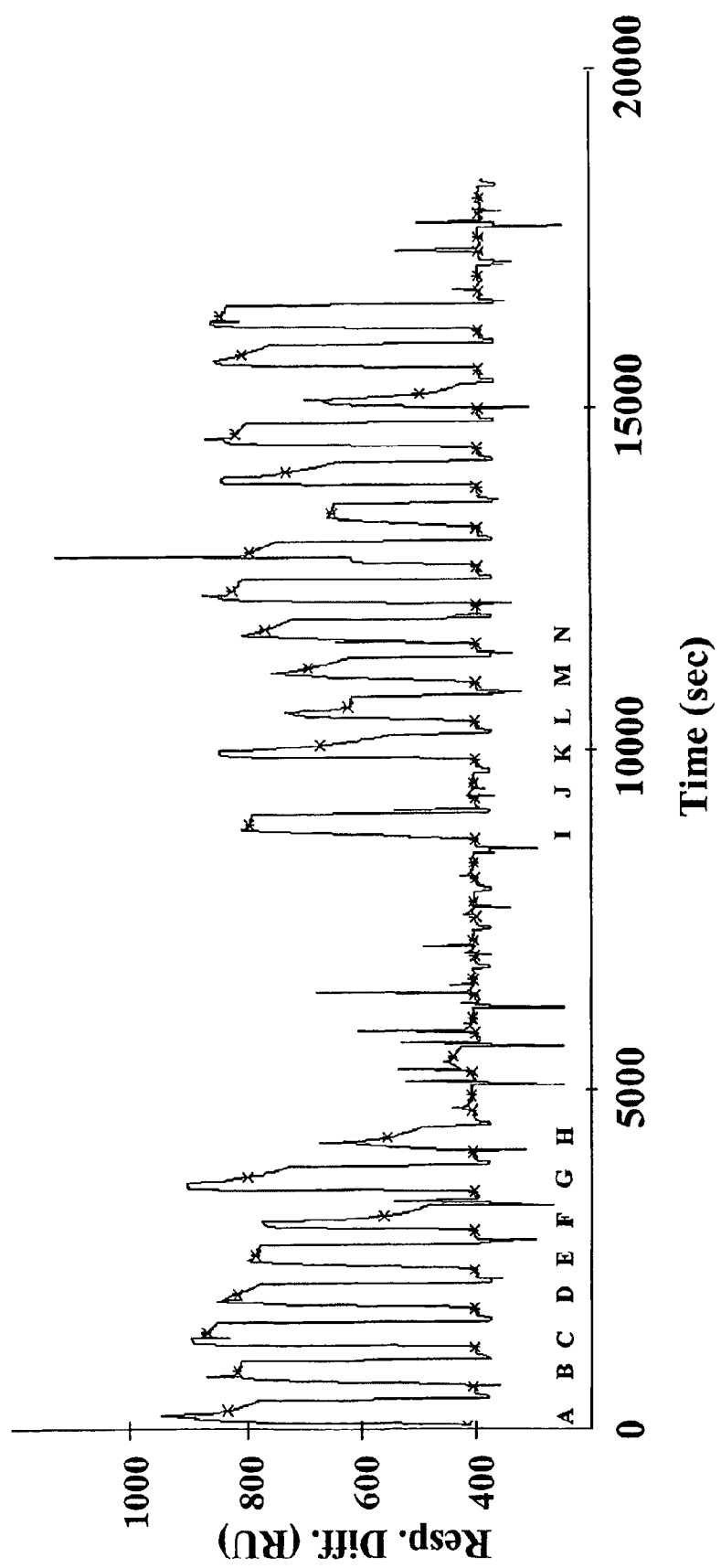

The results of these experiments are shown in FIG. 7A for a series of representative scFv fragments which had previously been identified as positive rhGM-CSF binders in ELISA experiments. Representative scFv antibody fragments for which Biacore data is shown in FIG. 7A are as follows: scFv A, scFv B, scFv C, scFv D, scFv E, scFv F, scFv G, scFv H, scFv I, scFv J, scFv K, scFv L, scFv M and scFv N.

Generally, in interpreting Biacore results, the amplitude of the binding peak (RUmax) directly correlates to the protein concentration in the injected sample. The kinetic on-rate (ka) is concentration dependent and, due to varying concentrations of protein in the PPP, cannot be used for the qualitative ranking of the members of claimed class. The kinetic off-rate (kd) is protein concentration independent and characteristic for the binding strength of the respective members of claimed class. All identified members of claimed class show specific binding to the immobilized rhGM-CSF. The members of claimed class with the best apparent off rate were identified and after further correlation of the SPR data with the inhibition data submitted for determination of affinity via equilibrium binding experiments on the BIAcore.

In examining FIG. 7A, then, one sees distinct peaks for each of representative scFv antibody fragments A-N, the upper portions of which each show a characteristic curvature which can be extrapolated to obtain an off-rate for the scFv fragment in question. Qualitatively, then, one can conclude that each of the representative scFv fragments binds well to human GM-CSF.

Example 5.2

Quantitative Determination of Equilibrium Binding Parameters (Affinity) for Certain Human Anti-GM-CSF Antibodies and ScFv Fragments Thereof Having established, qualitatively, in Example 5.1 that a number of scFv fragments of anti-GM-CSF antibodies which had previously tested positive for GM-CSF binding by ELISA demonstrate reasonable kinetic off-rates when binding to human GM-CSF, it was then desired to obtain a quantitative representation of such binding for antibodies and fragments thereof by focusing on the equilibrium binding characteristics to recombinant human GM-CSF. As shown above in Example 4, specific binding to the antigen—here rhGM-CSF—is one of the characteristic and specific attributes of the class of anti-GM-CSF antibodies and fragments thereof as claimed herein.

Binding kinetics (the off-rate, kd, and the on-rate, ka) of certain representative members of the class of human anti-GM-CSF antibodies and fragments thereof were measured by injecting 10 μL of purified protein (i.e. antibody or fragment thereof) in a dilution series ranging from 10 μg/mL to 1 pg/mL purified protein and monitoring the dissociation at 25° C. for 100 sec. The purified protein was buffered in HBS-EP. The data were fitted using BIAevalution™ software, determining the rate constant for dissociation and association kinetics with a 1:1 Langmuir binding equation (see Formulae 1 and 2 below), where A is the concentration of injected purified protein analyte and B[0] is Rmax:

$$dB/dt = -(ka*[A]*[B] - kd*[AB])$$ (Formula 1)

$$dAB/dt = -(ka*[A]*[B] - kd*[AB])$$ (Formula 2)

Figure 7B:
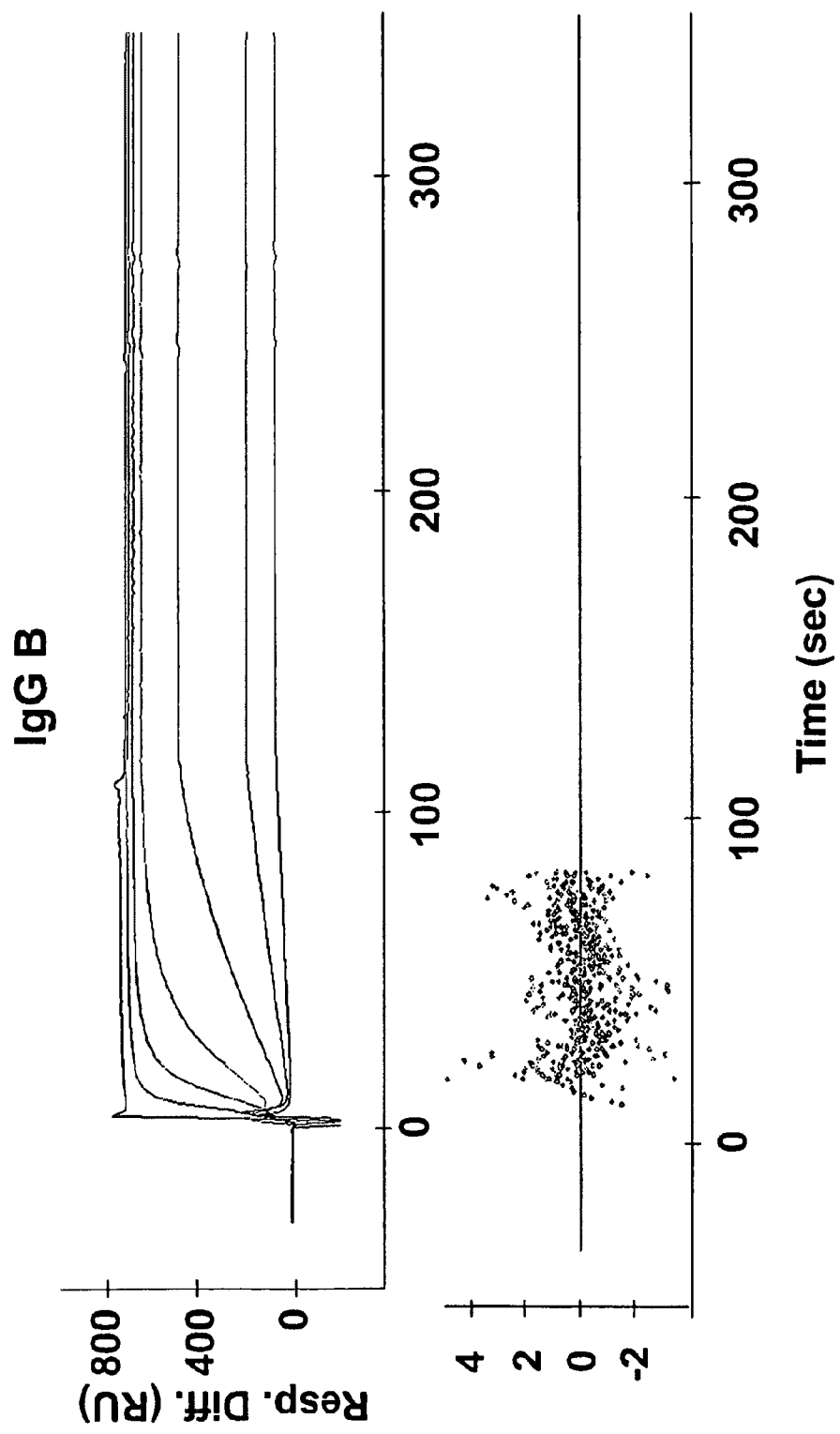
Figure 7C:
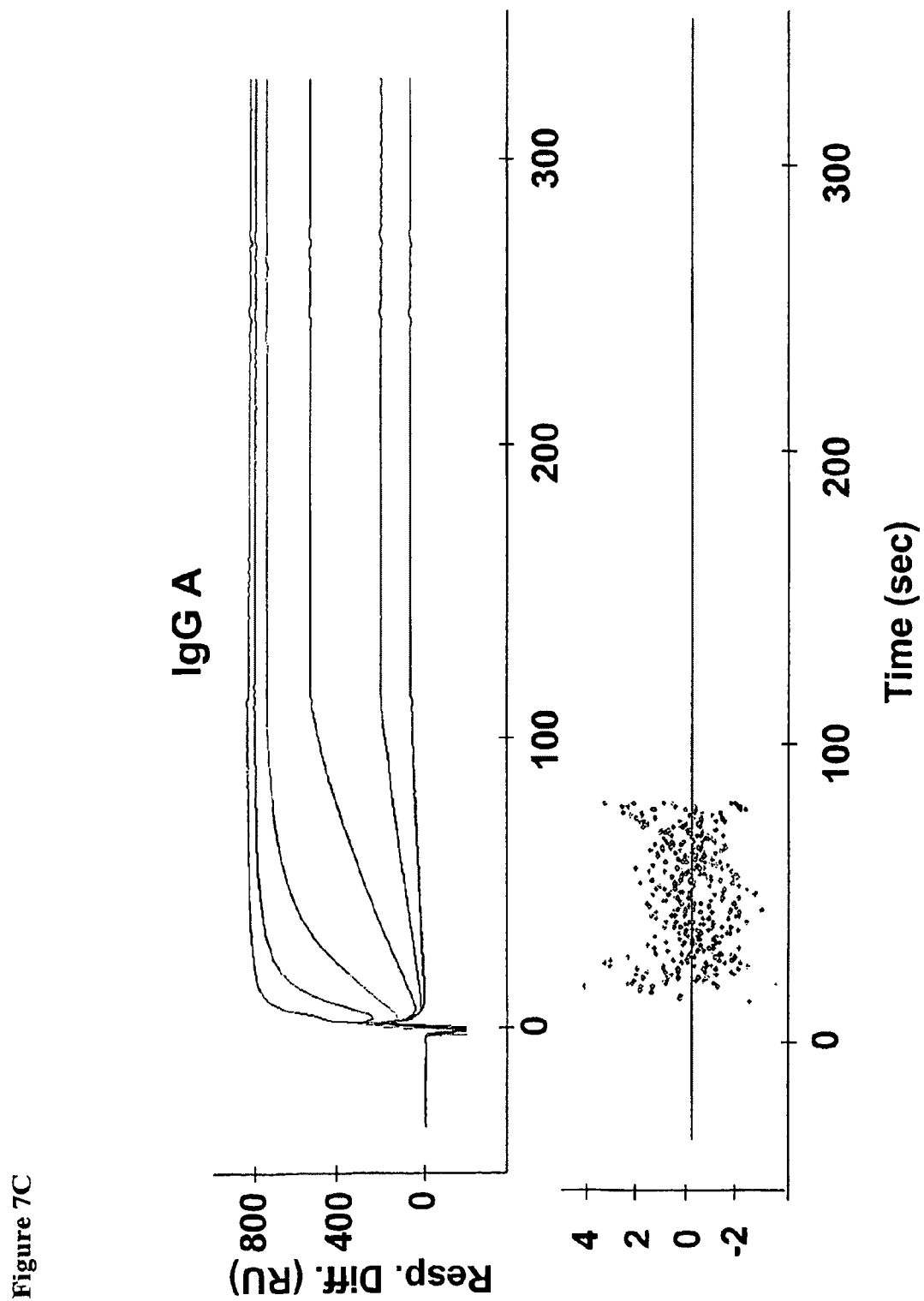
Figure 7D:
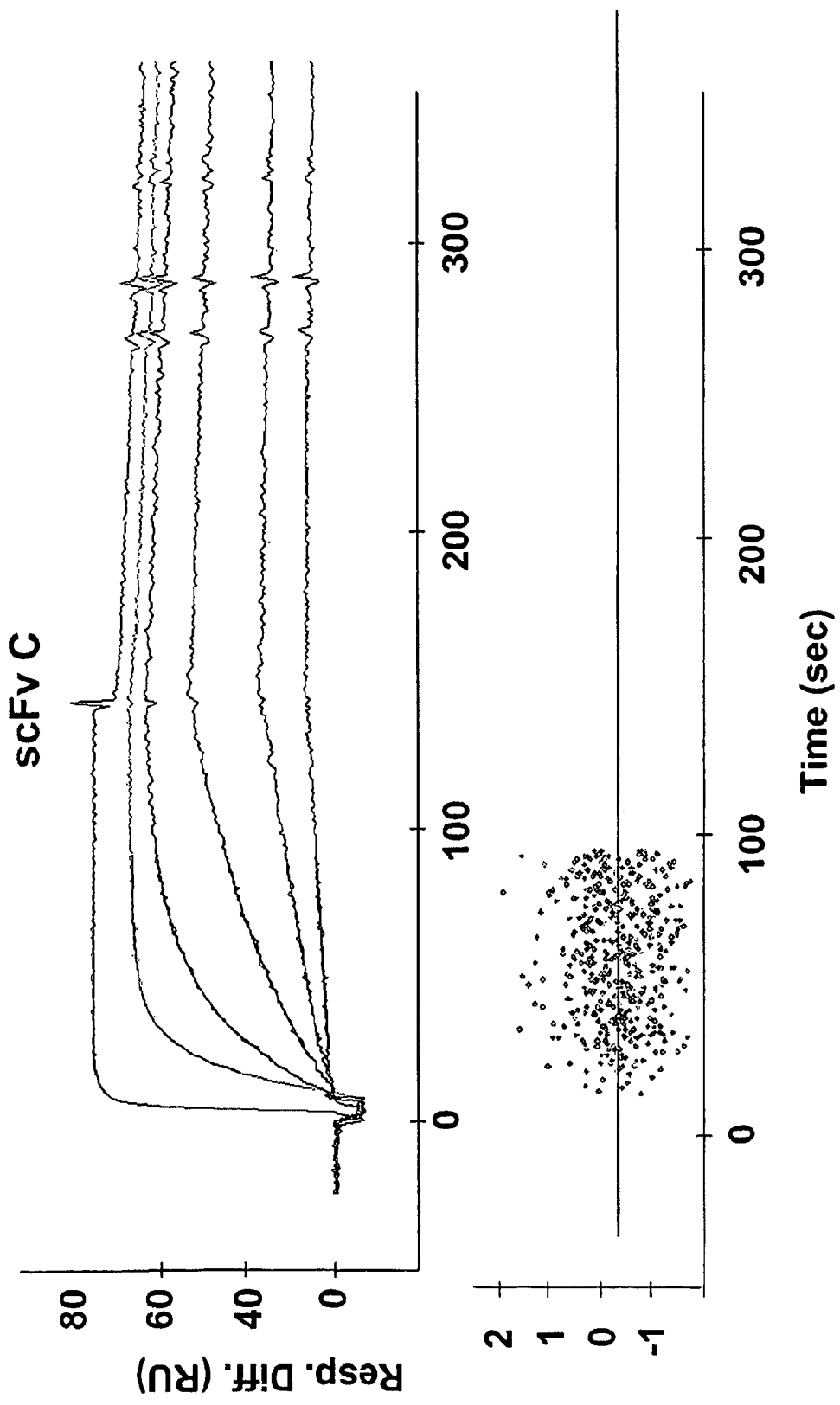
Figure 7E:
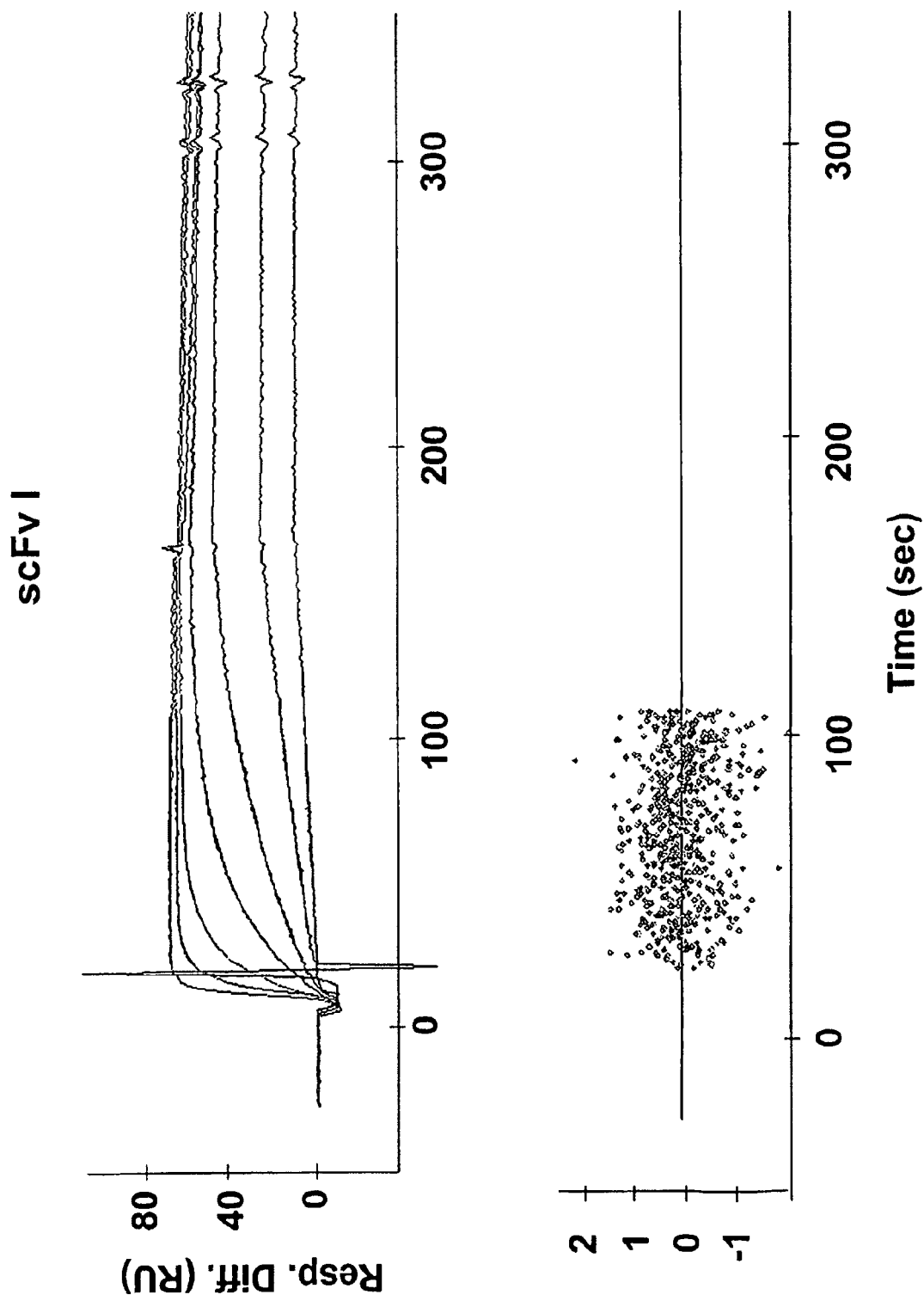
Figure 7F:
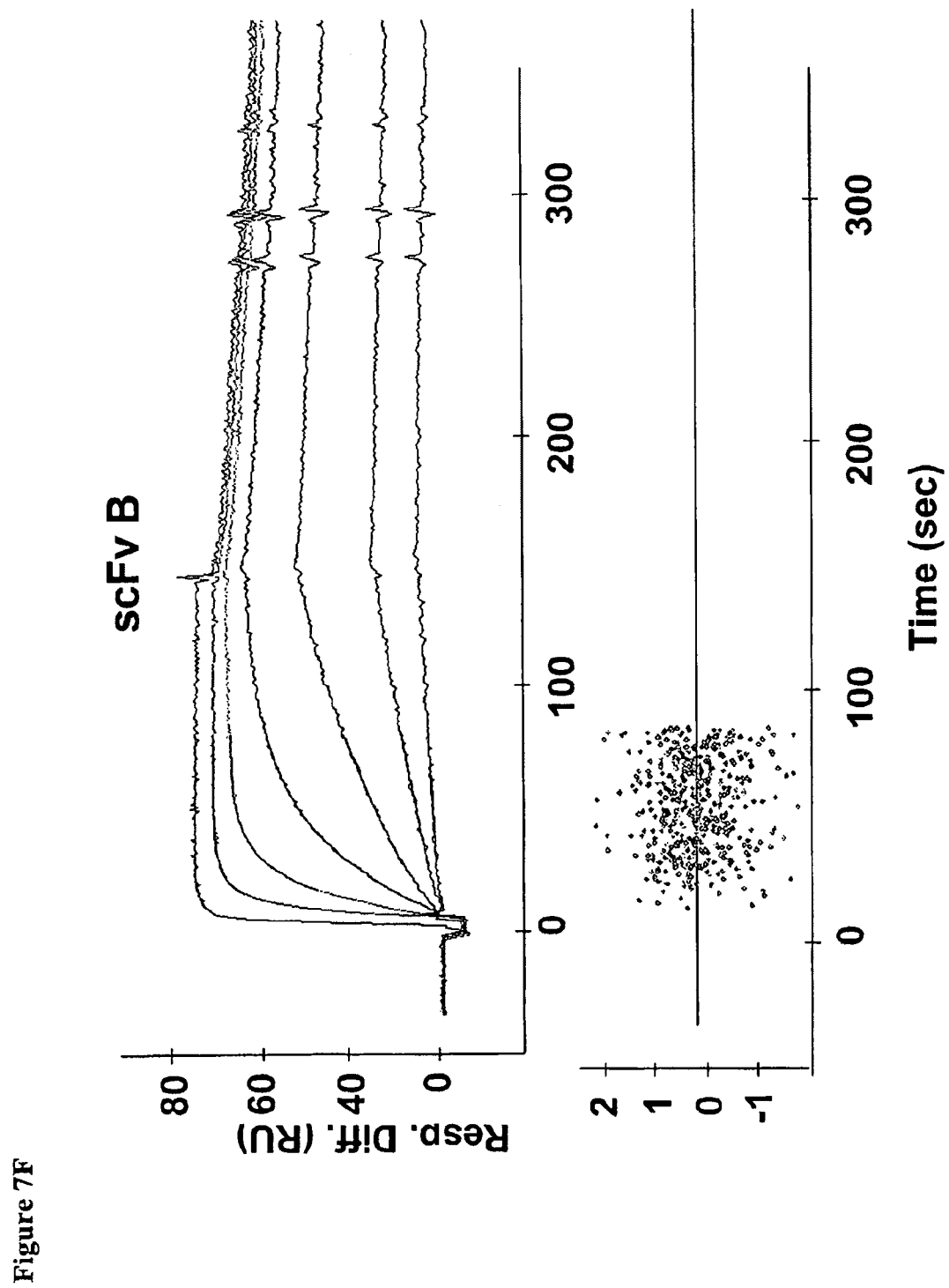
Figure 7G:
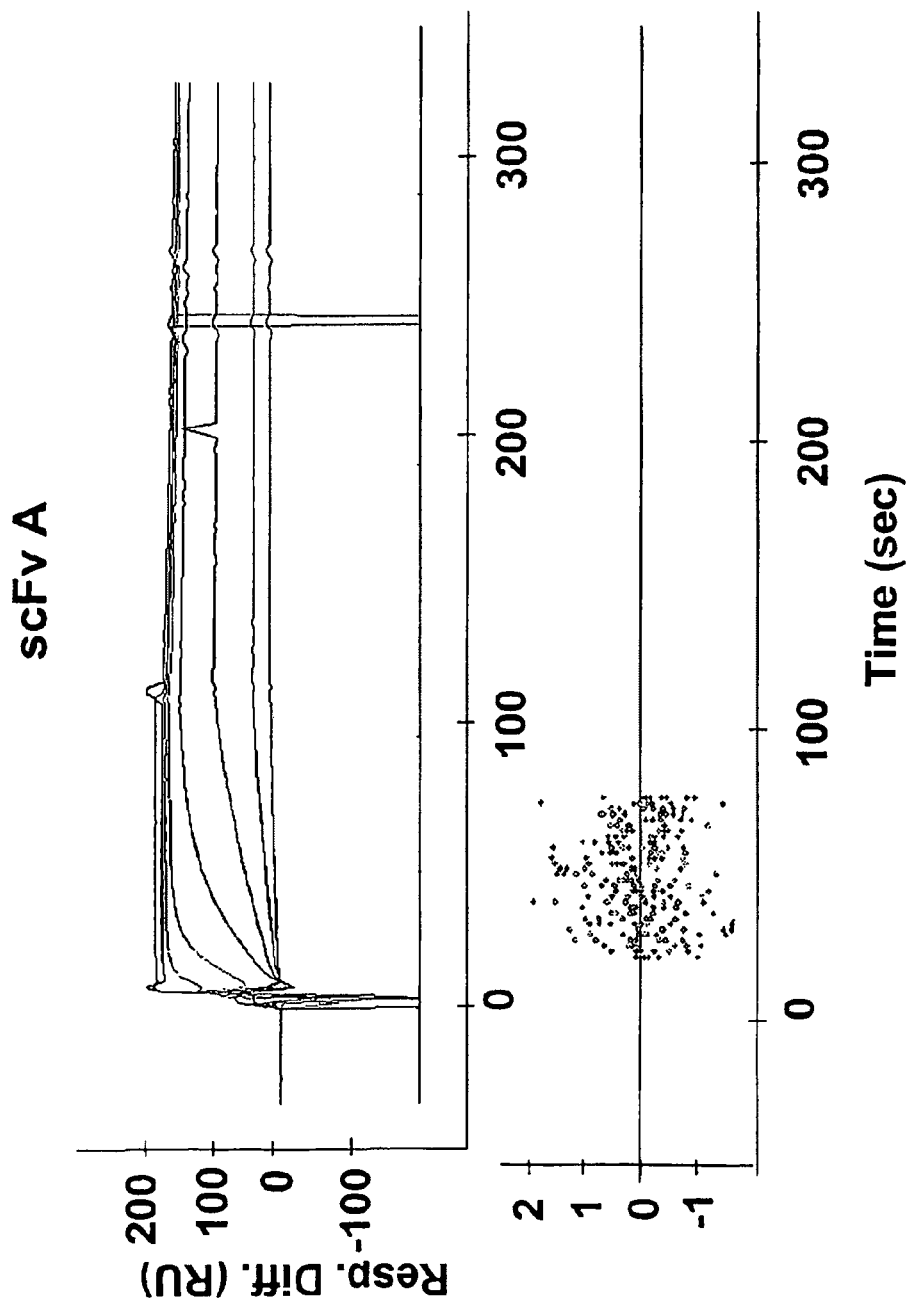
Figure 7H:
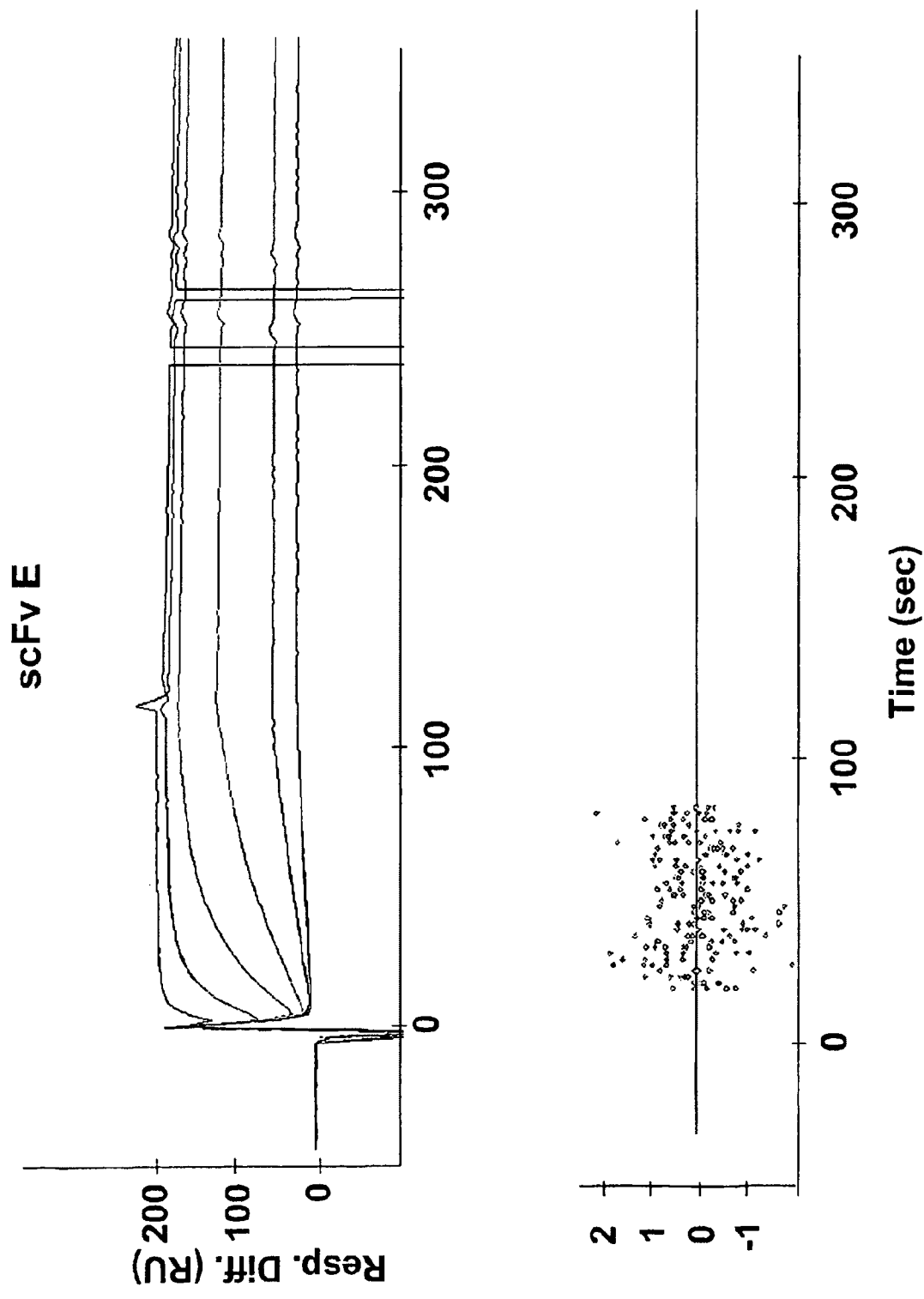
Figure 7I:
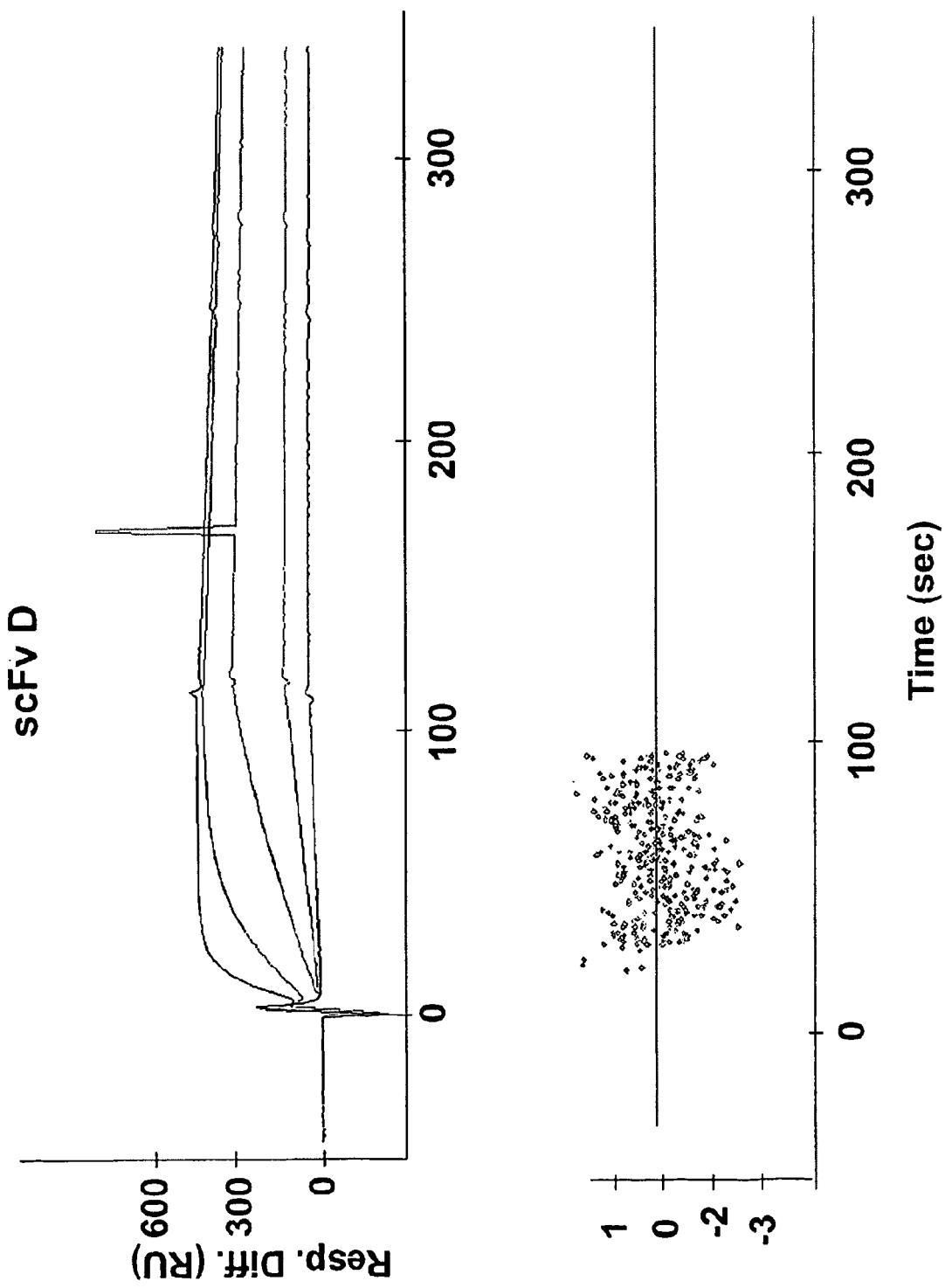

Kinetic binding curves were determined with up to 8 concentrations of each representative human anti-GM-CSF antibody or fragment thereof analyzed. The independent fitting of the raw data resulted in dissociation and association rate constants that were used to calculate the equilibrium dissociation constant (KD). The results obtained for each representative human anti-GM-CSF antibody or fragment thereof are shown in FIGS. 7B-I. Specifically, FIG. 7B shows the binding data obtained for representative IgG B; FIG. 7C shows the binding data obtained for representative IgG A; FIG. 7D shows the binding data obtained for representative scFv C; FIG. 7E shows the binding data obtained for representative scFv I; FIG. 7F shows the binding data obtained for representative scFv B, FIG. 7G shows the binding data obtained for representative scFv A; FIG. 7H shows the binding data obtained for representative scFv E; and FIG. 7I shows the binding data obtained for representative scFv D. The data are summarized below in Table 2.

Example 6

Minimal Epitope Requirements for a Certain Representative Fragment of a Human Anti-GM-CSF Antibody It was desired to determine the epitope bound by human anti-GM-CSF antibodies and fragments thereof as described and claimed herein. To this end, a peptide spotting ("pepspot") analysis was performed using scFv A as a representative member of this class of molecules and human GM-CSF as antigen.

Generally, a pepspot experiment is performed as follows. Overlapping 13mer peptides derived from the amino acid sequence of hGM-CSF (for the GM-CSF sequence of humans and certain other primates, see hereinabove as well as FIG. 8A, as well as SEQ ID NOs: 49-51) were covalently linked to a Whatman 50 cellulose membrane by the C-terminus while the acetylated N-terminus remained free. The individual 13mer peptides generated (by JPT Peptide Technologies GmbH) are shown below in Table 3. The length of the overlapping sequence of any two respective peptides was set to be 11 amino acids. According to the manufacturer's protocol the membrane was rinsed with absolute EtOH for 1 min, followed by washing with TBS and blocking with TBS/3% BSA overnight. As with every subsequent incubation and washing, the blocking was carried out at room temperature. After washing 3 times with TBS/0.05% Tween 20 for 10 min the membrane was incubated with 1 μg/mL scFv A in TBS/3% BSA for 2.5 h followed by washing carried out as before. Detection of the scFv was accomplished by using an anti-Penta-His antibody (Qiagen, 0.2 μg/mL in TBS/3% BSA) and followed by a horseradish-peroxidase-conjugated goat-anti-mouse IgG (Fc-gamma-specific) antibody (Dianova, 1:10.000 in TBS/3% BSA) the incubation with each of these respective antibodies being performed for 1 h. After washing 3 times with TBS/0.05% Tween 20 for 10 min the signal was developed by enhanced chemiluminescence (SuperSignalWest Pico Luminol/Enhancer Solution and SuperSignalWest Pico StablePeroxide Solution; Pierce) and exposition to a BioMax Film (Kodak).

Strong binding signals of scFv A to stretches of human GM-CSF were detected on a stretch of peptide-spots between spot A and B as well as on the spot C (See Table 3 below, and FIG. 8B). As can be seen in FIG. 8B, binding to other spots seemed to be of a lower strength. The stretch of spots spanning points A and B corresponds to amino acid residues 15-35. All 13mer peptides making up this region contain one minimal amino acid stretch of amino acids 23-27 (RRLLN). Spot C corresponds to amino acid residues 65-72 (GL-

TABLE 2

Quantitative affinity binding data for certain representative human anti-GM-CSF antibodies and fragments thereof

| Antibody/ fragment thereof | In Figure | ka ($s^{-1}M^{-1}$) | kd ($s^{-1}$) | KD (M) |
|---|---|---|---|---|
| scFv A | 7G | 4.41exp5 ± 3.00exp5 | 1.84exp-3 ± 6.55exp-4 | 4.17exp-9 |
| scFv B | 7F | 1.01exp6 ± 4.08exp5 | 8.07exp-4 ± 3.73exp-5 | 7.98exp-10 |
| scFv E | 7H | 1.26exp6 ± 5.57exp4 | 2.55exp-4 ± 8.12exp-5 | 2.03exp-9 |
| scFv C | 7D | 1.73exp5 ± 8.23exp4 | 4.77exp-4 ± 1.91exp-4 | 2.76exp-9 |
| scFv D | 7I | 7.60exp5 ± 6.70exp5 | 8.66exp-4 ± 2.13exp-4 | 1.14exp-9 |
| scFv I | 7E | 2.32exp6 ± 2.13exp5 | 3.47exp-4 ± 8.78exp-5 | 1.50exp-9 |
| IgG A | 7C | 2.09exp6 ± 1.32exp6 | 1.81exp-4 ± 8.77exp-5 | 8.70exp-11 |
| IgG B | 7B | 3.63exp5 ± 2.40exp5 | 1.68exp-5 ± 5.74exp-6 | 4.64exp-11 |

RGSLTKLKGPL) of human GM-CSF. These findings implicate that scFv A likely recognizes a discontinous epitope.

In the secondary structure of human GM-CSF amino acids 15-35 are situated in helix A while residues corresponding to spot C are part of a loop-structure located between helices C and D. A three-dimensional model of folding of the molecule reveals close sterical proximity of these sites with respect to one another.

The minimal amino acid sequence motif in the peptides of spots A-B corresponds to residues 23-27 of human GM-CSF (RRLLN). An increasing signal strength from spot A to B can be explained by the better accessibility of the RRLLN epitope in peptide corresponding to spot B than in the peptide corresponding to spot A. In Peptide A the epitope is located directly at the C-terminus that is linked to the membrane while in peptide B it is located at the more accessible N-terminus of the peptide.

TABLE 3

Sequences of overlapping 13mer peptides immobilized on the cellulose membrane.

| 1. | APARSPSPSTQPW |
| 2. | ARSPSPSTQPWEH |
| 3. | SPSPSTQPWEHVN |
| 4. | SPSTQPWEHVNAI |
| 5. | STQPWEHVNAIQE |
| 6. | QPWEHVNAIQEAR |
| 7. | WEHVNAIQEARRL |
| 8. | HVNAIQEARRLLN (A) |
| 9. | NAIQEARRLLNLS |
| 10. | IQEARRLLNLSRD |
| 11. | EARRLLNLSRDTA |
| 12. | RRLLNLSRDTAAE (B) |
| 13. | LLNLSRDTAAEMN |
| 14. | NLSRDTAAEMNET |
| 15. | SRDTAAEMNETVE |
| 16. | DTAAEMNETVEVI |
| 17. | AAEMNETVEVISE |
| 18. | EMNETVEVISEMF |
| 19. | NETVEVISEMFDL |
| 20. | TVEVISEMFDLQE |
| 21. | EVISEMFDLQEPT |
| 22. | ISEMFDLQEPTSL |
| 23. | EMFDLQEPTSLQT |
| 24. | FDLQEPTSLQTRL |

TABLE 3-continued

Sequences of overlapping 13mer peptides immobilized on the cellulose membrane.

| 25. | LQEPTSLQTRLEL |
| 26. | EPTSLQTRLELYK |
| 27. | TSLQTRLELYKQG |
| 28. | LQTRLELYKQGLR |
| 29. | TRLELYKQGLRGS |
| 30. | LELYKQGLRGSLT |
| 31. | LYKQGLRGSLTKL |
| 32. | KQGLRGSLTKLKG |
| 33. | GLRGSLTKLKGPL (C) |
| 34. | RGSLTKLKGPLTM |
| 35. | SLTKLKGPLTMMA |
| 36. | TKLKGPLTMMASH |
| 37. | LKGPLTMMASHYK |
| 38. | GPLTMMASHYKQH |
| 39. | LTMMASHYKQHSP |
| 40. | MMASHYKQHSPPT |
| 41. | ASHYKQHSPPTPE |
| 42. | HYKQHSPPTPETS |
| 43. | KQHSPPTPETSSA |
| 44. | HSPPTPETSSATQ |
| 45. | PPTPETSSATQTI |
| 46. | TPETSSATQTITF |
| 47. | ETSSATQTITFES |
| 48. | SSATQTITFESFK |
| 49. | ATQTITFESFKEN |
| 50. | QTITFESFKENLK |
| 51. | ITFESFKENLKDF |
| 52. | FESFKENLKDFLL |
| 53. | SFKENLKDFLLVI |
| 54. | KENLKDFLLVIPF |
| 55. | NLKDFLLVIPFDS |
| 56. | KDFLLVIPFDSWE |
| 57. | FLLVIPFDSWEPV |
| 58. | LVIPFDSWEPVQE |

Example 7

Neutralization Potency of Certain Human Anti-Human GM-CSF Antibodies/Antibody Fragments

Example 7.1

Qualitative Evaluation of Neutralization Potential of Certain Representative Human Anti-Human GM-CSF Antibodies and Fragments Thereof The aim of this experiment is to achieve qualitative information on the neutralizing activity of representative human anti-GM-CSF neutralizing antibodies and fragments thereof. To this end, the human GM-CSF-dependant cell line TF-1 (DSMZ, ACC 334) was used. The rate of proliferation of this cell line depends on the presence of human GM-CSF, so that measuring cell growth following incubation of cells with human GM-CSF with and without an antibody suspected of having GM-CSF-neutralizing activity may be used to determine whether such neutralization activity in fact exists.

TF-1 cells were cultivated in RPMI 1640 medium (Gibco; L-glutamine, phenol-red free), 10% heat inactivated FCS in the presence of 2.5 ng/mL rhGM-CSF as described by the distributor (Deutsche Sammlung von Mikroorganismen and Zellkulturen GmbH, Braunschweig, Germany). Cells were grown to a cell density of 0.5×10exp6 cells/mL. For the proliferation assay TF-1 cells were harvested by centrifugation at 300×g for 4 min and washed with 1×PBS (Dulbecco's, Gibco). Cells were resuspended to a final concentration of 1×10exp5 cells/mL in RPMI 1640, 10% FCS and 90 μL cell suspension per Microtest flat bottom cell culture plate well were used (0.9×10exp4 cells/well). A final concentration of 0.3 ng/mL rhGM-CSF was used to stimulate the proliferation of the TF-1 cells. For neutralization of GM-CSF dependent proliferation purified PPP of representative fragments of a human anti-GM-CSF antibody were dialyzed against 1×PBS at 25° C. for 2 h. 10 μl of dialyzed and sterile filtered protein solution (0.22 μm filter) were added to 100 μl solution containing TF-1 and rhGM-CSF.

After incubation for 72 h at 37° C. at 5% $CO_2$ the proliferative status of the TF-1 cells was determined with a colorimetric assay based on the cleavage of tetrazolium salts (WST-1, Roche) by mitochondrial dehydrogenase in viable cells. The formazan dye formed by metabolically active cells was quantitated by measuring its absorbance with an ELISA reader at 450 nm The inhibition of the human GM-CSF-dependant proliferation of TF-1 cells by the tested representative fragments of human anti-human GM-CSF antibody fragments was varying in strength (FIG. 9). While two such fragments did not have a neutralizing effect (scFv F and scFv L); five constructs (scFv J, scFv K, scFv M, scFv N, and scFv H) showed intermediate inhibition and seven constructs (scFv B, scFv I, scFv E, scFv D, scFv G, scFv C, scFv A) showed strong inhibition of the GM-CSF dependant proliferation of TF-1 cells. The lack or lower degree of neutralizing effect could be due to a lower expression level of the particular representative scFv or to a less stable complex formed between a particular representative scFv and rhGM-CSF over the incubation period of 72 h at 37° C.

Example 7.2

Quantitative Evaluation of Neutralization Potential of Certain Representative Human Anti-Human GM-CSF Antibodies and Fragments Thereof, as Measured by Cell Proliferation Selected representative scFv molecules shown above to exhibit strong inhibition of TF-1 proliferation were then subjected to a quantitative analysis of neutralizing efficacy. To this end, the same human GM-CSF-dependant cell line TF-1 (DSMZ ACC 334) was used. TF-1 cells were cultivated and prepared for the proliferation assay as described in detail in Example 7.1 above. A final concentration of 0.3 ng/mL rhGM-CSF was used to stimulate the proliferation of the TF-1 cells. For neutralization of GM-CSF-dependent proliferation 10 μl of purified samples of representative human anti-human GM-CSF neutralizing monoclonal antibodies or fragments thereof were added to a solution containing 100 μl TF-1 and rhGM-CSF in a dilution series. Final protein concentrations ranged from 10 μg/ml to 10 pg/ml.

Samples were incubated at 37° C. at 5% $CO_2$ for 72 h. After 72 h the proliferative status of the TF-1 cells was determined as described in Example 7.1 above. The data were fitted for half maximal inhibition of proliferation ($IC_{50}$) using the non-linear regression curve fit of the Prism software.

The clear GM-CSF neutralizing effect seen in the qualitative proliferation-inhibition experiment described in Example 7.1 above could be confirmed and quantified. All tested scFv fragments of human anti-human GM-CSF monoclonal neutralizing antibodies displayed a half maximal inhibition constant ($IC_{50}$) in the nanomolar range in this proliferation-inhibition experiment. A clear ranking in neutralizing efficacy could be established, as is seen in FIG. 10A.

The tested human anti-human GM-CSF monoclonal neutralizing IgG antibodies display a significantly higher neutralizing efficacy than their scFv counterparts. The half maximal inhibition constant of the IgG molecules generated in this experiment was in the sub-nanomolar range. As can be seen in FIG. 10B, the $IC_{50}$ evaluated for IgG A was 0.9 nM and IgG B had an IC50 of 0.3 nM.

In order to check whether the scFv antibody fragments generated from IgGs A and B (scFvs O and P, respectively) quantitatively correspond in their neutralization potential to scFvs A and B, analogous TF-1 neutralization assays were performed as described above except using scFvs O and P as test molecules. The results are shown in FIGS. 10C and 10D for scFvs P and O, respectively. As can be seen from FIG. 10D, scFv O has the same neutralization potential as scFv A, showing that reconversion from IgG back to scFv format is possible without loss of biological activity.

Example 7.3

Quantitative Evaluation of Neutralization Potential of Certain Representative Human Anti-rhGM-CSF Antibodies and Fragments Thereof, as Measured by Reduced IL-8 Production This experiment was performed to quantify the neutralization activity of representative human anti-human GM-CSF antibodies and fragments thereof by measuring GM-CSF-dependent IL-8 production by U-937 cells. The GM-CSF antigen used in the foregoing experiments was rhGM-CSF. The monocytic U-937 cells were cultivated in RPMI 1640 medium Gibco (L-glutamine, phenol-red free) supplemented with 10% heat inactivated FCS as described by the distributor (Deutsche Sammlung von Mikroorganismen and Zellkulturen GmbH, Braunschweig, Germany). Cells were grown to a cell density of 1×10exp6 cells/mL.

In performing the inhibition assay based on measurement of IL-8 production, cells were harvested by centrifugation at 300×g for 4 min and resuspended to a final concentration of 1×10exp6 cells/mL in RPMI 1640, 10% FCS. 1.8×10exp5 cells/well (180 μL cell suspension) were seeded per Microtest flat bottom cell culture plate well. A final concentration of 1 ng/mL rhGM-CSF was used to stimulate IL-8 production by the U-937 cells. 20 μl of purified scFv or IgG was added to 180 μl U937 cells and rhGM-CSF solution in a dilution series resulting in final protein concentrations ranging from 10 μg/mL to 10 pg/mL After incubation for 18 h at 37° C. and 5% $CO_2$ cells were spun down by centrifugation of culture plates for 2 min at 600×g. Culture supernatants were harvested by pipetting to a new plate and were analyzed to determine the concentration of IL-8 therein using the OptEIA Human IL-8 ELISA Set (Becton Dickenson and Company).

ELISA detection was carried out according to the manufacturer's instructions. In brief, 50 μL of capture antibody diluted in 0.1 M sodium carbonate, pH 9.5 were coated onto a microtest plate over night at 4° C. After washing 3 times with PBS/0.05% Tween 20 the wells were blocked with 200 μL PBS/10% FCS per well for 1 h at room temperature followed by washing 3 times with PBS/0.05% Tween 20. Then 50 μL of the culture supernatant samples were added to the wells and incubated for 2 h at room temperature. For later quantification of the IL-8 concentration a serial dilution of the IL-8 standard provided by the manufacturer was carried along through the procedure.

After washing 5 times with PBS/0.05% Tween 20 detection was carried out using 50 μL of the Working Detector (Detection Ab+Av-HRP) provided in the OptEIA Human IL-8 ELISA Set. After a 1 h incubation at room temperature, wells were washed an additional 7 times. The signal was developed by adding OPD substrate solution (Sigma) and was detected at a wavelength of 490 nm (using a reference wavelength of 620 nm).

An IL-8 standard curve was plotted for calibration and IL-8 concentration in the culture supernatant samples was calculated according to this calibration curve. The data were fitted for half maximal inhibition of IL-8 production ($IC_{50}$) using the non-linear regression curve fit of the Prism software.

All representative fragments of human anti-rhGM-CSF monoclonal neutralizing antibodies tested showed clear inhibition of the GM-CSF dependent IL-8 production of U-937 cells, as can be clearly seen by the decrease in IL-8 concentration with increasing scFv concentration in FIG. 11. The ranking in neutralizing efficacy seen in this experiment is in accordance with the ranking obtained testing the same molecules for their neutralizing effect in the TF-1 proliferation-inhibition experiment described above.

It will be noted that the $IC_{50}$ values determined in this experiment are higher as compared to those obtained for the same molecules in the previous TF-1 proliferation experiment. This is due to the higher GM-CSF concentration required for stimulation of IL-8 production by U-937 cells than required for stimulation of TF-1.

Example 7.4

Quantitative Evaluation of Neutralization Potential of Representative Human Anti-Human GM-CSF Antibodies and Fragments Thereof on Recombinant Macacan GM-CSF, as Measured by Cell Proliferation The aim of this experiment was to show the neutralizing potency of representative human anti-human GM-CSF antibodies and fragments thereof for GM-CSF from non-human primates of the Macaca family ("macGM-CSF").

To show the neutralizing effect of selected scFv and IgG molecules on macGM-CSF, a proliferation-inhibition experiment was performed according to the protocol described in Examples 7.1 and 7.2 using macGM-CSF instead of hGM-CSF. Both hGM-CSF and macGM-CSF stimulate the proliferation of TF-1 cells with the same half maximal efficacy ($EC_{50}$). A final concentration of 3 ng/ml macGM-CSF was used to stimulate the proliferation of the TF-1 cells in the experiment testing the scFv molecules and 0.3 ng/mL rhGM-CSF cells in the experiment testing IgG B as a representative human anti-human GM-CSF antibody. In order to neutralize the proliferation of the TF-1 cells, 10 μl of purified human anti-human GM-CSF antibody or fragment thereof were added to 100 μl TF-1 and macGM-CSF solution in a dilution series. Final protein concentrations ranged from 10 μg/ml to 10 pg/ml. Samples were incubated at 37° C. at 5% $CO_2$ for 72 h. After 72 h the proliferative status of the TF-1 cells was determined as described in Examples 7.1 and 7.2. The data were fitted for half maximal inhibition of proliferation ($IC_{50}$) using the non-linear regression curve fit of the Prism software.

As seen in FIG. 12A, certain representative human anti-human GM-CSF monoclonal antibody fragments also exhibited a clear neutralization potential of mac GM-CSF (scFv B, scFv E, scFv C, scFv I, scFv A). Furthermore, as can be seen in FIG. 12B, increasing concentrations of the representative human anti-human GM-CSF monoclonal antibody IgG B clearly led to a decrease in TF-1 proliferation, demonstrating this antibody's neutralizing potential. Interestingly, the $IC_{50}$ value generated for IgG B in this experiment (0.3 nM) using mac GM-CSF for induction of TF-1 cell proliferation is equal to the one generated in the experiment using hGM-CSF, showing a clear cross-reactivity of IgG B for GM-CSF in these species.

Example 8

Cross-Reactivity of IgG B with GM-CSF from Various Species

The cross-reactivity of IgG B with GM-CSF from various non-human species was investigated to identify species suitable for later in vivo studies. In a first set of experiments, binding of IgG B to commercially available recombinant GM-CSF from human (Leukine®, Berlex), pig, dog, rat (R&D Systems, Wiesbaden, Germany) and mouse (Strathmann Biotech, Hamburg, Germany) was tested in an ELISA experiment. Specifically, an ELISA-plate was coated with 1 μg/mL GM-CSF from the various species mentioned. IgG B was added in a dilution series and was detected using a horseradish-peroxidase-conjugated anti-human IgG1 antibody. The ELISA was developed by adding OPD o-phenylendiamine ("OPD", yellow-orange when reacted with peroxidase) substrate solution (Roche, Germany) and measured at 490 nm As seen in FIG. 13, IgG B showed robust binding to recombinant human GM-CSF, while GM-CSF from the other species tested was not recognized. Pig, dog, rat or mouse may therefore not be suitable species for in vivo testing. However, as seen above in Example 7.4, IgG B shows a marked cross-reactivity with macGM-CSF (from cynomolgus monkey, *macaca fascicularis*), implying the suitability of at least one monkey species from the macacan family for in vivo studies of IgG B.

Example 9

Binding by IgG B to Differently Glycosylated Variants of GM-CSF

The aim of this experiment was to determine the extent to which the binding of IgG B to GM-CSF depends on the latter's glycosylation pattern. To this end, a dilution series of conditioned medium containing natural hGM-CSF (human glycosylation), as well as recombinant hGM-CSF from *E. coli* (no glycosylation) and yeast (yeast glycosylation), as well as recombinant macaque GM-CSF were tested for their potency to induce TF-1 proliferation.

Human glycosylated GM-CSF was obtained from the culture supernatant of IL-1,β-treated BEAS-2B cells (human lung cells obtained from ATCC CRL-9609). BEAS-2B cells were propagated in BEBM-Medium substituted with the BEGM Bullet Kit (Cambrex, Verviers, Belgium) but cultured in RPMI 1640, 10% FCS in the presence of 50 ng/mL IL-1β (Strathmann Biotech, Hamburg, Germany) for induction of GM-CSF production. After 48-hour incubation at 37° C., 5% $CO_2$ the culture supernatant was analyzed for its GM-CSF content using the OptEIA Human GM-CSF Elisa Set (BD Biosciences, Heidelberg, Germany) according to the manufacturer's instructions.

Recombinant hGM-CSF from *E. coli* was internally produced as set out in Example 1.1 of WO 2005/105844. Recombinant hGM-CSF from yeast was obtained commercially under the trade name "Leukine" (Berlex, USA). Macaque GM-CSF was recombinantly produced in HEK293 cells.

A dilution series of conditioned medium containing natural hGM-CSF, as well as recombinant hGM-CSF from *E. coli* and yeast, and macaque GM-CSF were first tested for their potency to induce TF-1 proliferation. All three glycosylation variants of human GM-CSF and macaque GM-CSF exhibited very similar EC50 values for TF-1 activation. These were 10 pg/mL for *E. coli*-produced hGM-CSF, 15 pg/mL for yeast-produced hGM-CSF, 36 pg/mL for human lung cell-produced hGM-CSF, and 11 pg/mL for macaque GM-CSF, respectively (FIG. 14A).

The neutralizing activity of IgG B was then determined in the presence of 0.3 ng/mL recombinant hGM-CSF, or 0.2 ng/mL physiological hGM-CSF. After 72 hours, the proliferative status of TF-1 cells in the presence of different IgG B concentrations was quantified by a colorimetric reaction (FIG. 14B).

Taken together, the data shown in FIG. 14 show that IgG B inhibited GM-CSF-dependent proliferation of TF-1 cells at sub-nanomolar concentrations apparently independent of the glycosylation pattern of human GM-CSF. The glycosylation pattern of human GM-CSF therefore does not substantially influence the ability of IgG B to neutralize GM-CSF activity.

Example 10

Effect of IgG B on Biological Activities of Gm-CSF on Eosinophils

Example 10.1

Effect of IgG B on GM-CSF-Mediated Eosinophil Survival

One of the various biological activities of GM-CSF is prolongation of eosinophilic and neutrophilic granulocyte survival. Because lung inflammatory diseases are associated with local accumulation of eosinophils, which play a substantial role in maintaining inflammation, the efficacy of IgG B in inhibiting GM-CSF-mediated eosinophil survival was tested.

Eosinophils were isolated from peripheral blood of healthy donors by depletion of CD16+ neutrophils from the granulocyte population obtained by density gradient centrifugation and lysis of erythrocytes. Freshly isolated peripheral blood eosinophils were seeded at a density of $5 \times 10^4$ cells/well in RPMI 1640/10% FCS and Pen/Strep in a 96-well flat bottom microtest plate. GM-CSF was added in a dilution series ranging from 33 ng/mL to 10 pg/mL to monitor the concentration-dependent eosinophil survival. To analyze the inhibiting potential of IgG B on GM-CSF-dependent eosinophil survival, the antibody was added in a dilution series ranging from 10 μg/mL to 0.1 ng/mL. A final concentration of 0.1 ng/mL GM-CSF was used to effect eosinophil survival. After incubation for 72 h at 37° C., 5% $CO_2$ WST-1 reagent was added. The resulting colorimetric reaction corresponding to the portion of viable cells was quantified by measuring the absorbance at 450 nm The data were analyzed and fitted for half-maximal inhibition of survival (IC50) using the non-linear regression curve fit of the prism software package. As seen in FIG. 15A, a half-maximal effective dose (EC50) of 0.02 ng/mL rhGM-CSF was determined As seen in FIG. 15B, a potent neutralizing effect of IgG B was seen with a half-maximal inhibition of eosinophil survival at an antibody concentration of 0.13 nM.

These data indicate that IgG B is effective in inhibiting GM-CSF-dependent-eosinophil survival in a dose-dependent manner.

Example 10.2

Effect of IgG B on GM-CSF-Induced Eosinophil Activation

It was also desired to investigate the effect of IgG B on GM-CSF-induced activation of eosinophils. CD69 expression was found to be up-regulated on peripheral eosinophils (CD16−) isolated from human blood following stimulation for 20 h or 3 days with (a) 0.1 ng/mL GM-CSF or (b) 0.1 ng/mL GM-CSF, IL-3 and IL-5, but not with (c) 0.1 ng/mL IL-3 and IL-5 alone (FIG. 16A). Eosinophils cultured in the presence of medium alone showed no up-regulation of CD69. CD69 may therefore be taken as a marker for eosinophil activation by GM-CSF, and the expression level of CD69 was monitored as a measure of GM-CSF-dependent eosinophil activation. At both time points (20 h and 3 days), IgG B (10 μg/mL) almost completely prevented GM-CSF-dependent activation of eosinophils, as seen by lack of CD69 expression in flow cytometry.

Eosinophils were isolated as described above in Example 10.1 and cultivated at a density of $5 \times 10^5$ cells/well in RPMI 1640/10% FCS and Pen/Strep in a 48-well flat bottom microtest plate. Cells were incubated with medium alone or in the presence of 0.1 ng/mL GM-CSF alone or together with 0.1 ng/mL IL-3 or IL-5. 10 μg/mL IgGB were used for neutralization of GM-CSF. After an incubation of 1 or 3 days cells were analyzed for CD69 expression by flow cytometry.

CD69 detection by flow cytometry: Expression of CD69 on eosinophils was determined on a FACS Calibur instrument (Becton Dickinson). $10^5$ cells were incubated with 5 μL of a FITC-conjugated anti-human CD16 (clone 3G8, BD Biosciences) and a PE-conjugated anti-human CD69 antibody (clone FN50, BD Biosciences) each for 1 h at 4° C. As a negative control irrelevant, isotype-matched FITC- and PE-conjugated antibodies were used. After incubation, cells were washed twice with PBS, 1% FCS, 0.05% $NaN_3$ and resuspended in 250 μL PBS, 1% FCS, 0.05% NaN$_3$. Propidium iodide was added to label dead cells to a final concentration of 1 μg/mL immediately before FACS analysis. Data interpretation was done using the CellQuestPro software (BD Biosciences). Propidium iodide-positive (i.e. dead) cells were excluded from analysis of CD69 expression.

IgG B also reduced the percentage of live and activated eosinophils as monitored by propidium iodide staining of CD16/CD69$^+$ cells in the presence of 0.1 ng/mL GM-CSF. IgG B reduced the percentage of activated cells from 35% to 8% after 1 day and from 43% to 3% after 3 days of cultivation. In the presence of 0.1 ng/mL GM-CSF, IL-3 and IL-5, the percentage of live and activated eosinophils was reduced from 32% to 8% and from 48% to 11% after 1 and 3 days, respectively. Even though the upregulation of CD69 was completely inhibited by IgG B, higher numbers of resting eosinophils (CD16$^-$/CD69$^-$) survived for 3 days in the presence of 0.1 ng/mL GM-CSF, IL-3 and IL-5 as compared to cells incubated with medium or GM-CSF alone (FIG. 16A, last column). The same was observed for cells incubated in the presence of 0.1 ng/mL IL-3 plus IL-5.

In dose finding experiments, IgG B was added in dilution series to eosinophils cultured in the presence of 0.1 ng/mL GM-CSF (FIG. 16B). An inhibitory effect of IgG B on CD69-dependent median fluorescence intensity (MFI) was observed at a half-maximal concentration of 0.22 nM IgG B.

Taken together, these data indicate that IgG B is an effective neutralizer of GM-CSF activity in a biological context highly relevant for inflammatory airway diseases, for example asthma.

Example 11

Preliminary Ex Vivo Toxicology Studies Using IgG B

As explained above, neutralization of GM-CSF activity can be therapeutically advantageous in a number of disease settings. At the same time, however, GM-CSF plays an important role in the normal function of the immune system in combating exogenous pathogens, for example as in phagocytosis by neutrophil granulocytes and monocytes. This natural function of neutrophils and monocytes should remain unaffected in the presence of therapeutic amounts of IgG B. Therefore we investigated two aspects of the phagocytic process: 1) ingestion of bacteria (phagocytosis); and 2) oxidative burst activity (indicative for intracellular killing). These studies are detailed in the following examples.

Example 11.1

Ingestion of Bacteria (Phagocytosis)

Determination of granulocyte and monocyte phagocytic activity in heparinized whole blood was performed using the Phagotest Kit by Orpegen (Heidelberg, Germany). This test is based on the ingestion of opsonized, fluorescent-labelled *E. coli* by phagocytic cells. These cells can then be detected by green fluorescence in flow cytometry. 20 μl fluorescein-labelled opsonized *E. coli* were added to 100 μl of heparinized whole blood and incubated at 37° C. Incubation at 0° C. was performed as a negative control. After 10 min the phagocytic process was stopped by cooling samples on ice and addition of 100 μl Quenching solution (Orpegen). This solution allows discrimination of attachment and internalization of bacteria by quenching FITC fluorescence of surface bound bacteria while fluorescence of internalized particles remains unaffected. After three washing steps with 3 ml washing solution (Orpegen), erythrocytes were lysed. The remaining leucocytes were once washed with 3 ml Washing solution (Orpegen). After addition of 200 μl DNA staining solution, that allows exclusion of aggregated bacteria or cells, the cells were analyzed by flow cytometry. The percentage of cells having performed phagocytosis was determined by means of FITC-fluorescence.

To determine the influence of IgG B on phagocytosis, IgG B was added to three identical blood samples to a final concentration of 10 μg/ml. These three samples were then allowed to incubate at 37° C. with IgG B for various amounts of time prior to addition of *E. coli*. *E. coli* were added to the first sample immediately, whereas *E. coli* were added to the second and third samples after 24 and 48 hours, respectively.

Results observed for granulocytes: Directly after blood was taken over 98% of granulocytes ingested bacteria either in the presence or absence of IgG B (FIG. 17A). After incubation of blood samples with IgG B for 24 h a decrease to around 92% was determined without IgG B and to 90% in the presence of IgG B (FIG. 17B). After 48 h 81% of the granulocytes were phagocytosis positive in the absence and 89% in the presence of IgG B (FIG. 17C).

Results observed for monocytes: Irrespective of IgG B being present or not 98% monocytes were phagocytosing directly after blood was taken (FIG. 18A). After 24 h pre-incubation with IgG B 90% of the monocytes were positive (FIG. 18B). After 24 h pre-incubation without IgG B it were 92% monocytes. After 48 h we found 81% of the monocytes without IgG B and 89% with IgG B phagocytosis positive (FIG. 18C).

Example 11.2

Oxidative Burst

Determination of granulocyte and monocyte oxidative burst activity in heparinized whole blood was performed using the Phagoburst Kit by Orpegen (Heidelberg, Germany). This assay allows determination of the percentage of phagocytic cells which produce reactive oxidants by oxidation of the substrate dihydrorhodamine (DHR) 123 to the fluorescent R 123. Cells exhibiting oxidative burst activity can be identified in flow cytometry. Heparinized blood was incubated with different stimuli to induce oxidative burst activity: phorbol 12-myristate 13-acetate ("PMA") as a high stimulus; unlabelled, opsonized *E. coli* as intermediate stimulus and the chemotactic peptide N-formyl-MetLeuPhe (fMLP) as low stimulus. 100 μl whole blood was incubated with these stimuli at 37° C. As a negative control incubation was performed without stimulation. After 10 min incubation DHR 123 substrate solution was added and incubated for another 10 min DHR 123 is converted to the fluorescent R 123 by oxidizing cells. After three washing steps with 3 ml Washing solution (Orpegen), erythrocytes were lysed. The remaining leucocytes were once washed with 3 ml Washing solution (Orpegen). After addition of 200 μl DNA staining solution, that allows exclusion of aggregated bacteria or cells, the cells were analyzed by flow cytometry.

To determine the influence of IgG B on oxidative burst, IgG B was added to three identical blood samples to a final concentration of 10 μg/ml. Each of these three samples was then divided into three aliquots and allowed to incubate at 37° C. for various amounts of time prior to addition, to separate aliquots, of *E. coli*, fMLP or PMA. *E. coli*, fMLP or PMA were added to the three aliquots of the first sample immediately, whereas *E. coli*, fMLP or PMA were added to the three aliquots of the second and third samples after 24 and 48 hours, respectively. Parallel blood samples lacking IgG B were treated identically as above as controls. The results are shown below in Table 4, where "+" in the second column from the left indicates that IgG B is present in the sample aliquot tested, and "−" in the second column from the left indicates the IgG B-free control.

TABLE 4

Effect of IgG B on oxidative burst behaviour of granulocytes

| Timepoint | IgG B | Percent oxidizing granulocytes following stimulation with . . . | | | Results shown in . . . |
|---|---|---|---|---|---|
| | | E. coli | fMLP | PMA | |
| 0 h | − | 97 | 9 | 99 | FIG. 17D |
| | + | 94 | 10 | 99 | |
| 24 h | − | 82 | 8 | 97 | FIG. 17E |
| | + | 80 | 10 | 95 | |
| 48 h | − | 68 | 6 | 64 | FIG. 17F |
| | + | 71 | 5 | 64 | |

Similar results were obtained using monocytes instead of granulocytes. The experiment was performed analogously as described above, and the results are shown below in Table 5, where "+" in the second column from the left indicates that IgG B is present in the sample aliquot tested, and "−" in the second column from the left indicates the IgG B-free control.

TABLE 5

Effect of IgG B on oxidative burst behaviour of monocytes

| Timepoint | IgG B | Percent oxidizing monocytes following stimulation with . . . | | | Results shown in . . . |
|---|---|---|---|---|---|
| | | E. coli | fMLP | PMA | |
| 0 h | − | 62 | 0 | 79 | FIG. 18D |
| | + | 57 | 1 | 81 | |
| 24 h | − | 30 | 4 | 35 | FIG. 18E |
| | + | 26 | 6 | 28 | |
| 48 h | − | 29 | 4 | 17 | FIG. 18F |
| | + | 28 | 3 | 14 | |

Overall it can therefore be concluded that the presence of IgG B at physiologically relevant temperatures did not adversely affect the phagocytosis or oxidative killing of bacteria by either granulocytes or monocytes. In an in vivo context, these results suggest, then, that therapeutic administration of IgG B would not be expected to adversely affect the normal immune defenses of the patient.

The invention claimed is:

1. A human monoclonal antibody or fragment thereof which specifically binds to and neutralizes primate GM-CSF, comprising in its light chain variable region a CDR1 comprising an amino acid sequence as set out in SEQ ID NO: 16, a CDR2 comprising an amino acid sequence as set out in SEQ ID) NO: 17 and a CDR3comprising an amino acid sequence as set out in SEQ ID NO: 18; and comprising in its heavy chain variable region a CDR1 comprising an amino acid sequence as set out in SEQ ID NO: 14, a CDR2 comprising an amino acid sequence as set out in SEQ ID NO: 15 and a CDR3 comprising an amino acid sequence as set out in any of SEQ ID NOs: 1-13 or 56.

2. The human monoclonal antibody or fragment thereof according to claim 1 having an equilibrium disassociation constant $K_D$ of between about 4 $\times 10^{-9}$ M and about 0.04 $\times 10^{-9}$ M.

3. The human monoclonal antibody or fragment thereof according to claim 1 comprising in its light chain variable region a CDR1 comprising an amino acid sequence as set out in SEQ TD NO: 16, a CDR2 having an amino acid sequence as set out in SEQ ID NO: 17, and a CDR3 having an amino acid sequence as set out in SEQ ID) NO: 18, and comprising in its heavy chain variable region a CDR1 comprising an amino acid sequence as set out in SEQ ID NO: 14 a CDR2 comprising an amino acid sequence as set out in SEQ ID NO: 15 and a CDR3 comprising an amino acid sequence as set out in SEQ ID NO: 2.

4. The human monoclonal antibody or fragment thereof according to claim 1 wherein the primate GM-CSF is a human GM-CSF.

5. The human monoclonal antibody or fragment thereof according to claim 1 wherein the primate is a non-human primate.

6. The human monoclonal antibody fragment according to claim 1 wherein said fragment is an scFv, an Fv, a diabody, a tandem diabody, a Fab, a Fab' or a F(ab)$_2$.

7. The human monoclonal antibody according to claim 1, wherein the antibody is IgG.

8. The u an monoclonal antibody according to claim 7, wherein the IgG is an IgG1 or IgG4.

9. A polynucleotide molecule encoding the human monoclonal antibody or fragment according to claim 1.

10. A pharmaceutical composition comprising a human monoclonal antibody or fragment thereof according to claim 1 or the polynucleotide molecule according to claim 9.

11. The human monoclonal antibody or fragment thereof according to claim 1, comprising in its light chain variable region an amino acid sequence as set out in any of SEQ ID NOs: 19, 54 or 55.

12. The human monoclonal antibody or fragment thereof according to claim 1, comprising in its heavy chain variable region an amino acid sequence as set out in any of SEQ ID NOs: 20-33, 52 or 53.

13. The human monoclonal antibody according to claim 1, comprising a light chain amino acid sequence as set out in SEQ ID NO: 34 and a heavy chain amino acid sequence as set out in any of SEQ ID NOs: 35-48.

14. The human monoclonal antibody according to claim 13, comprising a light chain amino acid sequence as set out in SEQ ID NO: 34 and a heavy chain amino acid sequence as set out in SEQ ID NO: 35.

15. The human monoclonal antibody or fragment thereof according to claim 1, comprising in its light chain variable region an amino acid sequence as set out in SEQ ID NO: 19 and comprising in its heavy chain variable region an amino acid sequence as set out in SEQ ID NO: 21 or 52.

16. An immunoglobulin G antibody which binds to human GM-CSF, comprising in its light chain variable region a CDR1 comprising an amino acid sequence as set out in SEQ ID NO: 16, a CDR2 comprising an amino acid sequence as set out in SEQ ID NO: 17 and a CDR3 comprising an amino acid sequence as set out in SEQ ID NO: 18; and comprising in its heavy chain variable region a CDR1 comprising an amino acid sequence as set out in SEQ ID NO: 14, a CDR2 comprising an amino acid sequence as set out in SEQ ID NO: 15 and a CDR3 comprising an amino acid sequence as set out in SEQ ID NO: 2.

17. The antibody of claim 16 which binds to human GM-CSF with an equilibrium disassociation constant KD of between about $4 \times 10^{-9}$ M and about $0.04 \times 10^{-9}$ M.

18. The antibody of claim 16 which neutralizes human GM-CSF as determined in a TF-1 growth inhibition assay.

19. The antibody of claim 18 having n $IC_{50}$ value of approximately $3 \times 10^{-10}$ M as determined in a TF-1 growth inhibition assay.

20. The antibody of claim 17 or 18, comprising in its light chain variable region the amino acid sequence as set out in SEQ ID NO: 19 and comprising in its heavy chain variable region the amino acid sequence as set out in SEQ ID NO: 21.

* * * * *